United States Patent
Ohashi et al.

(10) Patent No.: US 8,105,748 B2
(45) Date of Patent: Jan. 31, 2012

(54) POLYMERIZABLE ANION-CONTAINING SULFONIUM SALT AND POLYMER, RESIST COMPOSITION, AND PATTERNING PROCESS

(75) Inventors: Masaki Ohashi, Joetsu (JP); Youichi Ohsawa, Joetsu (JP); Takeshi Kinsho, Joetsu (JP); Jun Hatakeyama, Joetsu (JP); Seiichiro Tachibana, Joetsu (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 299 days.

(21) Appl. No.: 12/580,953

(22) Filed: Oct. 16, 2009

(65) Prior Publication Data
US 2010/0099042 A1    Apr. 22, 2010

(30) Foreign Application Priority Data
Oct. 17, 2008    (JP) .................................. 2008-268147

(51) Int. Cl.
G03F 7/038    (2006.01)
G03F 7/039    (2006.01)
G03F 7/20    (2006.01)
G03F 7/30    (2006.01)
G03F 7/38    (2006.01)

(52) U.S. Cl. ..................... 430/270.1; 430/907; 430/910; 430/325; 430/326; 430/330; 430/942; 526/243; 526/245; 526/287; 562/113

(58) Field of Classification Search ........................ None
See application file for complete search history.

(56) References Cited

U.S. PATENT DOCUMENTS

| | | | |
|---|---|---|---|
| 5,635,332 A | 6/1997 | Nakano et al. | |
| 5,650,483 A | 7/1997 | Malik et al. | |
| 5,705,702 A | 1/1998 | Osawa et al. | |
| 5,945,250 A | 8/1999 | Aoai et al. | |
| 6,048,672 A | 4/2000 | Cameron et al. | |
| 6,306,555 B1 | 10/2001 | Schulz et al. | |
| 6,312,867 B1 | 11/2001 | Kinsho et al. | |
| 6,440,634 B1 | 8/2002 | Ohsawa et al. | |
| 6,723,483 B1 | 4/2004 | Oono et al. | |
| 6,830,866 B2 | 12/2004 | Kobayashi et al. | |
| 6,849,374 B2 | 2/2005 | Cameron et al. | |
| 7,288,359 B2 | 10/2007 | Iwasawa et al. | |
| 7,449,573 B2 | 11/2008 | Kodama et al. | |
| 7,537,880 B2 | 5/2009 | Harada et al. | |
| 7,569,326 B2 | 8/2009 | Ohsawa et al. | |
| 2002/0197558 A1 | 12/2002 | Ferreira et al. | |
| 2003/0113659 A1 | 6/2003 | Hatakeyama et al. | |
| 2004/0260031 A1 | 12/2004 | Takeda et al. | |
| 2007/0003871 A1 | 1/2007 | Kodama et al. | |
| 2007/0149702 A1 | 6/2007 | Ando et al. | |
| 2007/0231738 A1 | 10/2007 | Kaneko et al. | |
| 2008/0026331 A1 | 1/2008 | Hasegawa et al. | |
| 2008/0318160 A1 | 12/2008 | Ohsawa et al. | |
| 2009/0269696 A1* | 10/2009 | Ohsawa et al. | ............ 430/270.1 |
| 2010/0063232 A1* | 3/2010 | Nagai et al. | .................. 526/287 |

FOREIGN PATENT DOCUMENTS

| | | |
|---|---|---|
| JP | 4-230645 A | 8/1992 |
| JP | 7-25846 A | 1/1995 |
| JP | 8-311018 A | 11/1996 |
| JP | 9-15848 A | 1/1997 |
| JP | 11-282168 A | 10/1999 |
| JP | 2000-122296 A | 4/2000 |
| JP | 2000-336121 A | 12/2000 |
| JP | 2001-122850 A | 5/2001 |
| JP | 2001-181221 A | 7/2001 |
| JP | 2002-193887 A | 7/2002 |

(Continued)

OTHER PUBLICATIONS

Arimitsu et al., "Effect of Phenolic Hydroxyl Residues on the Improvement of Acid-Proliferation-Type Photoimaging Materials", Journal of Photopolymer Science and Technology, 1996, vol. 9, No. 1, pp. 29-30.

Arimitsu et al., "Sensitivity Enhancement of Chemical-Amplification-Type Photoimaging Materials by Acetoacetic Acid Derivatives", Journal of Photopolymer Science and Technology, 1995, vol. 8, No. 1, pp. 43-44.

Dammel et al., "193 nm Immersion Lithography—Taking the Plunge", Journal of Photopolymer Science and Technology, 2004, vol. 17, No. 4, p. 587-601.

(Continued)

Primary Examiner — Sin J. Lee
(74) Attorney, Agent, or Firm — Birch, Stewart, Kolasch & Birch, LLP

(57) ABSTRACT

A polymerizable anion-containing sulfonium salt having formula (1) is provided wherein $R^1$ is H, F, methyl or trifluoromethyl, $R^2$, $R^3$ and $R^4$ are $C_1$-$C_{10}$ alkyl, alkenyl or oxoalkyl or $C_6$-$C_{18}$ aryl, aralkyl or aryloxoalkyl, or two of $R^2$, $R^3$ and $R^4$ may bond together to form a ring with S, A is a $C_2$-$C_{20}$ hydrocarbon group having cyclic structure, and n is 0 or 1. The sulfonium salt generates a very strong sulfonic acid upon exposure to high-energy radiation. A resist composition comprising a polymer derived from the sulfonium salt is also provided.

11 Claims, 6 Drawing Sheets (1)

FOREIGN PATENT DOCUMENTS

| | | | |
|---|---|---|---|
| JP | 2002-193925 A | 7/2002 | |
| JP | 2002-214774 A | 7/2002 | |
| JP | 2003-66612 A | 3/2003 | |
| JP | 2003-140332 A | 5/2003 | |
| JP | 2004-2252 A | 1/2004 | |
| JP | 2004-115630 A | 4/2004 | |
| JP | 2004-531749 A | 10/2004 | |
| JP | 2005-8766 A | 1/2005 | |
| JP | 3613491 B2 | 1/2005 | |
| JP | 2005-84365 A | 3/2005 | |
| JP | 2005-266766 A | 9/2005 | |
| JP | 2006-178317 A | 7/2006 | |
| JP | 2007-145797 A | 6/2007 | |
| JP | 2007-197718 A | 8/2007 | |
| JP | 2007-297590 A | 11/2007 | |
| JP | 2008-31298 A | 2/2008 | |
| JP | 2008-111103 A | 5/2008 | |
| JP | 2008-133448 A | 6/2008 | |
| WO | WO 2006/121096 A1 | 11/2006 | |

OTHER PUBLICATIONS

DeVoe et al., "Photochemistry and Photophysics of Onium Salts", Advances in Photochemistry, 1992, vol. 17, p. 313-321, John-Wiley & Sons.

Kudo et al., "Enhancement of the Sensitivity of Chemical-Amplification-Type Photoimaging Materials by β-Tosyloxyketone Acetals", Journal of Photopolymer Science and Technology, 1995, vol. 8, No. 1. p. 45-46.

Miller et al., "Deoxygenation of Sulfoxides Promoted by Electrophilic Silicon Reagents: Preparation of Aryl-Substituted Sulfonium Salts", J. Org. Chem., 1988, 53, p. 5571-5573.

The Chemistry of the Sulphonium Group Part 1, 1981, p. 267-312, John-Wiley & Sons.

\* cited by examiner

US 8,105,748 B2

POLYMERIZABLE ANION-CONTAINING SULFONIUM SALT AND POLYMER, RESIST COMPOSITION, AND PATTERNING PROCESS

CROSS-REFERENCE TO RELATED APPLICATION

This non-provisional application claims priority under 35 U.S.C. §119(a) on Patent Application No. 2008-268147 filed in Japan on Oct. 17, 2008, the entire contents of which are hereby incorporated by reference.

TECHNICAL FIELD

This invention relates to (1) a polymerizable anion-containing sulfonium salt useful as a photoacid generator or a monomer to sulfonic acid polymer, (2) a polymer derived from the sulfonium salt monomer and capable of generating a sulfonic acid in response to high-energy radiation or heat, (3) a resist composition comprising the polymer, and (4) a patterning process using the resist composition.

BACKGROUND ART

While a number of recent efforts are being made to achieve a finer pattern rule in the drive for higher integration and operating speeds in LSI devices, DUV and VUV lithography is thought to hold particular promise as the next generation in microfabrication technology. In particular, photolithography using an ArF excimer laser as the light source is thought requisite to the micropatterning technique capable of achieving a feature size of 0.13 μm or less.

The ArF lithography started partial use from the fabrication of 130-nm node devices and became the main lithography since 90-nm node devices. Although lithography using $F_2$ laser (157 nm) was initially thought promising as the next lithography for 45-nm node devices, its development was retarded by several problems. A highlight was suddenly placed on the ArF immersion lithography that introduces a liquid having a higher refractive index than air (e.g., water, ethylene glycol, glycerol) between the projection lens and the wafer, allowing the projection lens to be designed to a numerical aperture (NA) of 1.0 or higher and achieving a higher resolution. See Journal of Photopolymer Science and Technology, Vol. 17, No. 4, p 587 (2004).

In the photolithography using an ArF excimer laser (wavelength 193 nm) as the light source, a high sensitivity resist material capable of achieving a high resolution at a small dose of exposure is needed to prevent the degradation of precise and expensive optical system materials. Among several measures for providing high sensitivity resist material, the most common is to select each component which is highly transparent at the wavelength of 193 nm. For example, polymers of acrylic acid and derivatives thereof, norbornene-maleic anhydride alternating copolymers, polynorbornene, ring-opening metathesis polymers, and hydrogenated ring-opening metathesis polymers have been proposed as the base resin. This choice is effective to some extent in that the transparency of a resin alone is increased.

Studies have also been made on photoacid generators. In prior art chemically amplified resist compositions for lithography using KrF excimer laser, photoacid generators capable of generating alkane- or arene-sulfonic acids are used. However, the use of these photoacid generators in chemically amplified resist compositions for ArF lithography results in an insufficient acid strength to scissor acid labile groups on the resin, a failure of resolution, or a low sensitivity. Thus these photoacid generators are not suited for the fabrication of microelectronic devices.

For the above reason, photoacid generators capable of generating perfluoroalkanesulfonic acids having a high acid strength are generally used in ArF chemically amplified resist compositions. These photoacid generators capable of generating perfluoroalkanesulfonic acids have already been developed for use in the KrF resist compositions. For instance, JP-A 2000-122296 and U.S. Pat. No. 6,048,672 (or JP-A 11-282168) describe photoacid generators capable of generating perfluorohexanesulfonic acid, perfluorooctanesulfonic acid, perfluoro-4-ethylcyclohexanesulfonic acid, and perfluorobutanesulfonic acid. JP-A 2002-214774, US Patent Application Publication 2003-0113659 A1 (JP-A 2003-140332), and US Patent Application Publication 2002-0197558 A1 describe novel acid generators capable of generating perfluoroalkyl ether sulfonic acids.

Among these, perfluorooctanesulfonic acid and homologues thereof (collectively referred to as PFOS) are considered problematic with respect to their non-degradability and biological concentration in the environment. Manufacturers made efforts to develop partially fluorinated alkane sulfonic acids having a reduced degree of fluorine substitution as the replacement to PFOS. For instance, JP-A 2004-531749 describes the synthesis of α,α-difluoroalkanesulfonic acid salts from α,α-difluoroalkene and a sulfur compound and discloses a resist composition comprising a photoacid generator which generates such sulfonic acid upon exposure, specifically di(4-tert-butylphenyl)iodonium 1,1-difluoro-2-(1-naphthyl)-ethanesulfonate. JP-A 2004-2252 describes the development of α,α,β,β-tetrafluoroalkanesulfonic acid salts from α,α,β,β-tetrafluoro-α-iodoalkane and sulfur compound and discloses a photoacid generator capable of generating such a sulfonic acid and a resist composition comprising the same. JP-A 2002-214774 discloses such photoacid generators as difluorosulfoacetic acid alkyl esters and difluorosulfoacetic acid amides although their synthesis method is lacking. Furthermore, JP-A 2005-266766 discloses a photosensitive composition comprising a compound capable of generating a partially fluorinated alkane sulfonic acid having a sulfonylamide structure derived from perfluoroalkylene disulfonyl difluoride.

In an attempt to form a fine feature size pattern with a pitch of less than 200 nm, the problem of pattern density dependency (or optical proximity effect), that is, the size difference between isolated and grouped patterns having different optical contrast becomes significant. Using a photoacid generator capable of generating an acid with low diffusion, the problem of pattern density dependency can be overcome to some extent, but not to a satisfactory extent. While the resist composition is required to achieve a further reduction of the pattern rule as well as a good balance of sensitivity, substrate adhesion, and etching resistance, it is also required to ameliorate the pattern density dependency fundamentally without a loss of resolution.

Under the circumstances, it was proposed to form a polymer from an acryloyloxyphenyldiphenylsulfonium salt as a monomer for enhancing sensitivity (as described in JP-A 4-230645) and to incorporate the monomer into a polyhydroxystyrene resin for improving the line width roughness (LWR) of this base resin (as described in JP-A 2005-84365). However, since the sulfonium salt is bonded at its cation side to the polymer, the sulfonic acid generated therefrom upon exposure to high-energy radiation is equivalent to the sulfonic acids generated by conventional photoacid generators, which is unsatisfactory to overcome the outstanding problem. Also, sulfonium salts having an anion side incorporated into the polymer backbone such as polystyrenesulfonic acid are disclosed as effective in enhancing sensitivity or improving resist pattern profile (Japanese Patent No. 3613491). The acids generated therefrom are arenesulfonic and alkylsulfonic acid derivatives which have too low an acid strength to sever acid labile groups, especially acid labile groups in ArF chemically amplified resist compositions. JP-A 2006-178317 discloses a polymer having a plurality of partially fluorinated sulfonic acid anions as polymerizable units, and a resist material comprising the polymer. WO 2006-121096 discloses a polymer having three partially fluorinated sulfonic acid anions in combination with a specific lactone compound. JP-A 2007-197718 discloses three anions. Since they are esters of carboxylic acids which are strong acids, they are expected to be readily hydrolyzable and low stable. Copolymers derived therefrom have an insufficient solubility in resist solvents. Furthermore, JP-A 2008-133448 discloses a sulfonium salt having a partially fluorinated alkane sulfonic acid anion as a polymerizable unit, which has insufficient resist performance in terms of LWR.

With respect to the immersion lithography, some problems arise from minute water droplets which are left on the resist and wafer after the immersion exposure. They can often cause damages and defects to the resist pattern profile. The resist pattern after development can collapse or deform into a T-top profile. There exists a need for a patterning process which can form a satisfactory resist pattern after development according to the immersion lithography.

The lithography techniques which are considered promising next to the ArF lithography include electron beam (EB) lithography, $F_2$ lithography, extreme ultraviolet (EUV) lithography, and x-ray lithography. In these techniques, exposure must be done in vacuum or reduced pressure, which allows the sulfonic acid generated during exposure to volatilize, failing to form a satisfactory pattern profile. The sulfonic acid volatilized is damaging to the exposure system. In the EB and EUV lithography, it is desired to provide a resist material capable of minimizing the influence of acid diffusion in order to comply with further pattern size reductions.

Citation List
Patent Document 1: JP-A 2000-122296
Patent Document 2: U.S. Pat. No. 6,048,672 (or JP-A H11-282168)
Patent Document 3: JP-A 2002-214774
Patent Document 4: US 2003-0113659 A1 (JP-A 2003-140332)
Patent Document 5: US 2002-0197558 A1
Patent Document 6: JP-A 2004-531749
Patent Document 7: JP-A 2004-2252
Patent Document 8: JP-A 2005-266766
Patent Document 9: JP-A 4-230645
Patent Document 10: JP-A 2005-84365
Patent Document 11: JP 3613491
Patent Document 12: JP-A 2006-178317
Patent Document 13: WO 06-121096
Patent Document 14: JP-A 2007-197718
Patent Document 15: JP-A 2008-133448
Patent Document 16: U.S. Pat. No. 7,537,880 (JP-A 2008-111103)
Non-Patent Document 1: Journal of Photopolymer Science and Technology, Vol. 17, No. 4, p 587 (2004)

SUMMARY OF INVENTION

An object of the present invention is to provide (1) a polymerizable anion-containing sulfonium salt useful as a monomer, (2) a polymer obtained from the sulfonium salt, (3) a resist composition comprising the polymer, which composition exhibits a high resolution and exposure latitude when processed by the photolithography using high-energy radiation, typically ArF excimer laser radiation, EUV radiation or EB as the light source, and (4) a patterning process using the resist composition.

The inventors have found that a polymerizable anion-containing sulfonium salt having the general formula (1) shown below can be easily prepared, and that a resist composition comprising as a base resin a polymer comprising recurring units of the polymerizable anion-containing sulfonium salt is improved in such properties as exposure latitude, pattern density dependency, and line width roughness (LWR), and best suited for precise micropatterning.

Thus the invention provides a polymerizable anion-containing sulfonium salt, a polymer derived therefrom, a resist composition, and a patterning process, as defined below.

[Claim 1]

A sulfonium salt having the general formula (1).

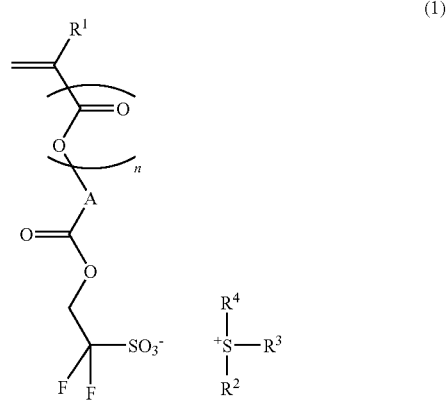

(1)

Herein $R^1$ is hydrogen, fluorine, methyl or trifluoromethyl, $R^2$, $R^3$ and $R^4$ are each independently a substituted or unsubstituted, straight or branched $C_1$-$C_{10}$ alkyl, alkenyl or oxoalkyl group or a substituted or unsubstituted $C_6$-$C_{18}$ aryl, aralkyl or aryloxoalkyl group, or at least two of $R^2$, $R^3$ and $R^4$ may bond together to form a ring with the sulfur atom, A is a divalent $C_2$-$C_{20}$ hydrocarbon group of cyclic structure which may contain a heteroatom, and n is 0 or 1.

[Claim 2]

A polymer capable of generating a sulfonic acid in response to high-energy radiation or heat, the sulfonic acid comprising recurring units of the general formula (1a).

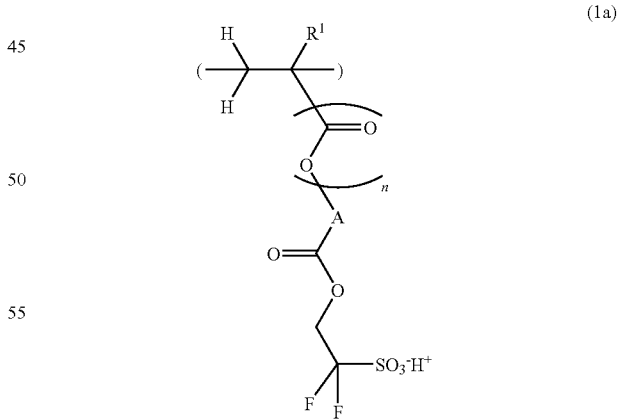

(1a)

Herein $R^1$ is hydrogen, fluorine, methyl or trifluoromethyl, A is a divalent $C_2$-$C_{20}$ hydrocarbon group of cyclic structure which may contain a heteroatom, and n is 0 or 1.

[Claim 3]

A polymer comprising recurring units of the general formula (1b).

(1b)

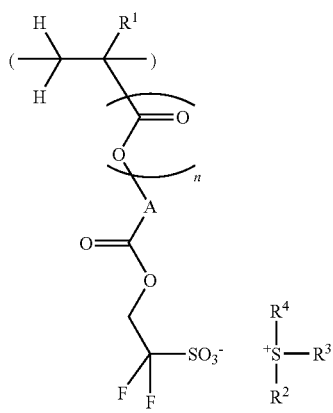

Herein R¹ is hydrogen, fluorine, methyl or trifluoromethyl, R², R³ and R⁴ are each independently a substituted or unsubstituted, straight or branched $C_1$-$C_{10}$ alkyl, alkenyl or oxoalkyl group or a substituted or unsubstituted $C_6$-$C_{18}$ aryl, aralkyl or aryloxoalkyl group, or at least two of R², R³ and R⁴ may bond together to form a ring with the sulfur atom, A is a divalent $C_2$-$C_{20}$ hydrocarbon group of cyclic structure which may contain a heteroatom, and n is 0 or 1.

[Claim 4]

The polymer of claim 3, further comprising recurring units of at least one type selected from the general formulae (2) to (6).

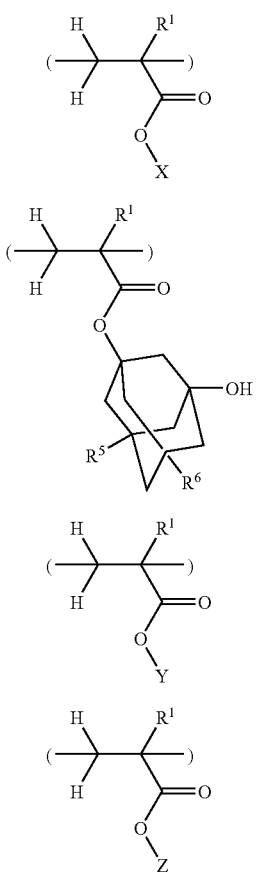

(2)

(3)

(4)

(5)

-continued

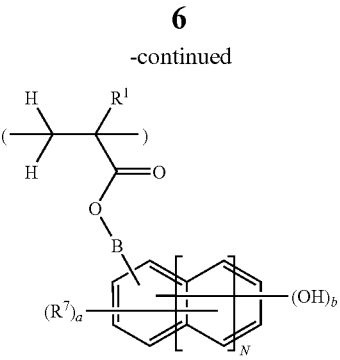

(6)

Herein R¹ is as defined above, R⁵ and R⁶ are each independently hydrogen or hydroxyl, X is an acid labile group, Y is a substituent group having lactone structure, Z is hydrogen, $C_1$-$C_{15}$ fluoroalkyl or $C_1$-$C_{15}$ fluoroalcohol-containing substituent group, N is an integer of 0 to 2, R⁷ is hydrogen or $C_1$-$C_{10}$ alkyl, B is a single bond or a divalent $C_1$-$C_{10}$ hydrocarbon group which may have oxygen substituted thereon, a is an integer of 0 to 3, and b is an integer of 1 to 3.

[Claim 5]

The polymer of claim 3 or 4, further comprising recurring units of at least one type selected from the general formulae (7) to (11).

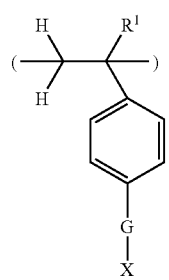

(7)

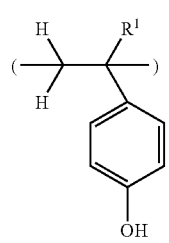

(8)

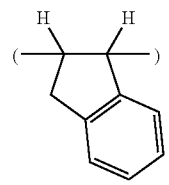

(9)

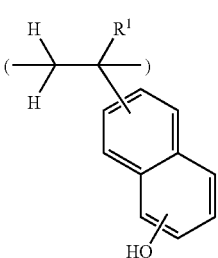

(10)

-continued (11)

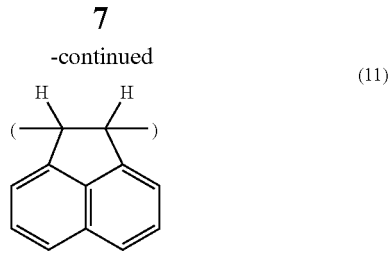

Herein R¹ is as defined above, X is an acid labile group, and G is oxygen or carbonyloxy (—C(=O)O—).

[Claim 6]

A resist composition comprising the polymer of any one of claims 3 to 5 as a base resin.

[Claim 7]

A resist composition comprising the polymer of any one of claims 3 to 5 and a polymer free of recurring units of formula (1b) as a base resin.

[Claim 8]

The resist composition of claim 6 or 7, further comprising a surfactant which is insoluble in water and soluble in an alkaline developer.

[Claim 9]

A pattern forming process comprising the steps of applying the resist composition of any one of claims 6 to 8 onto a substrate to form a coating, heat treating the coating and exposing it to high-energy radiation through a photomask, optionally heat treating the exposed coating, and developing it with a developer.

[Claim 10]

A pattern forming process comprising the steps of applying the resist composition of any one of claims 6 to 8 onto a substrate to form a resist coating, heat treating the resist coating, applying onto the resist coating a protective coating which is insoluble in water and soluble in an alkaline developer, exposing the coated substrate to high-energy radiation from a projection lens through a photomask while holding water between the substrate and the projection lens, optionally heat treating the exposed coating, and developing it with a developer.

[Claim 11]

A pattern forming process comprising the steps of applying the resist composition of any one of claims 6 to 8 onto a substrate to form a coating, heat treating the coating, imagewise writing with an electron beam, optionally heat treating the coating, and developing it with a developer.

It is noted that the resist composition of the invention can be applied to the immersion lithography. The immersion lithography involves prebaking a resist film and exposing the resist film to light through a projection lens with a liquid medium interposed between the resist film and the projection lens. The ArF immersion lithography generally uses pure water as the immersion medium. This technology, combined with a projection lens having a NA of at least 1.0, is important for the ArF lithography to survive to the 65 nm node and forth, with a further development thereof being accelerated.

The resist composition of the invention allows the feature size of the pattern after development to be reduced by various shrinkage techniques. For example, the hole size can be shrunk by such known techniques as thermal flow, RELACS, SAFIRE, and WASOOM. More effective shrinkage of hole size by thermal flow is possible particularly when the inventive polymer is blended with a hydrogenated cycloolefin ring-opening metathesis polymerization (ROMP) polymer having a low Tg.

ADVANTAGEOUS EFFECTS OF INVENTION

Since the polymerizable anion-containing sulfonium salt has fluorine atoms at α-position relative to the sulfonic acid, it generates a sulfonic acid upon exposure to high-energy radiation, the sulfonic acid having a very high acidity enough to facilitate efficient scission of acid labile groups in chemically amplified resist compositions. The sulfonium salt is quite useful as a monomer for producing a base resin in a radiation-sensitive resist composition. Then, a radiation-sensitive resist composition comprising the polymer as a base resin exhibits a high resolution and is improved in pattern density dependency and exposure margin. The polymer is advantageously used as a resist material in precise micropatterning.

In the ArF immersion lithography, the leach-out of sulfonic acid in water is minimized, and the influence of water left on the wafer is minimized to restrain defect formation. In the disposal of resist-containing waste liquid after the device fabrication, (meth)acrylate moieties are hydrolyzable under basic conditions so that the polymer may be transformed into less accumulative compounds of lower molecular weight. In the disposal by combustion, the polymer is more combustible because of a low degree of fluorine substitution.

DESCRIPTION OF EMBODIMENTS

Figure 1:
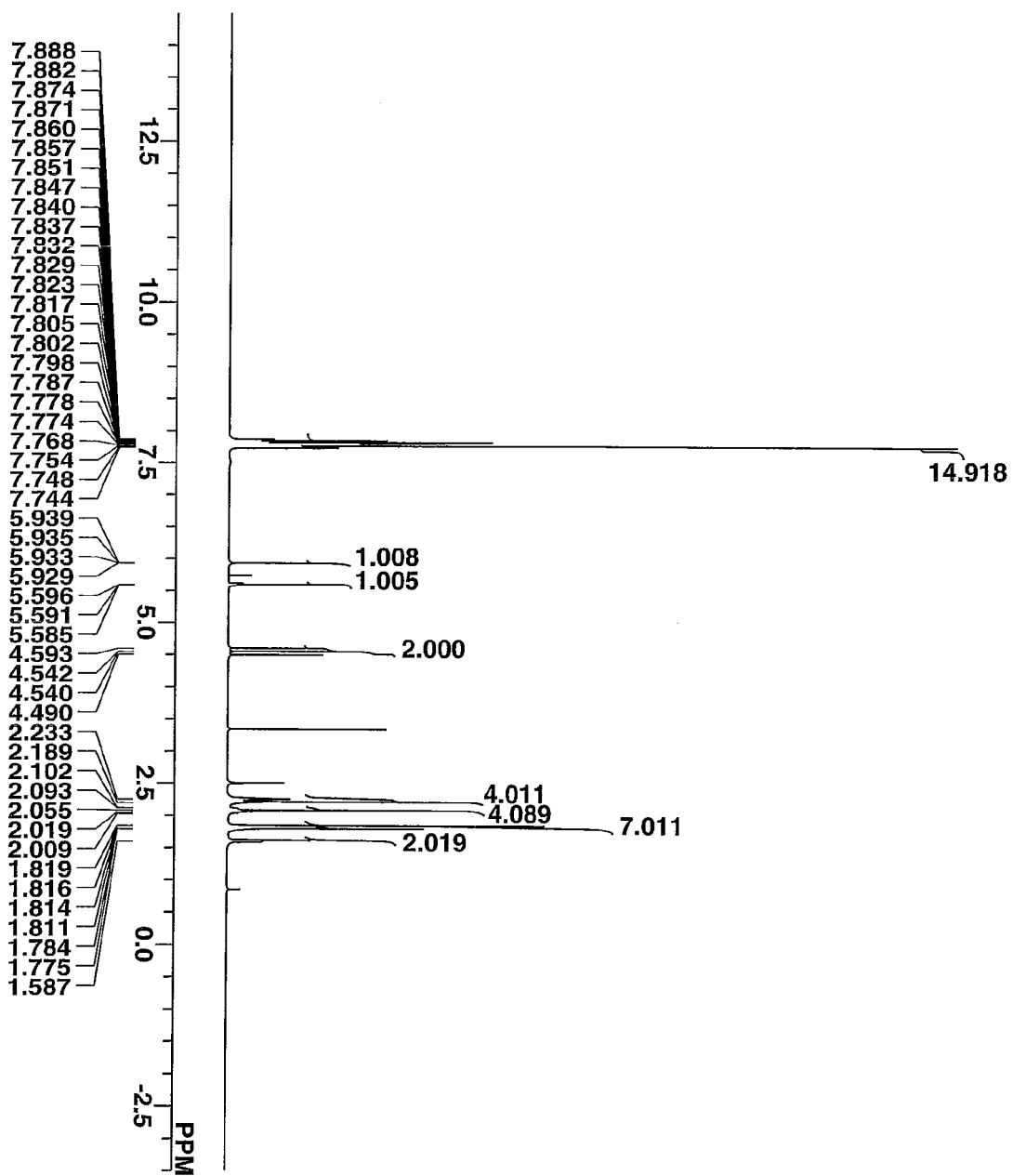
FIG. 1 is a diagram showing the ¹H-NMR spectrum of Monomer 1 in Synthesis Example 1-21.

As used herein, the singular forms "a," "an" and "the" include plural referents unless the context clearly dictates otherwise. The notation (Cn-Cm) means a group containing from n to m carbon atoms per group. The term "high-energy radiation" is intended to encompass UV, deep UV, electron beam, EUV, x-ray, excimer laser, γ-ray and synchrotron radiation. In structural formulae, the broken line indicates a valence bond.

Sulfonium Salt

The first aspect of the invention relates to a polymerizable anion-containing sulfonium salt having the general formula (1).

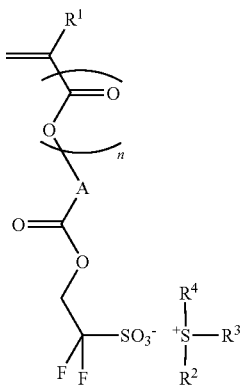

(1)

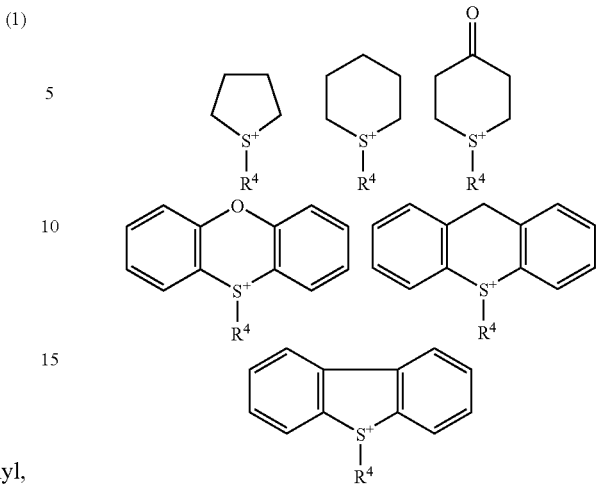

Herein R¹ is hydrogen, fluorine, methyl or trifluoromethyl, R², R³ and R⁴ are each independently a substituted or unsubstituted, straight or branched $C_1$-$C_{10}$ alkyl, alkenyl or oxoalkyl group or a substituted or unsubstituted $C_6$-$C_{18}$ aryl, aralkyl or aryloxoalkyl group, or at least two of R², R³ and R⁴ may bond together to form a ring with the sulfur atom in the formula, A is a divalent $C_2$-$C_{20}$ hydrocarbon group of cyclic structure which may contain a heteroatom, and n is 0 or 1.

In formula (1), R², R³ and R⁴ are each independently a substituted or unsubstituted, straight or branched $C_1$-$C_{10}$ alkyl, alkenyl or oxoalkyl group or a substituted or unsubstituted $C_6$-$C_{18}$ aryl, aralkyl or aryloxoalkyl group, or any two or more of R², R³ and R⁴ may bond together to form a ring with the sulfur atom in the formula.

Specifically, suitable alkyl groups include, but are not limited to, methyl, ethyl, propyl, isopropyl, n-butyl, sec-butyl, tert-butyl, pentyl, hexyl, heptyl, octyl, cyclopentyl, cyclohexyl, cycloheptyl, cyclopropylmethyl, 4-methylcyclohexyl, cyclohexylmethyl, norbornyl, and adamantyl. Suitable alkenyl groups include, but are not limited to, vinyl, allyl, propenyl, butenyl, hexenyl, and cyclohexenyl. Suitable oxoalkyl groups include, but are not limited to, 2-oxocyclopentyl, 2-oxocyclohexyl, 2-oxopropyl, 2-oxoethyl, 2-cyclopentyl-2-oxoethyl, 2-cyclohexyl-2-oxoethyl, and 2-(4-methylcyclohexyl)-2-oxoethyl. Suitable aryl groups include, but are not limited to, phenyl, naphthyl, thienyl, alkoxyphenyl groups such as 4-hydroxyphenyl, 4-methoxyphenyl, 3-methoxyphenyl, 2-methoxyphenyl, 4-ethoxyphenyl, 4-tert-butoxyphenyl, and 3-tert-butoxyphenyl, alkylphenyl groups such as 2-methylphenyl, 3-methylphenyl, 4-methylphenyl, 4-ethylphenyl, 4-tert-butylphenyl, 4-n-butylphenyl, and 2,4-dimethylphenyl, alkylnaphthyl groups such as methylnaphthyl and ethylnaphthyl, alkoxynaphthyl groups such as methoxynaphthyl and ethoxynaphthyl, dialkylnaphthyl groups such as dimethylnaphthyl and diethylnaphthyl, and dialkoxynaphthyl groups such as dimethoxynaphthyl and diethoxynaphthyl. Suitable aralkyl groups include benzyl, 1-phenylethyl, and 2-phenylethyl. Suitable aryloxoalkyl groups are 2-aryl-2-oxoethyl groups such as 2-phenyl-2-oxoethyl, 2-(1-naphthyl)-2-oxoethyl, and 2-(2-naphthyl)-2-oxoethyl. When any two or more of R², R³ and R⁴ bond together to form a ring with the sulfur atom, exemplary cyclic structures are shown below.

In the formulae, R⁴ is as defined above.

Illustrative non-limiting examples of the sulfonium cation include triphenylsulfonium, 4-hydroxyphenyldiphenylsulfonium, bis(4-hydroxyphenyl)phenylsulfonium, tris(4-hydroxyphenyl)sulfonium, 4-tert-butoxyphenyldiphenylsulfonium, bis(4-tert-butoxyphenyl)phenylsulfonium, tris(4-tert-butoxyphenyl)sulfonium, 3-tert-butoxyphenyldiphenylsulfonium, bis(3-tert-butoxyphenyl)phenylsulfonium, tris(3-tert-butoxyphenyl)sulfonium, 3,4-di-tert-butoxyphenyldiphenylsulfonium, bis(3,4-di-tert-butoxyphenyl)phenylsulfonium, tris(3,4-di-tert-butoxyphenyl)sulfonium, diphenyl(4-thiophenoxyphenyl)sulfonium, 4-tert-butoxycarbonylmethyloxyphenyldiphenylsulfonium, tris(4-tert-butoxycarbonylmethyloxyphenyl)sulfonium, (4-tert-butoxyphenyl)bis(4-dimethylaminophenyl)sulfonium, tris(4-dimethylaminophenyl)sulfonium, 2-naphthyldiphenylsulfonium, (4-hydroxy-3,5-dimethylphenyl)diphenylsulfonium, (4-n-hexyloxy-3,5-dimethylphenyl)diphenylsulfonium, dimethyl(2-naphthyl)sulfonium, 4-hydroxyphenyldimethylsulfonium, 4-methoxyphenyldimethylsulfonium, trimethylsulfonium, 2-oxocyclohexylcyclohexylmethylsulfonium, trinaphthylsulfonium, tribenzylsulfonium, diphenylmethylsulfonium, dimethylphenylsulfonium, 2-oxo-2-phenylethylthiacyclopentanium, diphenyl-2-thienylsulfonium, 4-n-butoxynaphthyl-1-thiacyclopentanium, 2-n-butoxynaphthyl-1-thiacyclopentanium, 4-methoxynaphthyl-1-thiacyclopentanium, and 2-methoxynaphthyl-1-thiacyclopentanium.

Inter alia, triphenylsulfonium, 4-tert-butylphenyldiphenylsulfonium, 4-tert-butoxyphenyldiphenylsulfonium, tris(4-tert-butylphenyl)sulfonium, tris(4-tert-butoxyphenyl)sulfonium, and dimethylphenylsulfonium are preferred.

In formula (1), R¹ is a hydrogen atom, fluorine atom, methyl group or trifluoromethyl group, with hydrogen and methyl being preferred. The subscript n is 0 or 1. A is a divalent $C_2$-$C_{20}$ hydrocarbon group of cyclic structure which may contain a heteroatom, and may be either an alicyclic hydrocarbon or aromatic hydrocarbon. Exemplary alicyclic hydrocarbons include cyclopropane, cyclobutane, cyclopentane, cyclohexane, cycloheptane, cyclooctane, cyclononane, cyclodecane, cycloundecane, cyclododecane, cyclotridecane, cyclotetradecane, cyclopentadecane, decalin, bicyclo[4.3.0]nonane, tricyclo[5.3.1.0$^{2,6}$]decane, tetracyclo[6.2.1.1$^{3,6}$.0$^{2,7}$]decane, perhydropentalene, perhydroheptalene, perhydroazulene, perhydroindene, spiro[3.3]heptane, spiro[3.4]octane, spiro[4.5]decane, bicyclo

[2.2.1]heptane, bicyclo[2.2.2]octane, adamantane, and noradamantane. Exemplary aromatic hydrocarbons include benzene, naphthalene, phenanthrene, anthracene, azulene, and acenaphthylene. Suitable heteroatom-containing cyclic compounds include oxirane, oxetane, oxolane, dioxolane, oxane, 1,3-dioxane, 1,4-dioxane, 7-oxa-bicyclo[2.2.1]heptane, thiophene, pyrrolidine, piperidine, and morpholine as well as tetralin and indane. Also included are the foregoing groups in which some hydrogen atoms are substituted by hydroxyl, alkoxy, carboxy, alkoxycarbonyl, oxo, amino, alkylamino, cyano, mercapto, alkylthio, sulfo, and other groups. Those hydrocarbons from which two hydrogen atoms have been eliminated are the divalent hydrocarbon groups.

Specifically exemplary structures of the anion moiety in formula (1) are illustrated below, but not limited thereto.

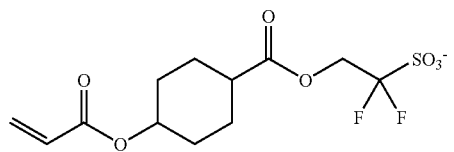
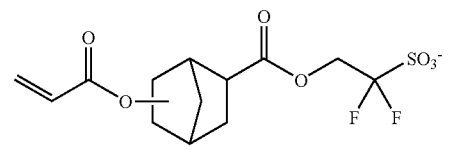
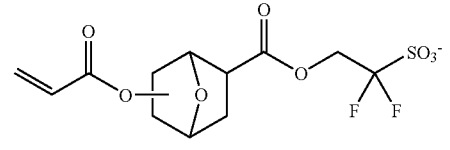
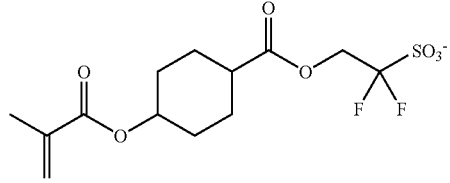
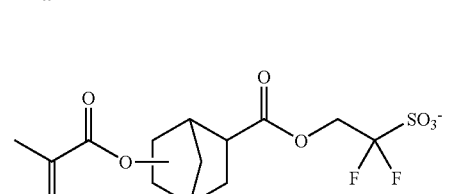
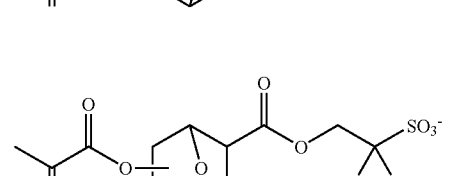
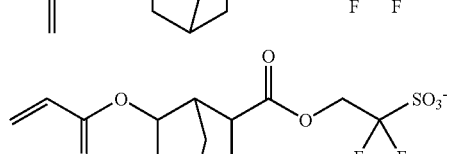
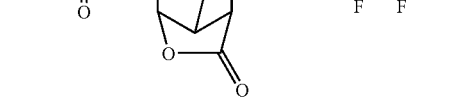

-continued

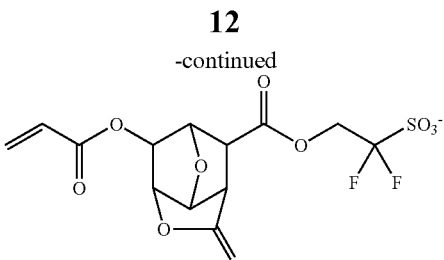
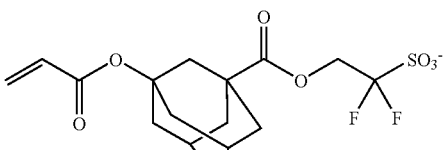
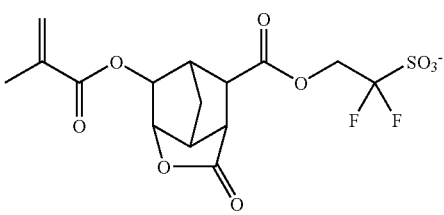
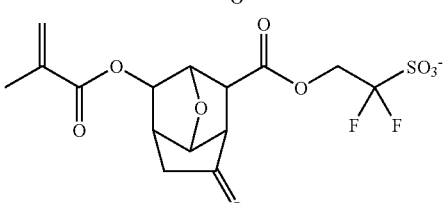
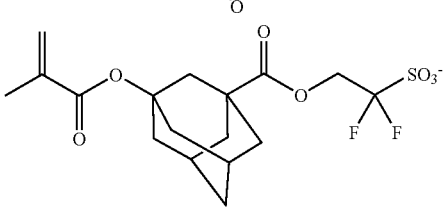
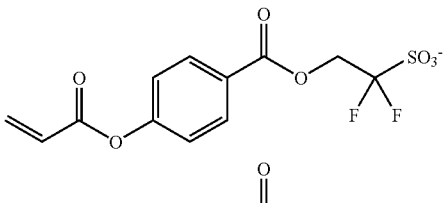
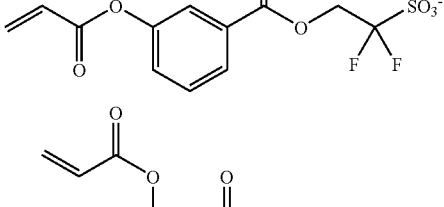
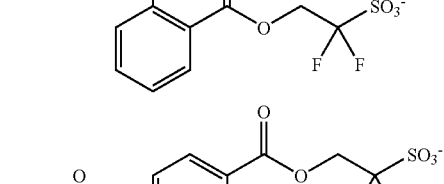
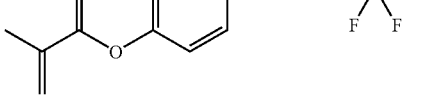

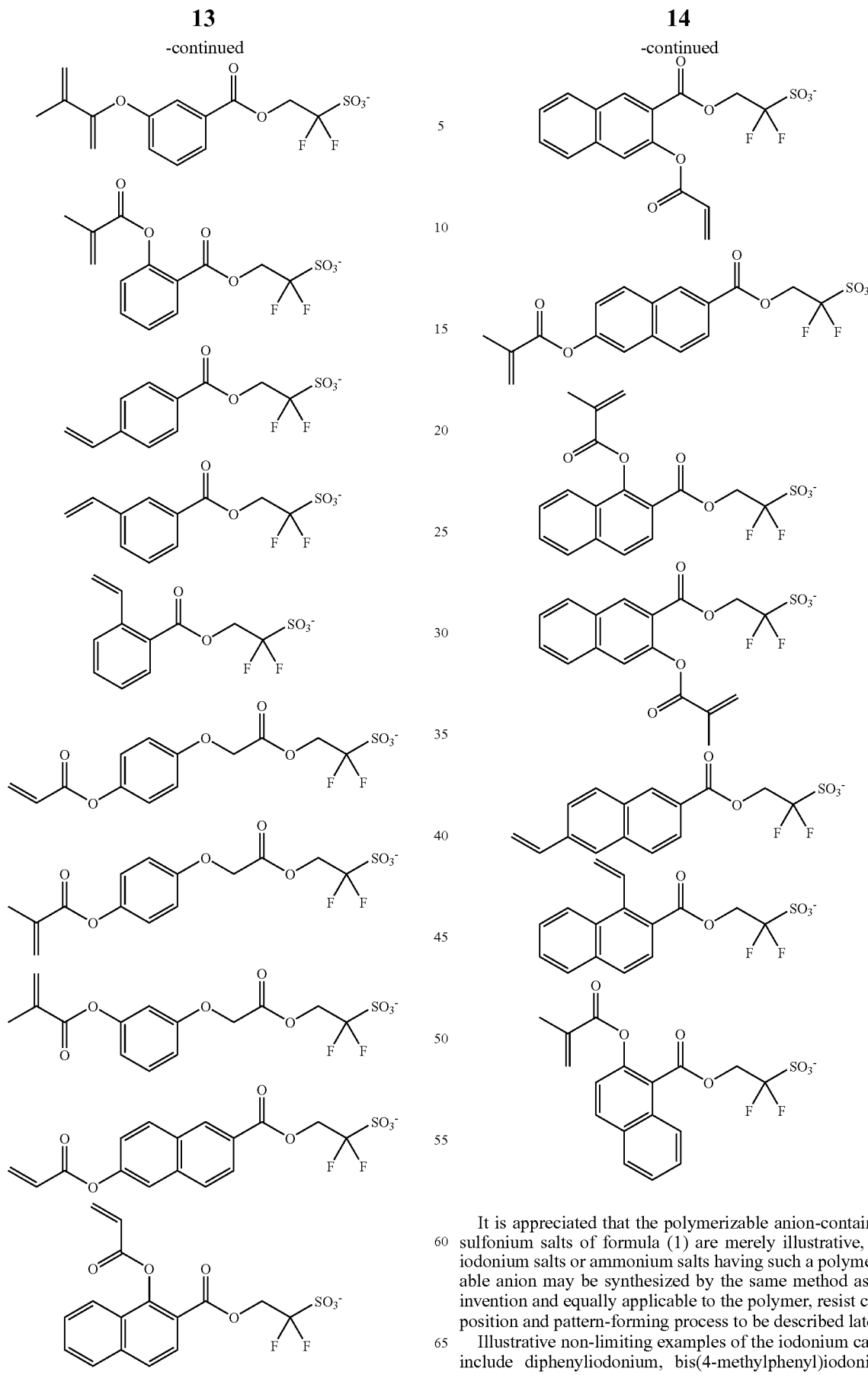

It is appreciated that the polymerizable anion-containing sulfonium salts of formula (1) are merely illustrative, and iodonium salts or ammonium salts having such a polymerizable anion may be synthesized by the same method as the invention and equally applicable to the polymer, resist composition and pattern-forming process to be described later.

Illustrative non-limiting examples of the iodonium cation include diphenyliodonium, bis(4-methylphenyl)iodonium, bis(4-(1,1-dimethylethyl)phenyl)iodonium, bis(4-(1,1-dimethylpropyl)phenyl)iodonium, and (4-(1,1-dimethylethoxy)phenyl)phenyliodonium. Illustrative non-limiting examples of the ammonium salt include tertiary ammonium salts such as trimethylammonium, triethylammonium, tributylammonium and N,N-dimethylanilinium, and quaternary ammonium salts such as tetramethylammonium, tetraethylammonium, and tetrabutylammonium. The iodonium salt having the specific polymerizable anion and a polymer having the iodonium salt in recurring units may be used as a component having a photoacid generating ability or thermal acid generating ability. The ammonium salt having the specific polymerizable anion and a polymer having the ammonium salt in recurring units may be used as a thermal acid generator.

The second aspect of the invention relates to a polymer or high-molecular weight compound capable of generating a sulfonic acid in response to high-energy radiation (e.g., UV, deep-UV, EUV, electron beam, x-ray, excimer laser, gamma-ray and synchrotron radiation) or heat, the sulfonic acid comprising recurring units of the general formula (1a):

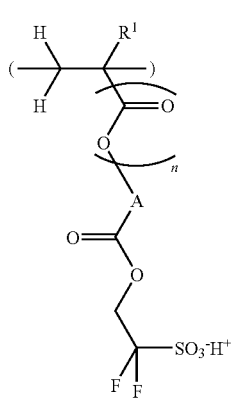

(1a)

Herein $R^1$ is hydrogen, fluorine, methyl or trifluoromethyl, A is a divalent $C_2$-$C_{20}$ hydrocarbon group of cyclic structure which may contain a heteroatom, and n is 0 or 1.

In formula (1a), $R^1$, A and n are as defined above. When an acid generator is incorporated in a polymer unit (referred to as polymer-bound PAG, hereinafter), acid diffusion is suppressed and as a consequent, parameters such as exposure latitude and mask error factor may be improved, but line width roughness (LWR) may be degraded. When a resist composition comprising a polymer having the sulfonium salt of the invention incorporated therein is used, LWR may also be improved because the polymer-bound PAG is endowed with an appropriate mobility due to the interposition of a linker unit represented by A in formula (1a). Since the acid generator has fluorine atoms at α-position relative to the sulfonic acid, it generates a sulfonic acid upon exposure to high-energy radiation, the sulfonic acid having a very high strength enough to facilitate efficient scission of acid labile groups in chemically amplified resist compositions. The compound is quite useful as a monomer for producing a base resin in a radiation-sensitive resist composition.

Now the method for synthesizing the sulfonium salt having a polymerizable anion represented by formula (1) according to the invention is described.

The sulfonium salt having a polymerizable anion represented by formula (1) can be synthesized by converting a carboxylic acid having a polymerizable functional group such as (meth)acryloyl or vinyl ($CH_2$=$CR^1$—$(COO)_n$-A-COOH) into a carboxylic acid chloride and reacting it with triphenylsulfonium 1,1-difluoro-2-hydroxyethanesulfonate, which has been synthesized as described below, under basic conditions. The reaction may preferably be carried out by dissolving the reactants in a solvent such as methylene chloride, tetrahydrofuran or acetonitrile, adding a base such as triethylamine, pyridine or 4-dimethylaminopyridine thereto, and cooling or heating the system as desired.

The synthesis formulation described above is merely exemplary and the invention is not limited thereto.

Briefly noted herein is the synthesis of triphenylsulfonium 1,1-difluoro-2-hydroxyethanesulfonate. The desired compound may be synthesized by reacting 2-bromo-2,2-difluoroethanol with a carboxylic acid chloride to form 2-bromo-2,2-difluoroethyl alkanecarboxylate or 2-bromo-2,2-difluoroethyl arenecarboxylate, converting the bromo group into sodium sulfinate using a sulfur compound such as sodium dithionite, and converting sulfinic acid into sulfonic acid using an oxidizing agent such as hydrogen peroxide. The outline of the process is illustrated below.

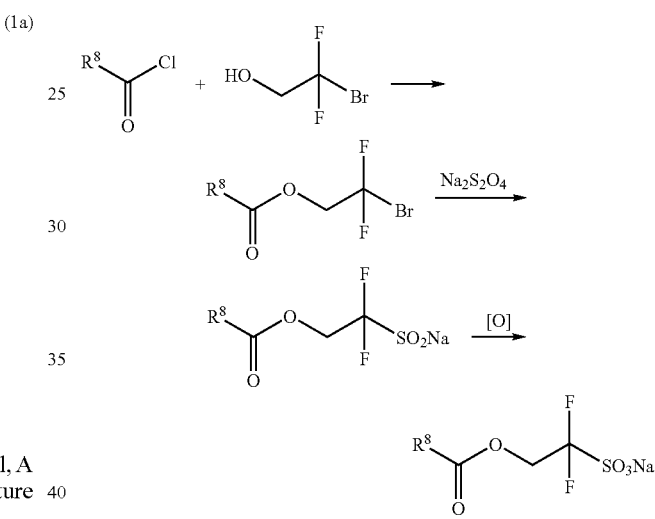

Herein $R^8$ is a straight, branched or cyclic $C_1$-$C_{20}$ alkyl group which may contain a heteroatom.

The steps of esterification, conversion from alkane halide to sodium sulfinate, and conversion to sulfonic acid are well known, while the formulations used in the latter two steps are described in JP-A 2004-2252.

Subsequent ion exchange reaction between the resulting sodium sulfonate and a sulfonium salt compound yields the desired sulfonium salt. With respect to ion exchange reaction, reference is made to JP-A 2007-145797.

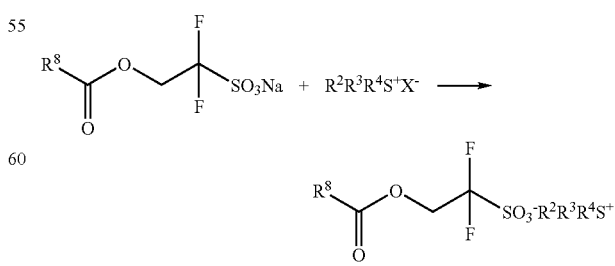

Herein, $R^2$ to $R^4$ and $R^8$ are as defined above. $X^-$ is a counter anion. Exemplary anions include, but are not limited to, halide ions such as I⁻, Br⁻ and Cl⁻, sulfate and alkylsulfate anions such as sulfate and methylsulfate anions, carboxylate anions such as acetate and benzoate, alkanesulfonates such as methanesulfonate and propanesulfonate, arenesulfonates such as benzenesulfonate and p-toluenesulfonate, and hydroxide.

Further, the acyl group $R^8CO$— introduced as above is subjected to ester hydrolysis or solvolysis, thereby synthesizing triphenylsulfonium 1,1-difluoro-2-hydroxyethane-sulfonate. The outline of the process is illustrated below.

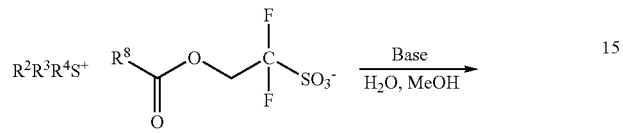

Note that $R^2$ to $R^4$ and $R^8$ are as defined above, and Me is methyl.

This formulation makes it possible to introduce $R^8$, even when $R^8$ is a labile substituent group, through esterification of 1,1-difluoro-2-hydroxyethanesulfonate. Sulfonium salts other than triphenylsulfonium and iodonium salts may be similarly synthesized.

The starting sulfonium and iodonium salts may be synthesized according to the teachings of The Chemistry of Sulfonium Group Part 1, John-Wiley & Sons (1981), Advanced Photochemistry, vol. 17, John-Wiley & Sons (1992), J. Org. Chem., 1988, 53, 5571-5573, JP-A 8-311018, JP-A 9-15848, JP-A 2001-122850, JP-A 7-25846, JP-A 2001-181221, JP-A 2002-193887, and JP-A 2002-193925. An onium cation having an acryloyloxy or methacryloyloxy group as a polymerizable substituent group may be synthesized according to the methods of JP-A 4-230645 and JP-A 2005-84365, by reacting a hydroxyphenyldiphenylsulfonium halide (preformed) with acryloyl chloride of methacryloyl chloride under basic conditions.

Polymer

The polymer or high-molecular weight compound of the invention comprises recurring units derived from the sulfonium salt having a polymerizable anion represented by formula (1). Specifically, the recurring units derived from the sulfonium salt having a polymerizable anion represented by formula (1) include units of the general formula (1b):

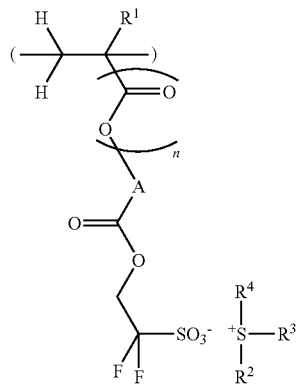

wherein $R^1$ to $R^4$, A and n are as defined above.

In addition to the recurring units of formula (1b), the polymer of the invention may further comprise recurring units of at least one type selected from the general formulae (2) to (6).

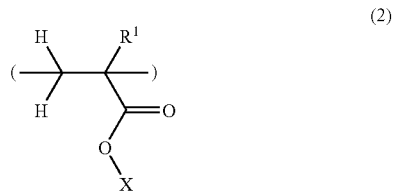

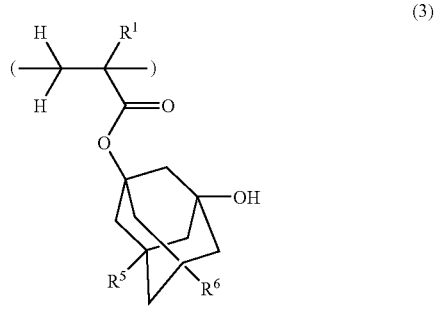

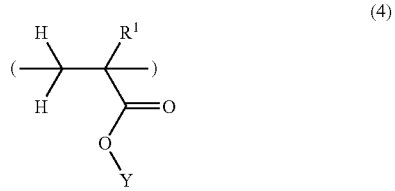

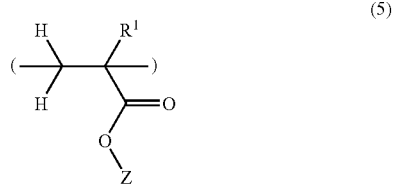

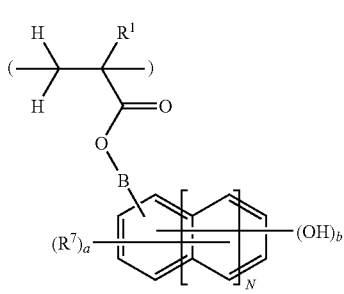

(6)

Herein $R^1$ is as defined above, $R^5$ and $R^6$ are each independently a hydrogen atom or hydroxyl group, X is an acid labile group, Y is a lactone structure-containing substituent group, Z is hydrogen, a $C_1$-$C_{15}$ fluoroalkyl group or a $C_1$-$C_{15}$ fluoroalcohol-containing substituent group, N is an integer of 0 to 2, $R^7$ is a hydrogen atom or $C_1$-$C_{10}$ alkyl group, B is a single bond or a divalent $C_1$-$C_{10}$ hydrocarbon group which may have oxygen substituted thereon, a is an integer of 0 to 3, and b is an integer of 1 to 3.

Under the action of an acid, a polymer comprising recurring units of formula (2) is decomposed to generate a carboxylic acid and turns into an alkali-soluble polymer.

The acid labile group represented by X may be selected from a variety of such groups, for example, groups of the following general formulae (L1) to (L4) and (L2-2), tertiary alkyl groups of 4 to 20 carbon atoms, preferably 4 to 15 carbon atoms, trialkylsilyl groups in which each alkyl moiety has 1 to 6 carbon atoms, and oxoalkyl groups of 4 to 20 carbon atoms.

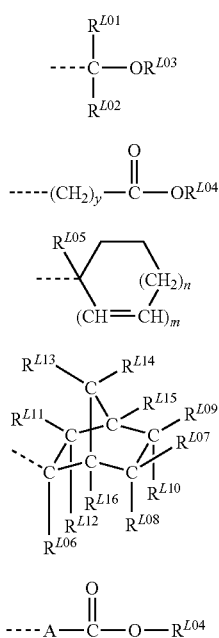

The broken line indicates a valence bond.

In formula (L1), $R^{L01}$ and $R^{L02}$ are hydrogen or straight, branched or cyclic alkyl groups of 1 to 18 carbon atoms, preferably 1 to 10 carbon atoms. Examples include hydrogen, methyl, ethyl, propyl, isopropyl, n-butyl, sec-butyl, tert-butyl, cyclopentyl, cyclohexyl, 2-ethylhexyl, n-octyl, norbornyl, tricyclodecanyl, tetracyclododecanyl, and adamantyl.

$R^{L03}$ is a monovalent hydrocarbon group of 1 to 18 carbon atoms, preferably 1 to 10 carbon atoms, which may contain a hetero atom such as oxygen, examples of which include straight, branched or cyclic alkyl groups and substituted forms of these groups in which some hydrogen atoms are replaced by hydroxyl, alkoxy, oxo, amino, alkylamino or the like. Examples of the substituted alkyl groups are shown below.

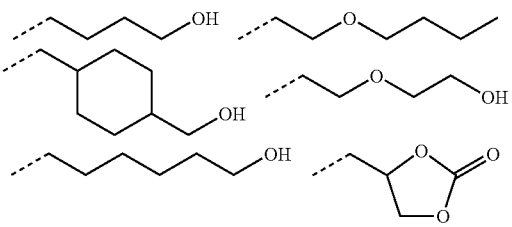

A pair of $R^{L01}$ and $R^{L02}$, $R^{L01}$ and $R^{L03}$, or $R^{L02}$ and $R^{L03}$ may bond together to form a ring with the carbon and oxygen atoms to which they are attached. Each of $R^{L01}$, $R^{L02}$ and $R^{L03}$ is a straight or branched alkylene group of 1 to 18 carbon atoms, preferably 1 to 10 carbon atoms when they form a ring.

In formula (L2), $R^{L04}$ is a tertiary alkyl group of 4 to 20 carbon atoms, preferably 4 to 15 carbon atoms, a trialkylsilyl group in which each alkyl moiety has 1 to 6 carbon atoms, an oxoalkyl group of 4 to 20 carbon atoms, or a group of formula (L1). Exemplary tertiary alkyl groups are tert-butyl, tert-amyl, 1,1-diethylpropyl, 2-cyclopentylpropan-2-yl, 2-cyclohexylpropan-2-yl, 2-(bicyclo[2.2.1]heptan-2-yl)propan-2-yl, 2-(adamantan-1-yl)propan-2-yl, 1-ethylcyclopentyl, 1-butylcyclopentyl, 1-ethylcyclohexyl, 1-butylcyclohexyl, 1-ethyl-2-cyclopentenyl, 1-ethyl-2-cyclohexenyl, 2-methyl-2-adamantyl, and 2-ethyl-2-adamantyl. Exemplary trialkylsilyl groups are trimethylsilyl, triethylsilyl, and dimethyl-tert-butylsilyl. Exemplary oxoalkyl groups are 3-oxocyclohexyl, 4-methyl-2-oxooxan-4-yl, and 5-methyl-2-oxooxolan-5-yl. In formula (L2), y is an integer of 0 to 6.

In formula (L2-2), $R^{L04}$ is as defined above, and examples of the moiety of the formula:

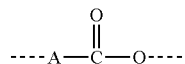

are given below.

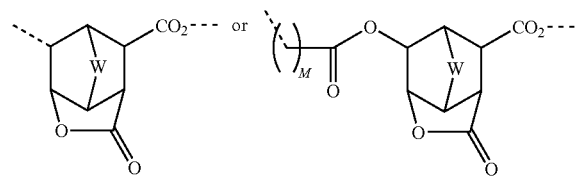

Herein W is an oxygen atom or $CH_2$, and M is an integer of 1 to 3.

In formula (L3), $R^{L05}$ is a substituted or unsubstituted, $C_1$-$C_8$ straight, branched or cyclic alkyl group or a substituted or unsubstituted $C_6$-$C_{20}$ aryl group. Examples of the substituted or unsubstituted alkyl groups include straight, branched or cyclic ones such as methyl, ethyl, propyl, isopropyl, n-butyl, sec-butyl, tert-butyl, tert-amyl, n-pentyl, n-hexyl, cyclopentyl and cyclohexyl; and of the foregoing in which some hydrogen atoms are replaced by hydroxyl, alkoxy, carboxy, alkoxycarbonyl, oxo, amino, alkylamino, cyano, mercapto, alkylthio, sulfo or other groups. Exemplary substituted or unsubstituted aryl groups are phenyl, methylphenyl, naphthyl, anthryl, phenanthryl, and pyrenyl. In formula (L3), m is 0 or 1, n is 0, 1, 2 or 3, and 2 m+n is equal to 2 or 3.

In formula (L4), $R^{L06}$ is a substituted or unsubstituted, $C_1$-$C_8$ straight, branched or cyclic alkyl group or a substituted or unsubstituted $C_6$-$C_{20}$ aryl group. Examples of these groups are the same as exemplified for $R^{L05}$. $R^{L07}$ to $R^{L16}$ independently represent hydrogen or monovalent $C_1$-$C_{15}$ hydrocarbon groups. Exemplary hydrocarbon groups are straight, branched or cyclic alkyl groups such as methyl, ethyl, propyl, isopropyl, n-butyl, sec-butyl, tert-butyl, tert-amyl, n-pentyl, n-hexyl, n-octyl, n-nonyl, n-decyl, cyclopentyl, cyclohexyl, cyclopentylmethyl, cyclopentylethyl, cyclopentylbutyl, cyclohexylmethyl, cyclohexylethyl and cyclohexylbutyl, and substituted forms of the foregoing in which some hydrogen atoms are replaced by hydroxyl, alkoxy, carboxy, alkoxycarbonyl, oxo, amino, alkylamino, cyano, mercapto, alkylthio, sulfo or other groups. Alternatively, two of $R^{L07}$ to $R^{L16}$ may bond together to form a ring with the carbon atom to which they are attached (for example, a pair of $R^{L07}$ and $R^{L08}$, $R^{L07}$ and $R^{L09}$, $R^{L08}$ and $R^{L10}$, $R^{L09}$ and $R^{L10}$, $R^{L11}$ and $R^{L12}$, $R^{L13}$ and $R^{L14}$, or a similar pair form a ring). Each of $R^{L07}$ to $R^{L16}$ represents a divalent $C_1$-$C_{15}$ hydrocarbon group when they form a ring, examples of which are the ones exemplified above for the monovalent hydrocarbon groups, with one hydrogen atom being eliminated. Two of $R^{L07}$ to $R^{L16}$ which are attached to vicinal carbon atoms may bond together directly to form a double bond (for example, a pair of $R^{L07}$ and $R^{L09}$, $R^{L09}$ and $R^{L15}$, $R^{L13}$ and $R^{L15}$, or a similar pair).

Of the acid labile groups of formula (L1), the straight and branched ones are exemplified by the following groups.

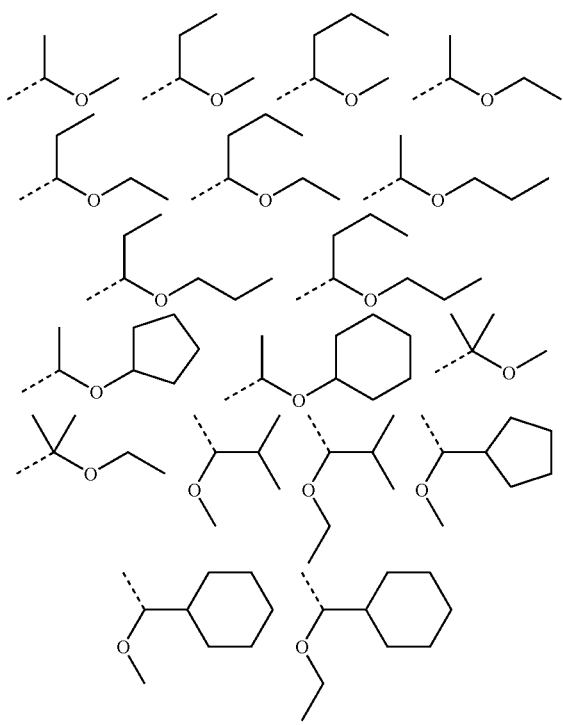

Of the acid labile groups of formula (L1), the cyclic ones are, for example, tetrahydrofuran-2-yl, 2-methyltetrahydrofuran-2-yl, tetrahydropyran-2-yl, and 2-methyltetrahydropyran-2-yl.

Examples of the acid labile groups of formula (L2) include tert-butoxycarbonyl, tert-butoxycarbonylmethyl, tert-amyloxycarbonyl, tert-amyloxycarbonylmethyl, 1,1-diethylpropyloxycarbonyl, 1,1-diethylpropyloxycarbonylmethyl, 1-ethylcyclopentyloxycarbonyl, 1-ethylcyclopentyloxycarbonylmethyl, 1-ethyl-2-cyclopentenyloxycarbonyl, 1-ethyl-2-cyclopentenyloxycarbonylmethyl, 1-ethoxyethoxycarbonylmethyl, 2-tetrahydropyranyloxycarbonylmethyl, and 2-tetrahydrofuranyloxycarbonylmethyl groups.

Examples of the acid labile groups of formula (L2-2) include 9-(tert-butyloxycarbonyl)-5-oxo-4-oxatricyclo[4.2.1.0$^{3,7}$]-nonan-2-yl, 9-(tert-amyloxycarbonyl)-5-oxo-4-oxatricyclo[4.2.1.0$^{3,7}$]nonan-2-yl, 9-(2-(adamantan-1-yl)propan-2-yloxycarbonyl)-5-oxo-4-oxa-tricyclo[4.2.1.0$^{3,7}$]nonan-2-yl, 9-(1-ethylcyclopentyloxycarbonyl)-5-oxo-4-oxatricyclo-[4.2.1.0$^{3,7}$]nonan-2-yl, 9-(1-butylcyclopentyloxycarbonyl)-5-oxo-4-oxatricyclo-[4.2.1.0$^{3,7}$]nonan-2-yl, 9-(1-ethylcyclohexyloxycarbonyl)-5-oxo-4-oxatricyclo-[4.2.1.0$^{3,7}$]nonan-2-yl, 9-(1-butylcyclohexyloxycarbonyl)-5-oxo-4-oxatricyclo-[4.2.1.0$^{3,7}$]nonan-2-yl, 9-(2-methyl-2-adamantyloxycarbonyl)-5-oxo-4-oxatricyclo-[4.2.1.0$^{3,7}$]nonan-2-yl, 9-(2-ethyl-2-adamantyloxycarbonyl)-5-oxo-4-oxatricyclo-[4.2.1.0$^{3,7}$]nonan-2-yl, 9-(4-ethyltetracyclo[6.2.1.1$^{3,6}$.0$^{2,7}$]dodecan-4-yloxycarbonyl)-5-oxo-4-oxatricyclo[4.2.1.0$^{3,7}$]nonan-2-yl, 2-(9-(tert-butyloxycarbonyl)-5-oxo-4-oxatricyclo[4.2.1.0$^{3,7}$]-nonan-2-yloxy)-2-oxoethyl, 2-(9-(tert-amyloxycarbonyl)-5-oxo-4-oxatricyclo[4.2.1.0$^{3,7}$]-nonan-2-yloxy)-2-oxoethyl, 2-(9-(2-(adamantan-1-yl)propan-2-yloxycarbonyl)-5-oxo-4-oxa-tricyclo[4.2.1.0$^{3,7}$]nonan-2-yloxy)-2-oxoethyl, 2-(9-(1-ethylcyclopentyloxycarbonyl)-5-oxo-4-oxatricyclo-[4.2.1.0$^{3,7}$]nonan-2-yloxy)-2-oxoethyl, 2-(9-(1-butylcyclopentyloxycarbonyl)-5-oxo-4-oxatricyclo-[4.2.1.0$^{3,7}$]nonan-2-yloxy)-2-oxoethyl, 2-(9-(1-ethylcyclohexyloxycarbonyl)-5-oxo-4-oxatricyclo-[4.2.1.0$^{3,7}$]nonan-2-yloxy)-2-oxoethyl, 2-(9-(1-butylcyclohexyloxycarbonyl)-5-oxo-4-oxatricyclo-[4.2.1.0$^{3,7}$]nonan-2-yloxy)-2-oxoethyl, 2-(9-(2-methyl-2-adamantyloxycarbonyl)-5-oxo-4-oxatricyclo-[4.2.1.0$^{3,7}$]nonan-2-yloxy)-2-oxoethyl, 2-(9-(2-ethyl-2-adamantyloxycarbonyl)-5-oxo-4-oxatricyclo-[4.2.1.0$^{3,7}$]nonan-2-yloxy)-2-oxoethyl, 2-(9-(4-ethyltetracyclo[6.2.1.1$^{3,6}$.0$^{2,7}$]dodecan-4-yloxy-carbonyl)-5-oxo-4-oxatricyclo[4.2.1.0$^{3,7}$]nonan-2-yloxy)-2-oxoethyl, 4-(9-(tert-butyloxycarbonyl)-5-oxo-4-oxatricyclo[4.2.1.0$^{3,7}$]-nonan-2-yloxy)-4-oxobutyl, 4-(9-(tert-amyloxycarbonyl)-5-oxo-4-oxatricyclo[4.2.1.0$^{3,7}$]-nonan-2-yloxy)-4-oxobutyl, 4-(9-(2-(admantan-1-yl)propan-2-yloxycarbonyl)-5-oxo-4-oxa-tricyclo[4.2.1.0$^{3,7}$]nonan-2-yloxy)-4-oxobutyl, 4-(9-(1-ethylcyclopentyloxycarbonyl)-5-oxo-4-oxatricyclo-[4.2.1.0$^{3,7}$]nonan-2-yloxy)-4-oxobutyl, 4-(9-(1-butylcyclopentyloxycarbonyl)-5-oxo-4-oxatricyclo-[4.2.1.0$^{3,7}$]nonan-2-yloxy)-4-oxobutyl, 4-(9-(1-ethylcyclohexyloxycarbonyl)-5-oxo-4-oxatricyclo-[4.2.1.0$^{3,}$ 7]nonan-2-yloxy)-4-oxobutyl, 4-(9-(1-butylcyclohexyloxycarbonyl)-5-oxo-4-oxatricyclo-[4.2.1.0$^{3,7}$]nonan-2-yloxy)-4-oxobutyl, 4-(9-(2-methyl-2-adamantyloxycarbonyl)-5-oxo-4-oxatricyclo-[4.2.1.0$^{3,7}$]nonan-2-yloxy)-4-oxobutyl, 4-(9-(2-ethyl-2-adamantyloxycarbonyl)-5-oxo-4-oxatricyclo-[4.2.1.0$^{3,7}$]nonan-2-yloxy)-4-oxobutyl, 4-(9-(4-ethyltetracyclo [6.2.1.1$^{3,6}$.0$^{2,7}$]dodecan-4-yloxy-carbonyl)-5-oxo-4-oxatricyclo[4.2.1.0$^{3,7}$]nonan-2-yloxy)-4-oxobutyl, etc.

Examples of the acid labile groups of formula (L3) include 1-methylcyclopentyl, 1-ethylcyclopentyl, 1-n-propylcyclopentyl, 1-isopropylcyclopentyl, 1-n-butylcyclopentyl, 1-sec-butylcyclopentyl, 1-cyclohexylcyclopentyl, 1-(4-methoxy-n-butyl)cyclopentyl, 1-methylcyclohexyl, 1-ethylcyclohexyl, 3-methyl-1-cyclopenten-3-yl, 3-ethyl-1-cyclopenten-3-yl, 3-methyl-1-cyclohexen-3-yl, and 3-ethyl-1-cyclohexen-3-yl.

Of the acid labile groups of formula (L4), those groups of the following formulae (L4-1) to (L4-4) are more preferred.

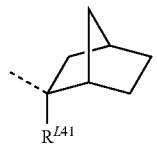
(L4-1)

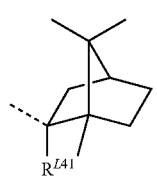
(L4-2)

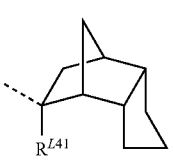
(L4-3)

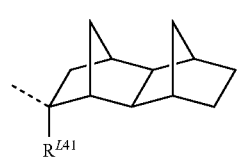
(L4-4)

In formulae (L4-1) to (L4-4), the broken line denotes a bonding site and direction. $R^{L41}$ is each independently selected from monovalent hydrocarbon groups, typically straight, branched or cyclic $C_1$-$C_{10}$ alkyl groups, for example, methyl, ethyl, propyl, isopropyl, n-butyl, sec-butyl, tert-butyl, tert-amyl, n-pentyl, n-hexyl, cyclopentyl, and cyclohexyl.

For formulas (L4-1) to (L4-4), there can exist enantiomers and diastereomers. Each of formulae (L4-1) to (L4-4) collectively represents all such stereoisomers. Such stereoisomers may be used alone or in admixture.

For example, the general formula (L4-3) represents one or a mixture of two selected from groups having the following general formulas (L4-3-1) and (L4-3-2).

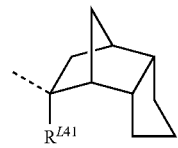
(L4-3-1)

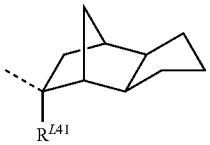
(L4-3-2)

Similarly, the general formula (L4-4) represents one or a mixture of two or more selected from groups having the following general formulas (L4-4-1) to (L4-4-4).

(L4-4-1)

(L4-4-2)

(L4-4-3)

(L4-4-4)

Each of formulas (L4-1) to (L4-4), (L4-3-1) and (L4-3-2), and (L4-4-1) to (L4-4-4) collectively represents an enantiomer thereof and a mixture of enantiomers.

It is noted that in the above formulas (L4-1) to (L4-4), (L4-3-1) and (L4-3-2), and (L4-4-1) to (L4-4-4), the bond direction is on the exo side relative to the bicyclo[2.2.1] heptane ring, which ensures high reactivity for acid catalyzed elimination reaction (see JP-A 2000-336121). In preparing these monomers having a tertiary exo-alkyl group of bicyclo [2.2.1]heptane skeleton as a substituent group, there may be contained monomers substituted with an endo-alkyl group as represented by the following formulas (L4-1-endo) to (L4-4-endo). For good reactivity, an exo proportion of at least 50 mol % is preferred, with an exo proportion of at least 80 mol % being more preferred.

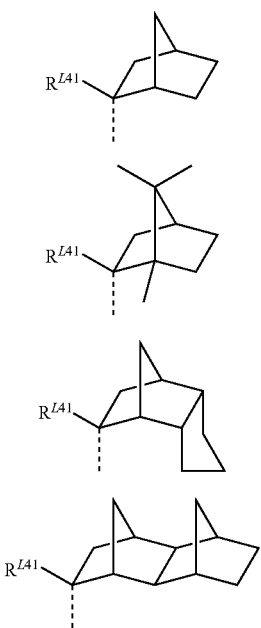

(L4-1-endo)
(L4-2-endo)
(L4-3-endo)
(L4-4-endo)

Illustrative examples of the acid labile group of formula (L4) are given below, but not limited thereto.

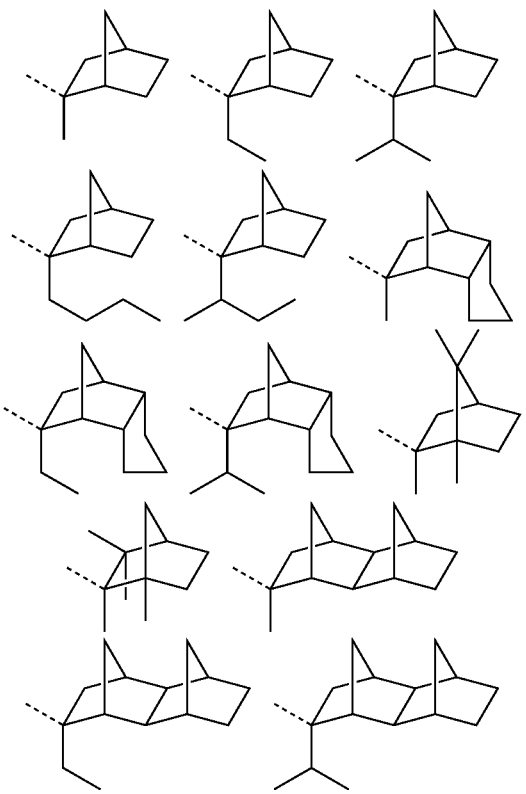

Examples of the tertiary $C_4$-$C_{20}$ alkyl, tri($C_1$-$C_6$-alkyl)silyl and $C_4$-$C_{20}$ oxoalkyl groups are as exemplified above for $R^{L04}$.

Illustrative, non-limiting examples of the recurring units of formula (2) are given below. Although only (meth)acrylates are illustrated, those which are separated by a divalent linking group of formula (L2) or (L2-2) are also useful.

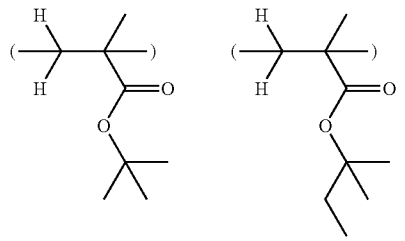
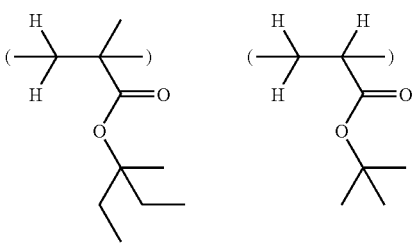
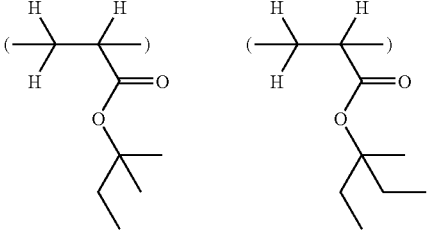
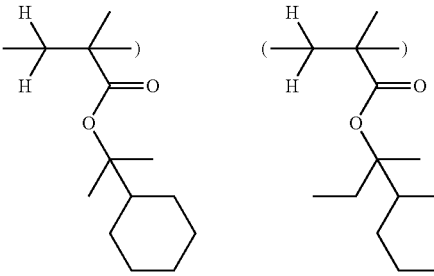
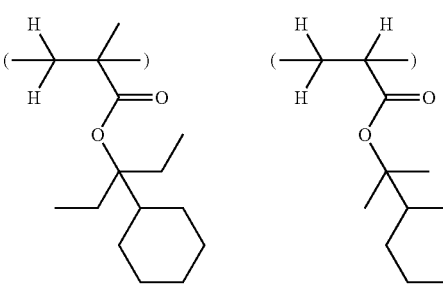
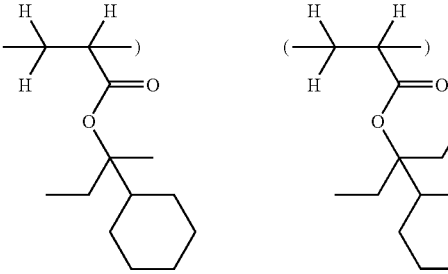

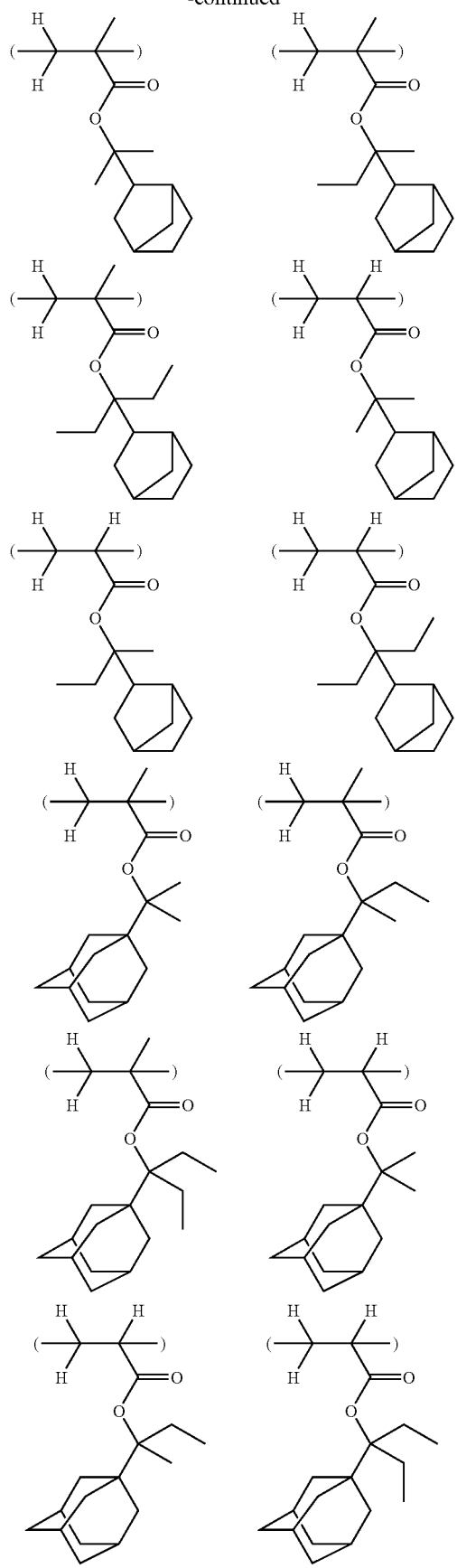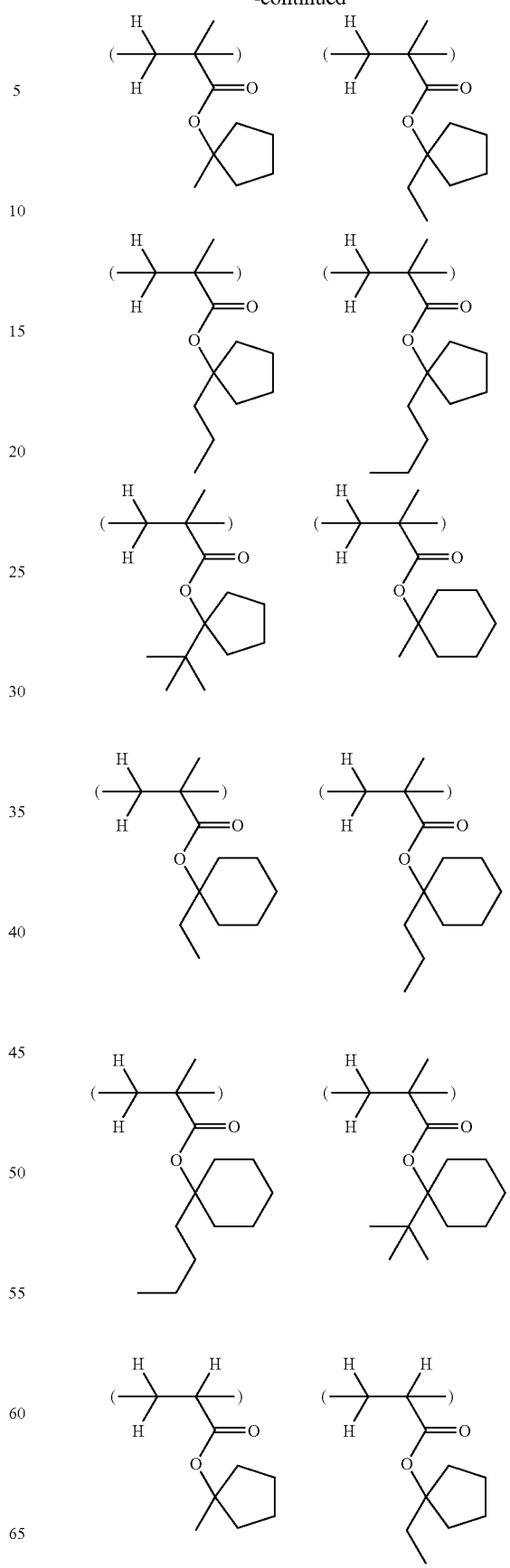

-continued
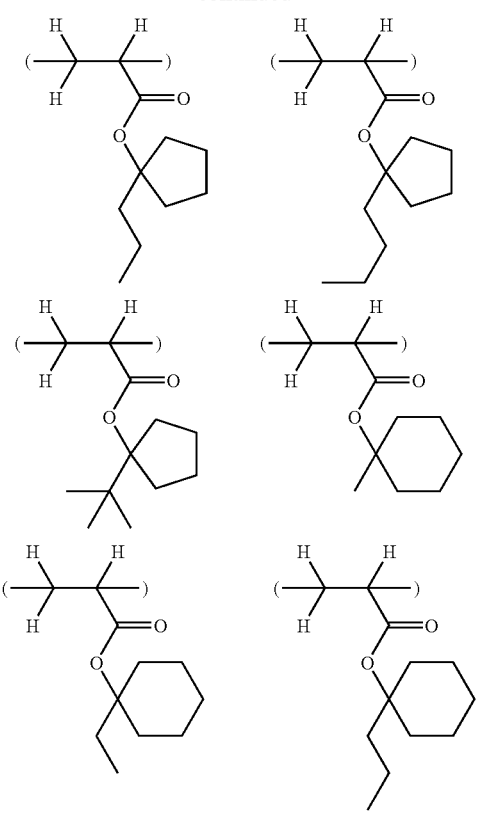
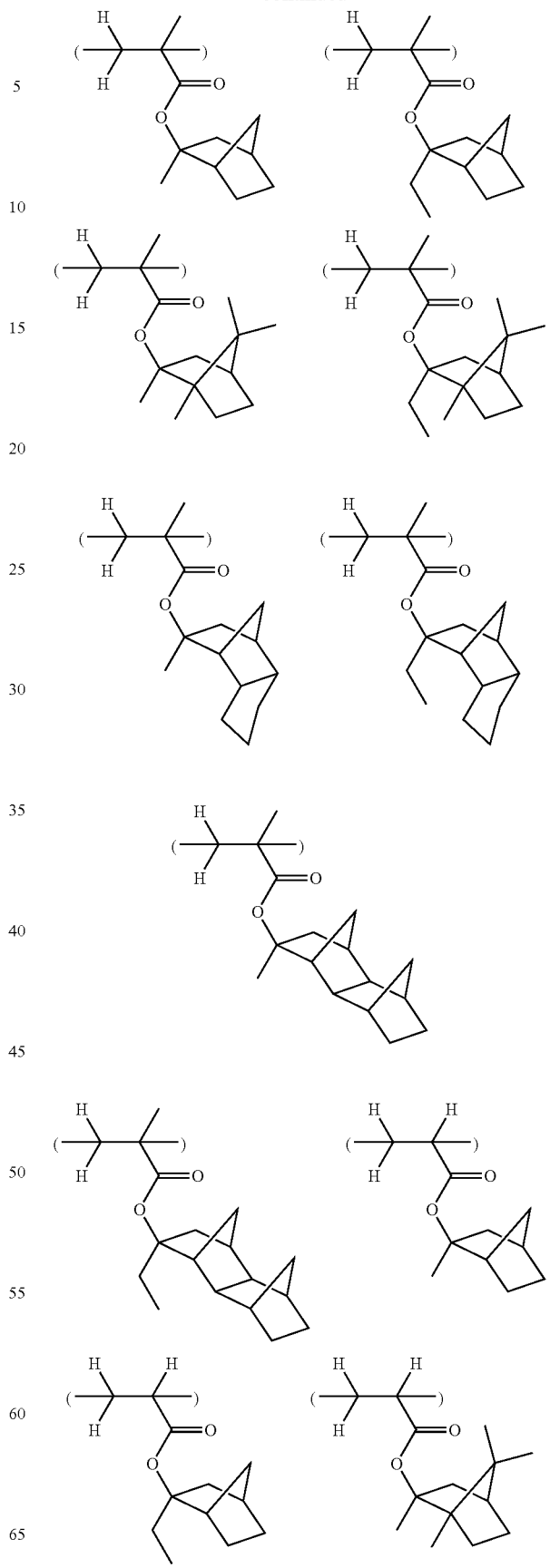

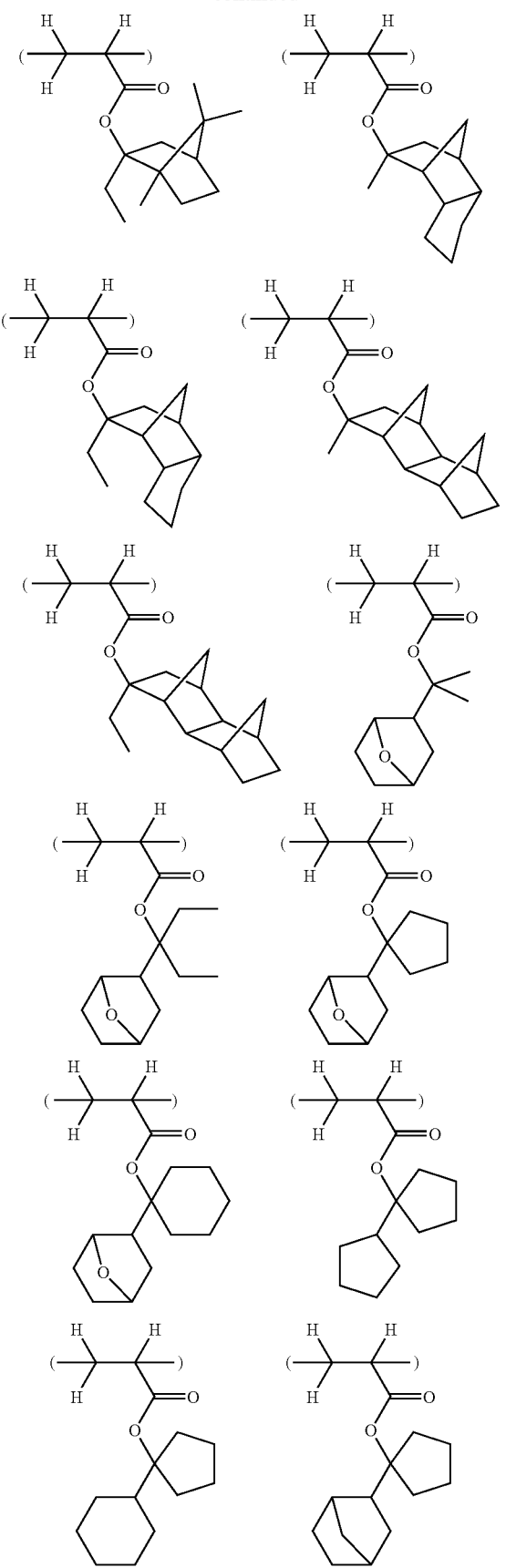
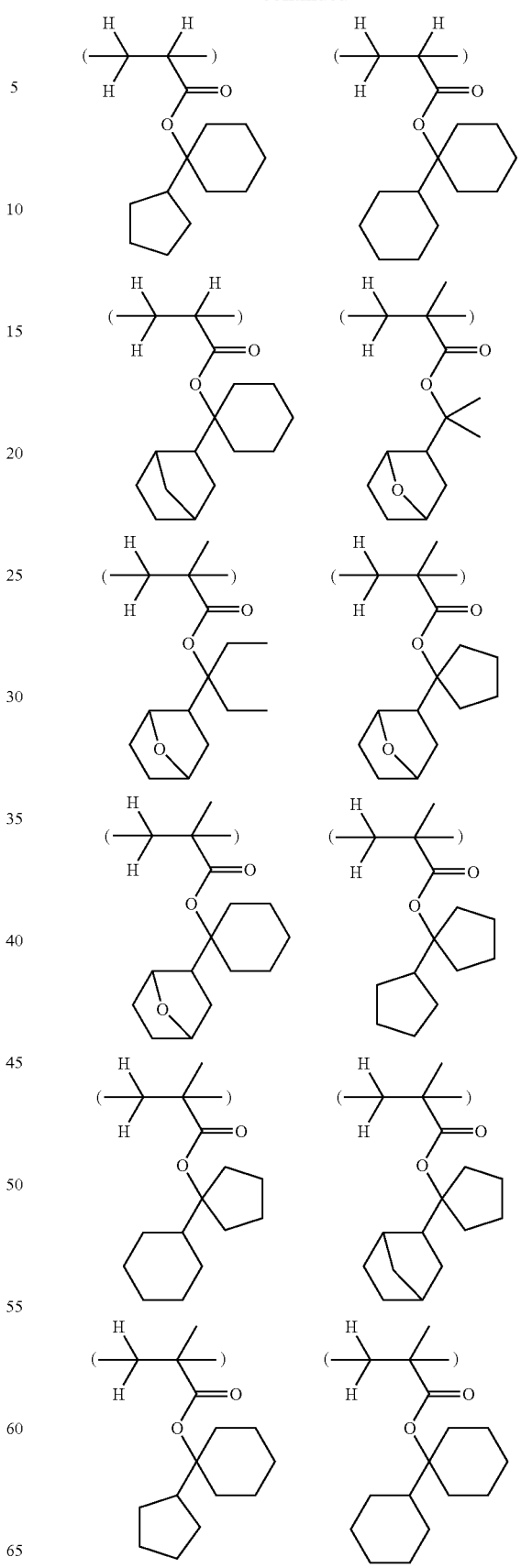

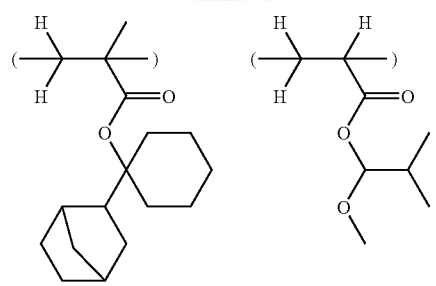
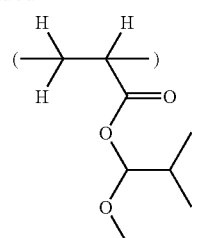
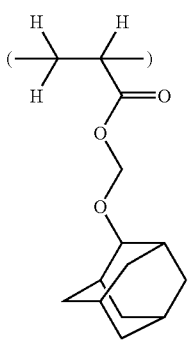
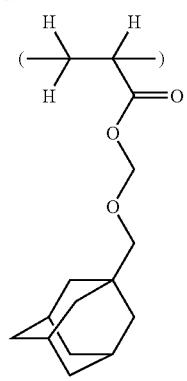
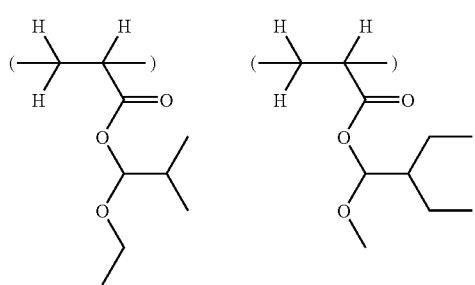
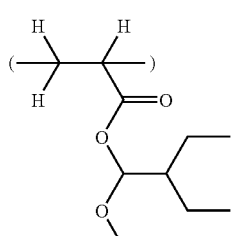
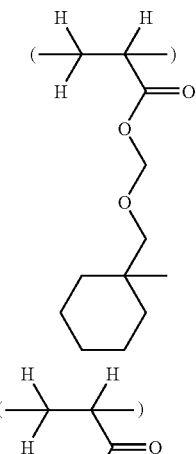
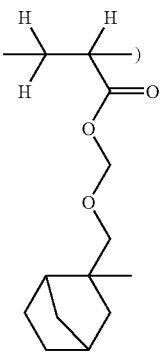
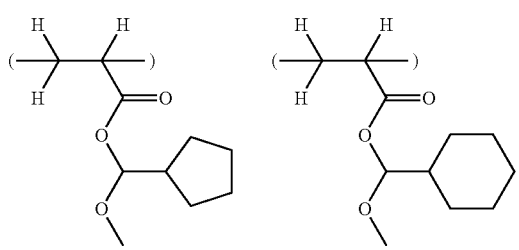
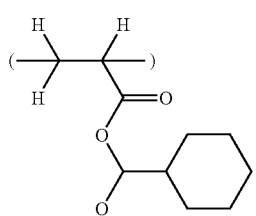
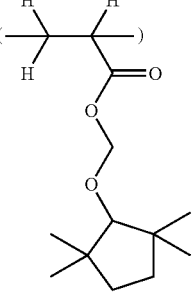
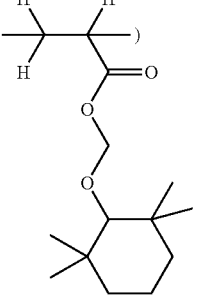
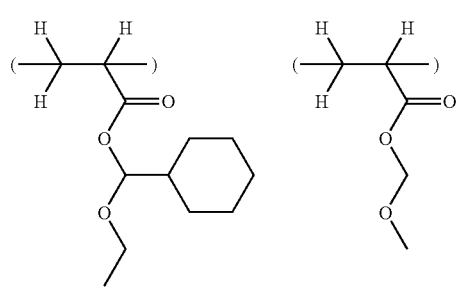
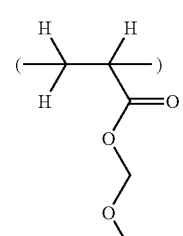
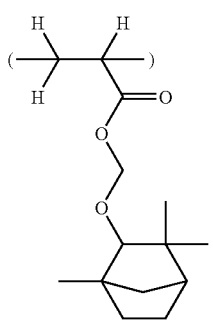
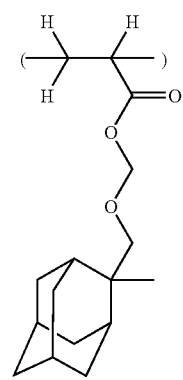
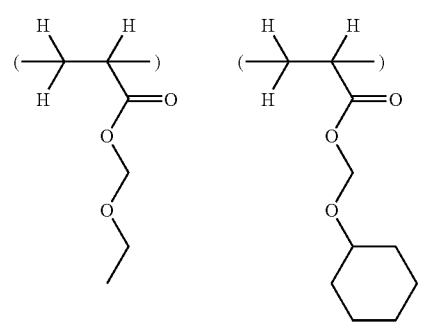
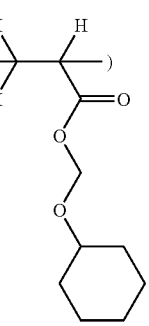
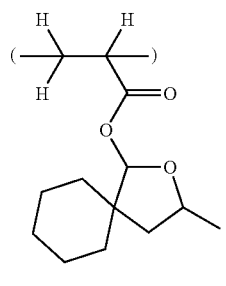
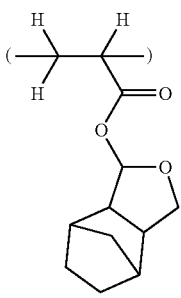

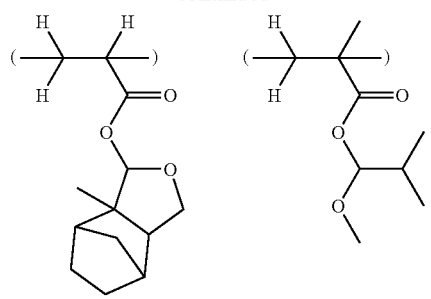
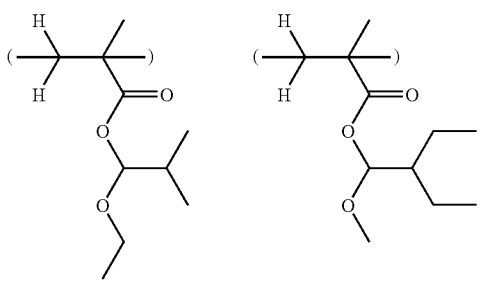
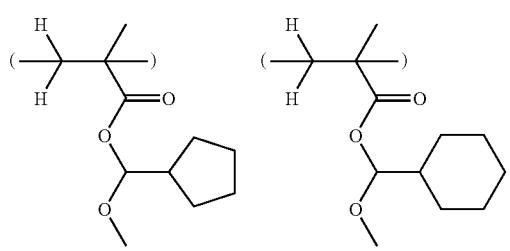
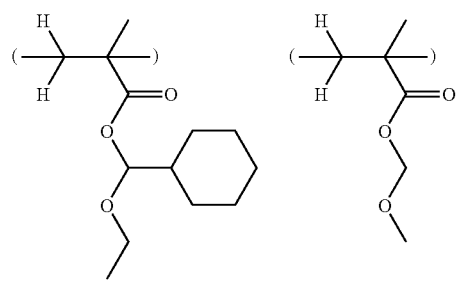
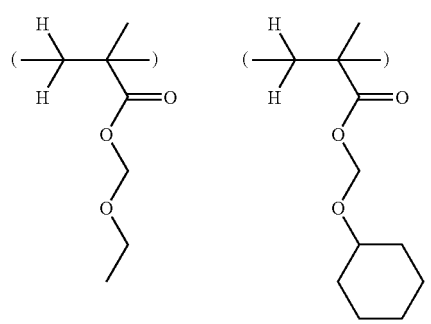
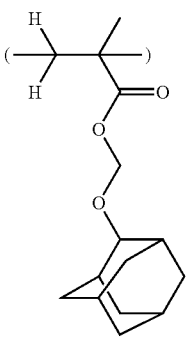
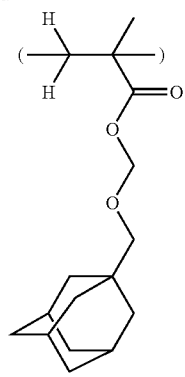
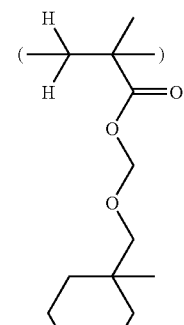
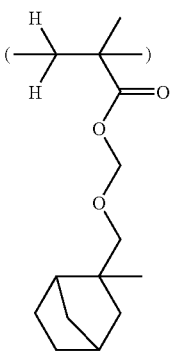
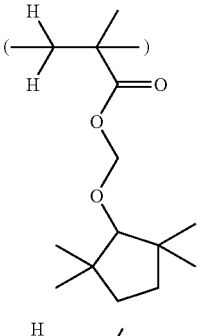
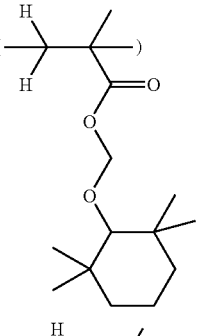
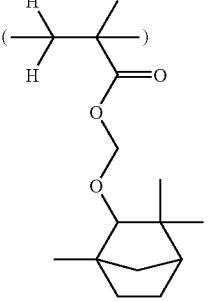
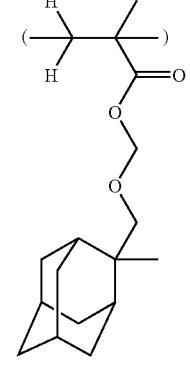
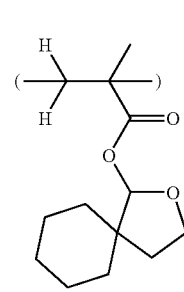
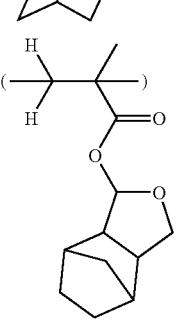

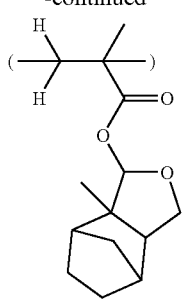

Illustrative, non-limiting examples of the recurring units of formula (3) are given below.

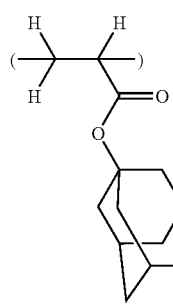 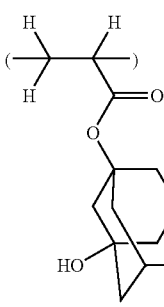

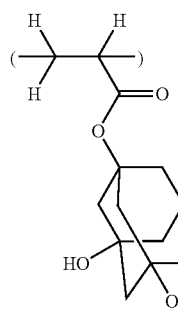 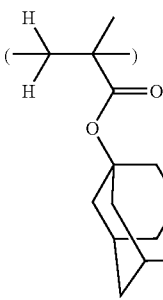

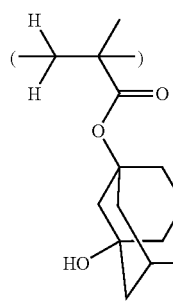 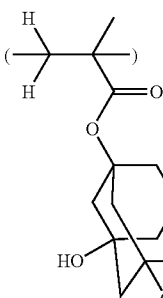

Illustrative examples of the recurring units of formula (4) are given below. Notably, recurring units having an acid labile group are also encompassed. Examples of such units overlap the examples of formula (L2-2) illustrated above as the acid labile group, and they may be used either as the lactone unit or as the acid labile group-containing unit.

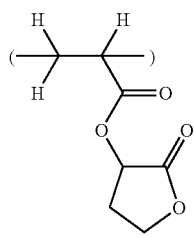 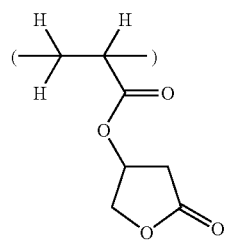

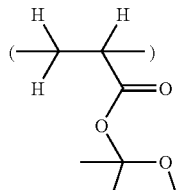 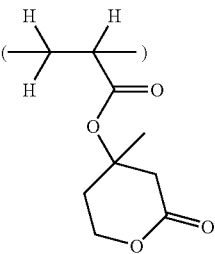

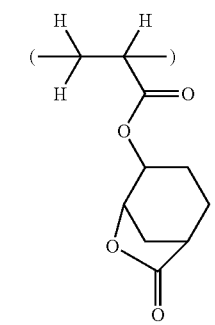 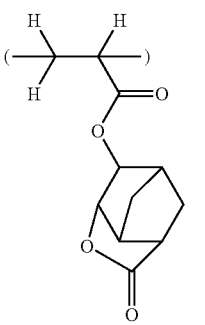

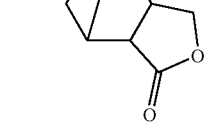 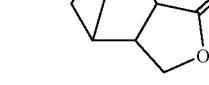

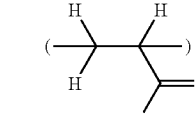 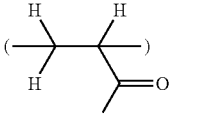

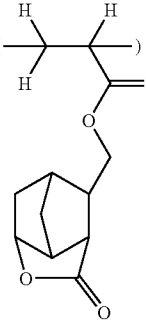 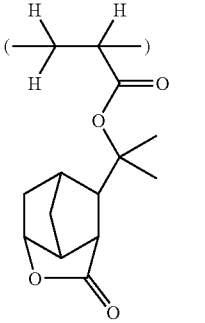

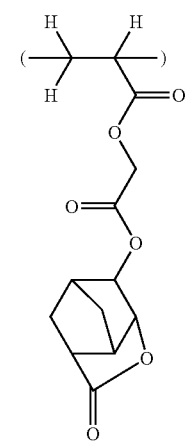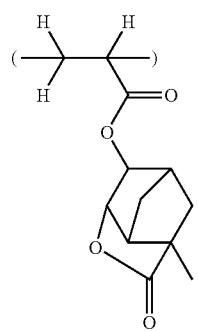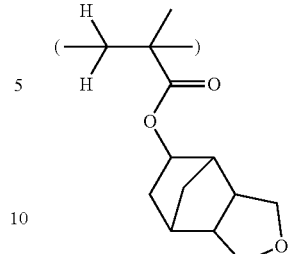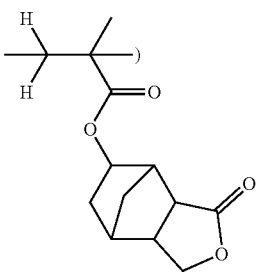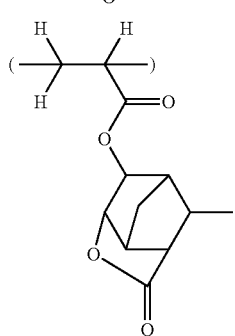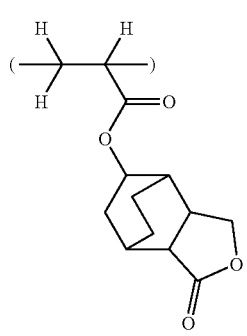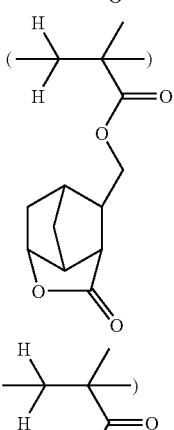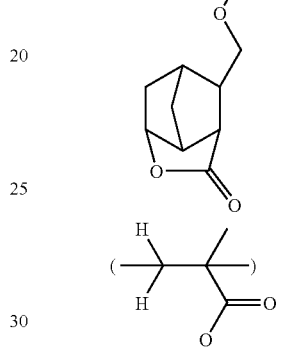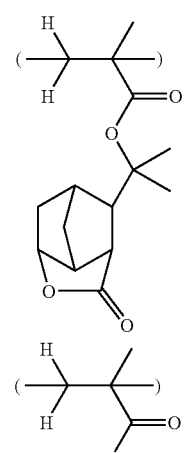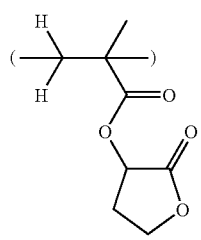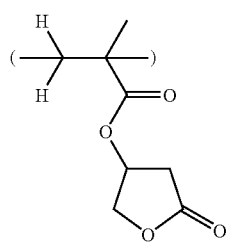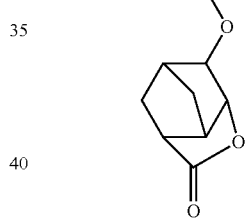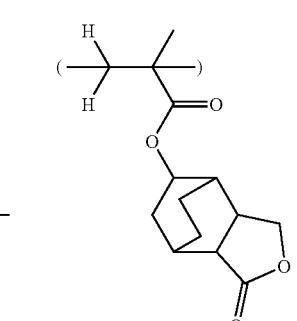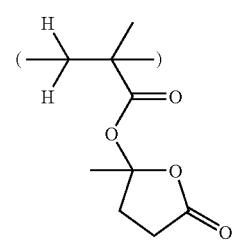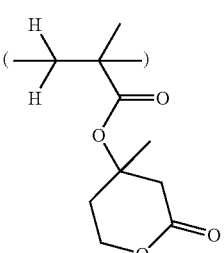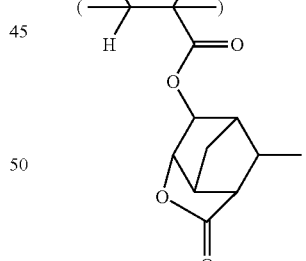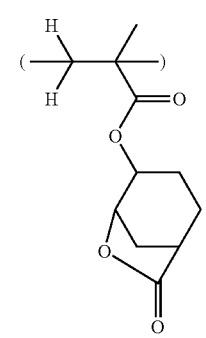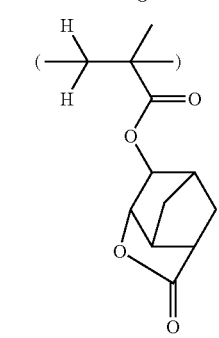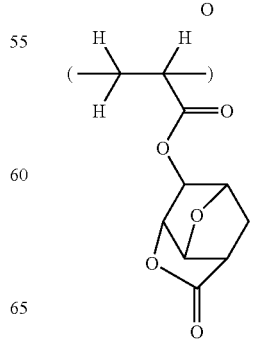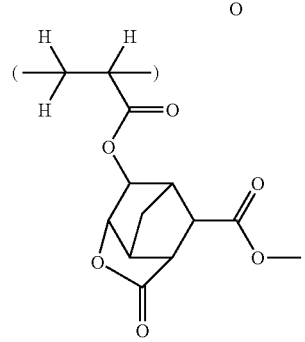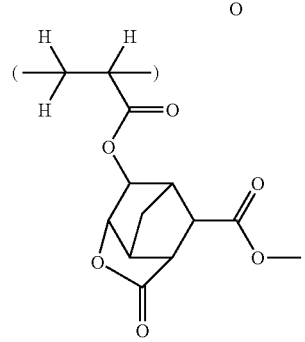

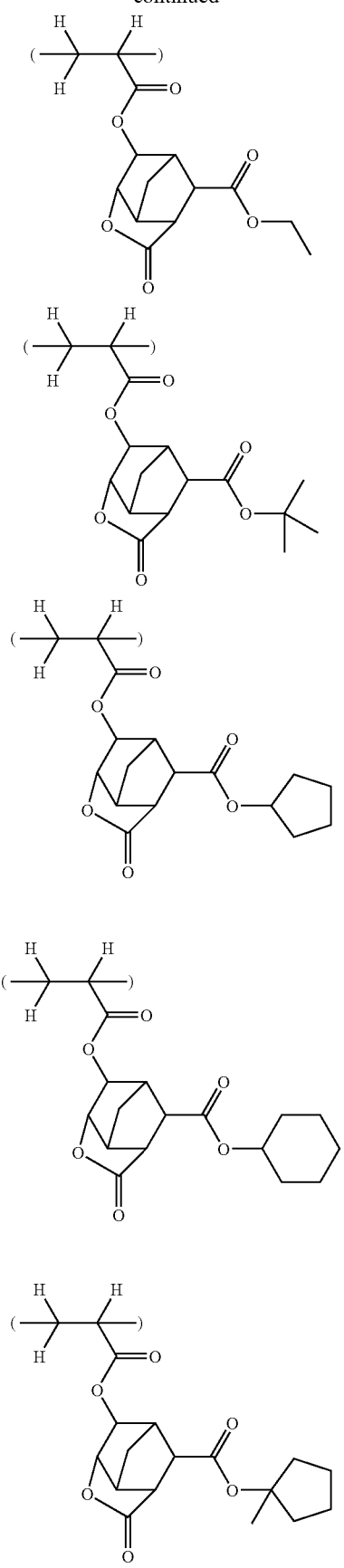
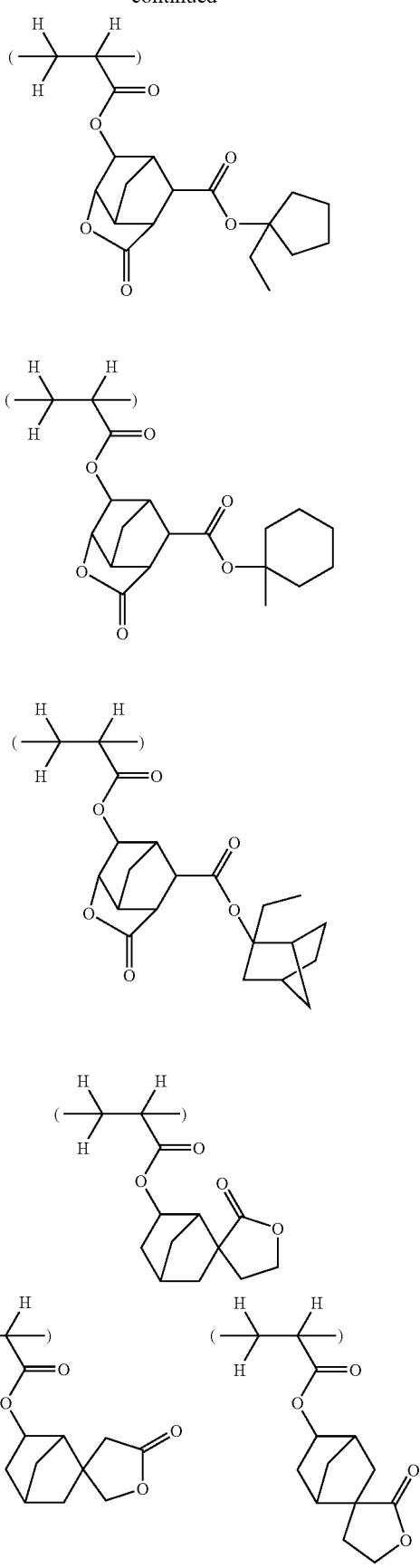

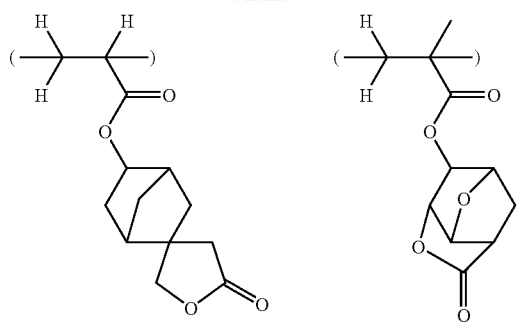
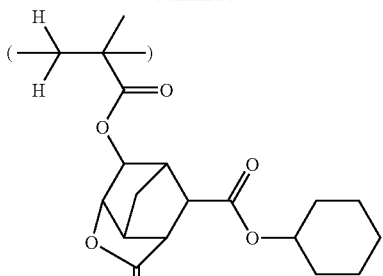
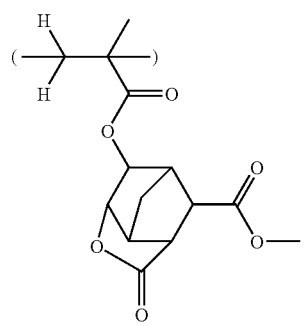
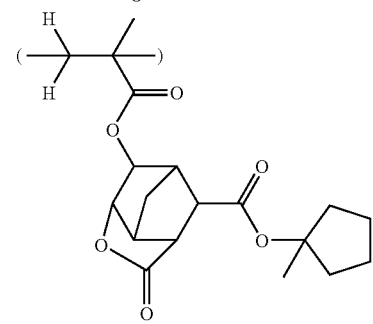
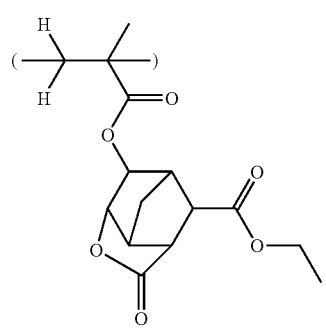
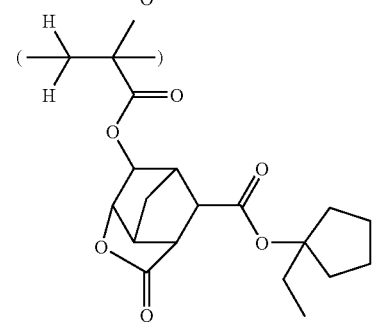
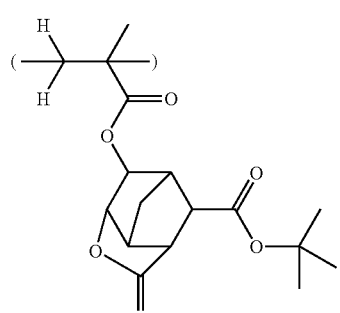
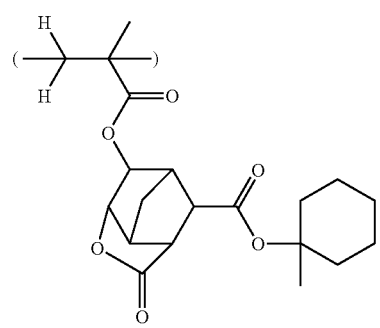
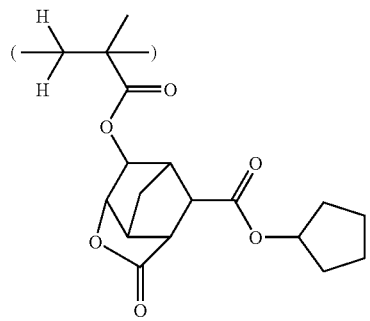
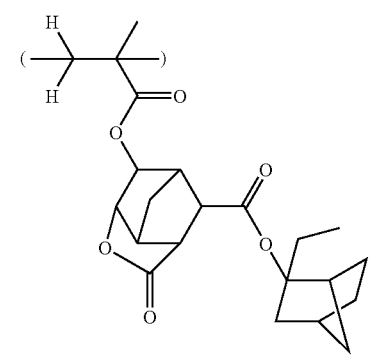

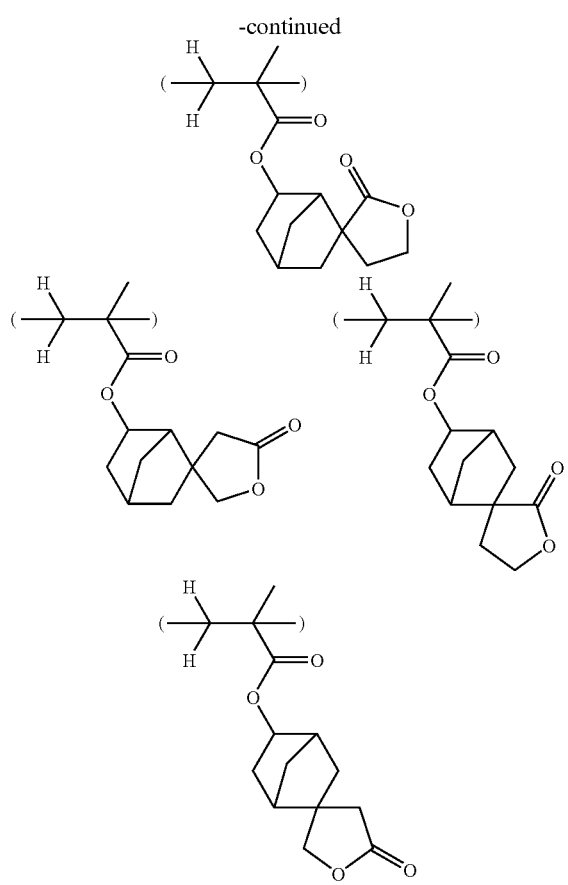

Also, units of the general formula (5L-1) may be advantageously used.

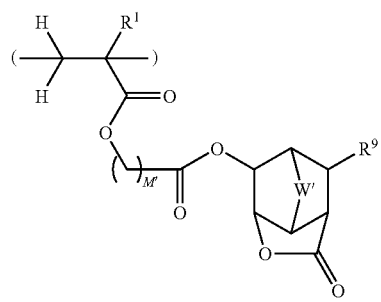

(5L-1)

In formula (5L-1), $R^1$ is hydrogen, fluorine, methyl or trifluoromethyl, and preferably methyl. $R^9$ is hydrogen or $CO_2R^{10}$ wherein $R^{10}$ is hydrogen, halogen or a straight, branched or cyclic $C_1$-$C_{15}$ monovalent hydrocarbon group which may have oxygen. W' is $CH_2$, O or S. M' is an integer of 1 to 3.

Examples of $R^{10}$ include hydrogen, methyl, ethyl, n-propyl, isopropyl, n-butyl, sec-butyl, isobutyl, tert-butyl, cyclopentyl, cyclohexyl, 1-methylcyclopentyl, 1-ethylcyclopentyl, 1-methylcyclohexyl, 1-ethylcyclohexyl, 2-ethylhexyl, n-octyl, 2-methylbicyclo[2.2.1]heptan-2-yl, 2-ethylbicyclo[2.2.1]heptan-2-yl, 2-methyladamantan-2-yl, 2-ethyladamantan-2-yl, 8-methyltricyclo[5.2.1.0$^{2,6}$]decan-8-yl, 8-ethyltricyclo[5.2.1.0$^{2,6}$]decan-8-yl, 4-methyltetracyclo[6.2.1.1$^{3,6}$.0$^{2,7}$]dodecan-4-yl, 4-ethyltetracyclo[6.2.1.1$^{3,6}$.0$^{2,7}$]dodecan-4-yl, methoxymethyl, ethoxymethyl, methoxyethyl, ethoxyethyl, and methoxyethoxyethyl, as well as the groups shown below.

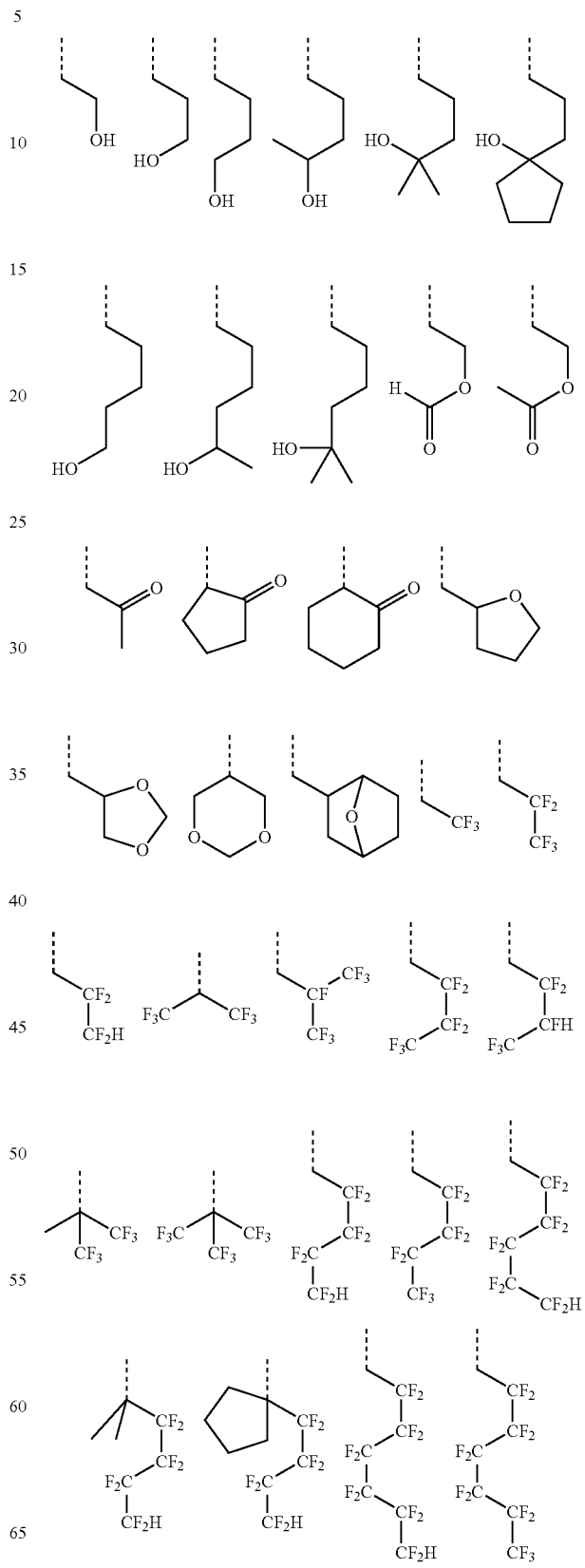

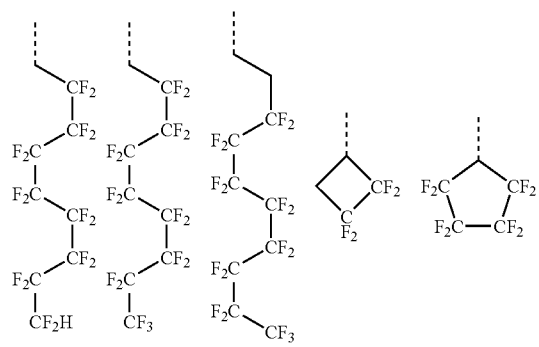

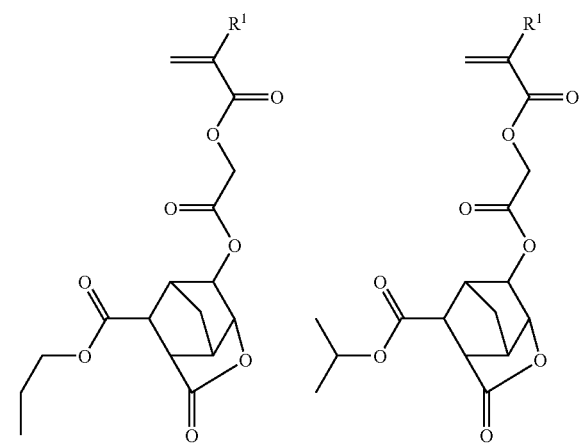

(The broken line denotes a valence bond.)

Preferred examples of $R^{10}$ include methyl, 1-methylcyclopentyl, 1-ethylcyclopentyl, 1-methylcyclohexyl, 1-ethylcyclohexyl, 2-methyladamantan-2-yl, 2-ethyladamantan-2-yl, 8-methyltricyclo[5.2.1.0$^{2,6}$]decan-8-yl, 8-ethyltricyclo[5.2.1.0$^{2,6}$]decan-8-yl, 4-ethyltetracyclo[6.2.1.1$^{3,6}$.0$^{2,7}$]dodecan-4-yl. Preferably W' is $CH_2$.

Examples of suitable monomers from which recurring units of formula (5L-1) are derived are given below.

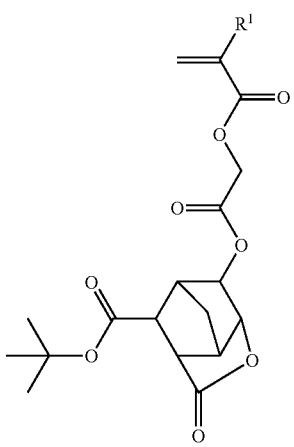

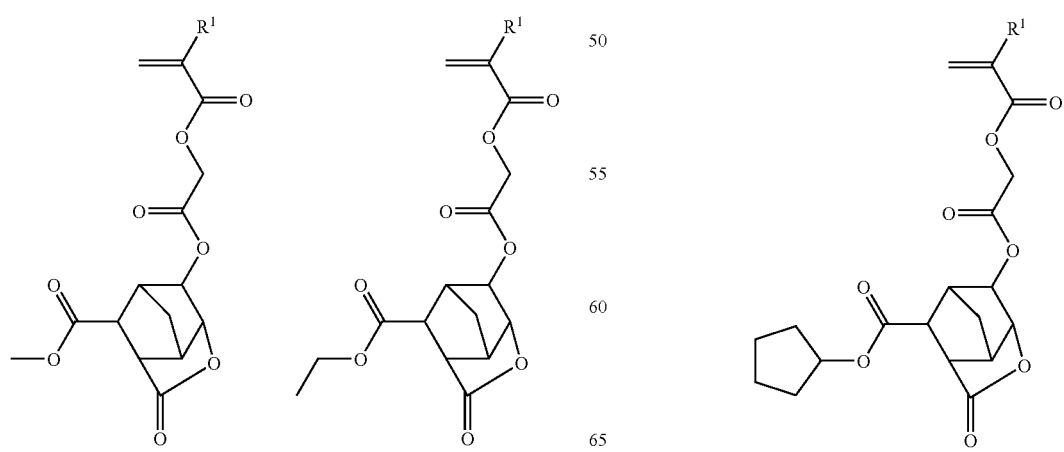

49
-continued
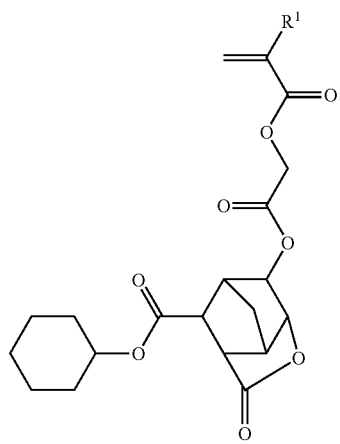
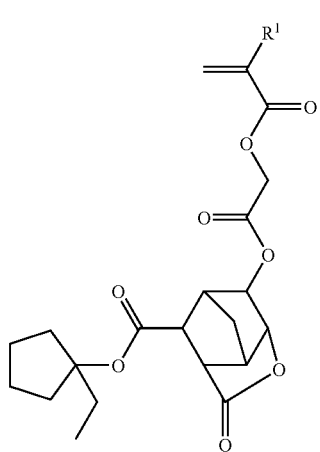
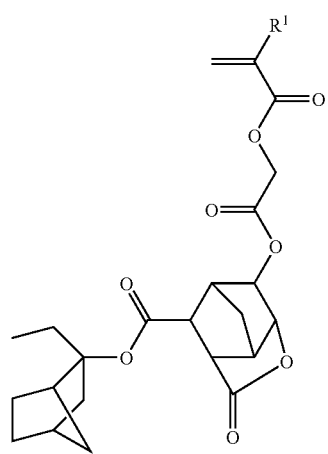
50
-continued
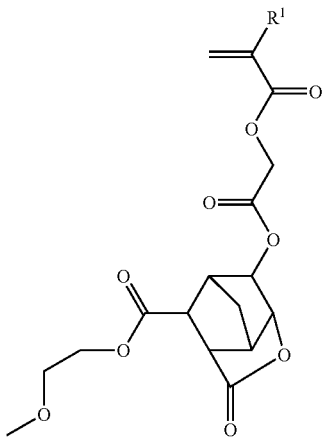
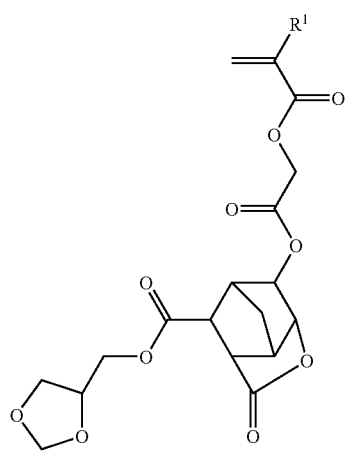
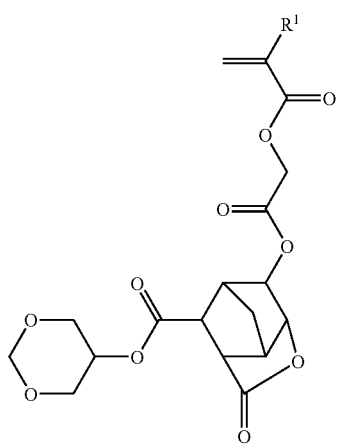

-continued
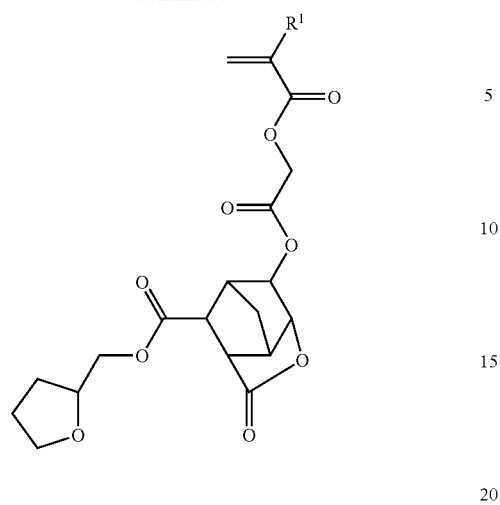
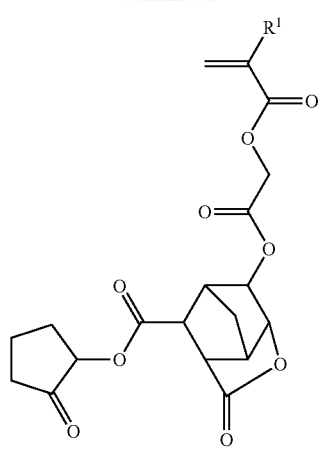
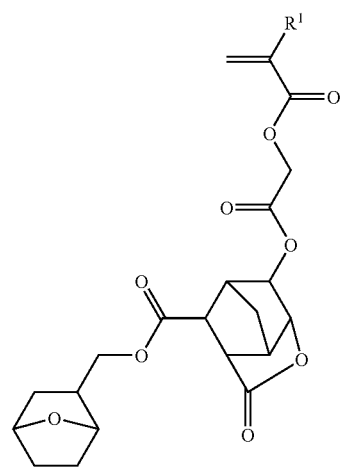
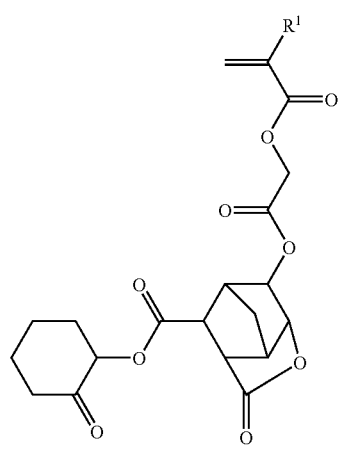
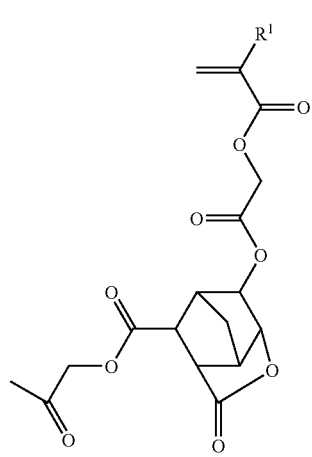
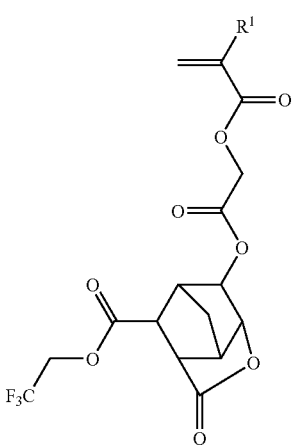

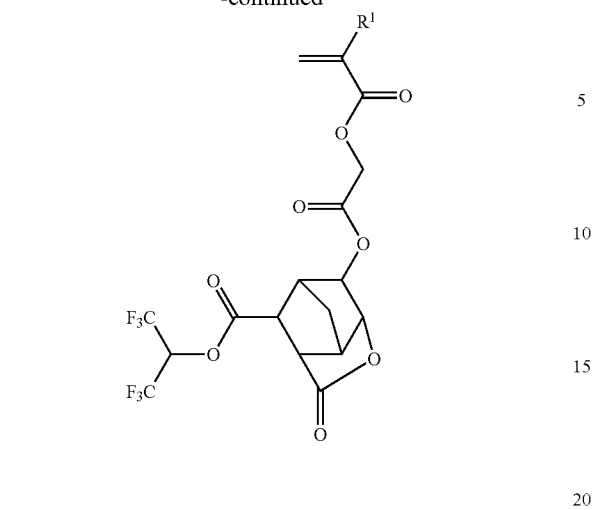
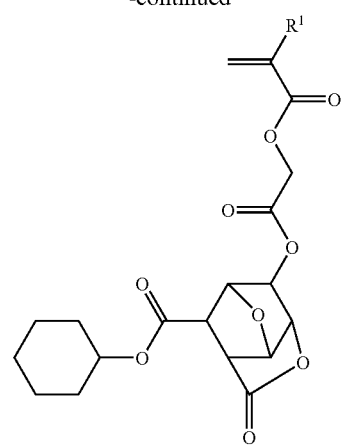
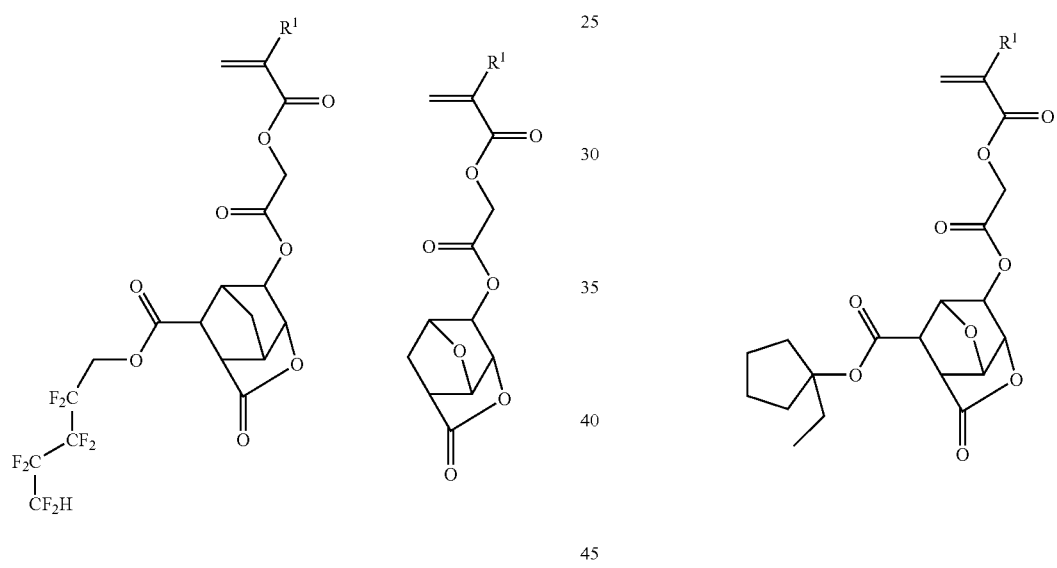
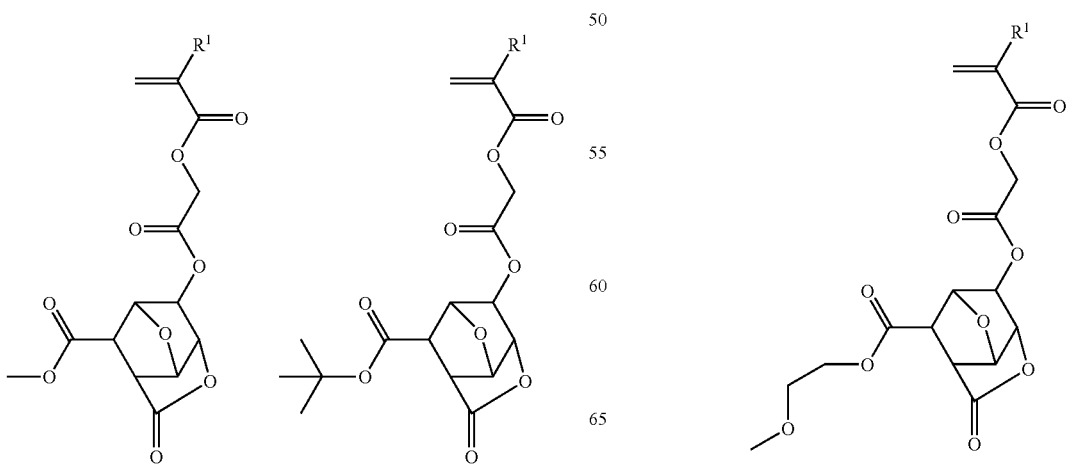

-continued
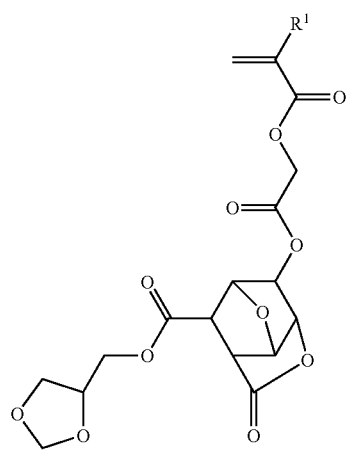
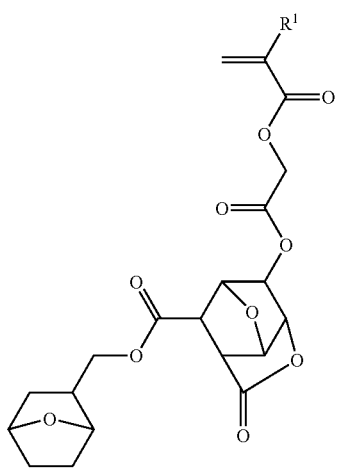
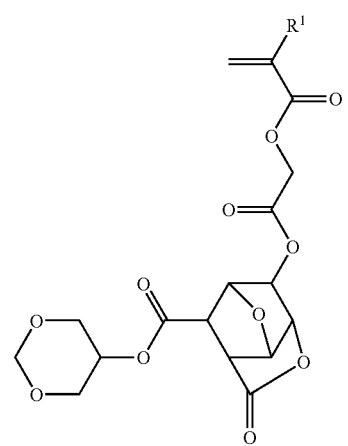
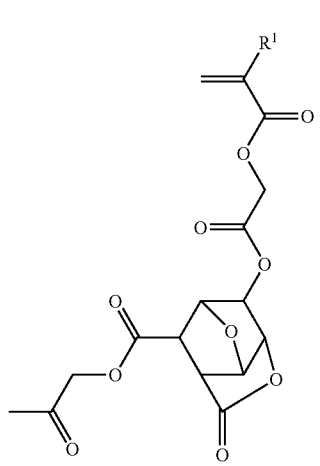
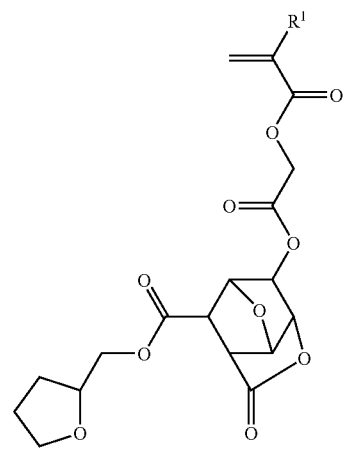
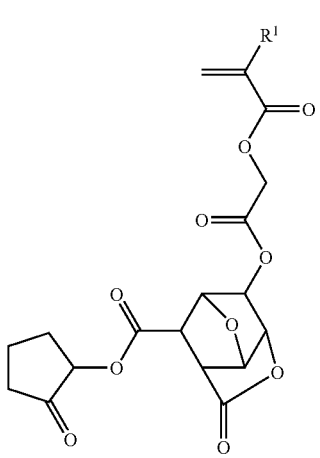

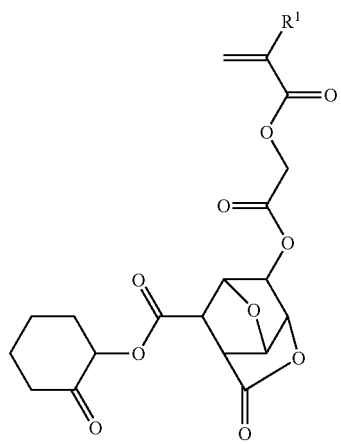

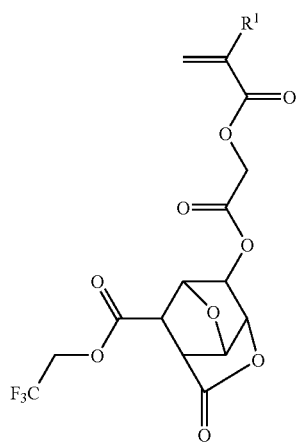

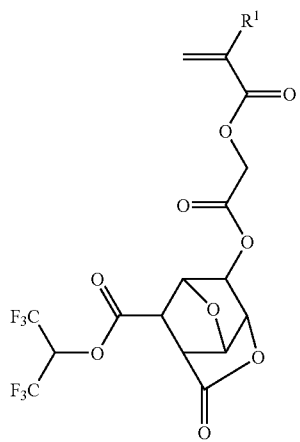

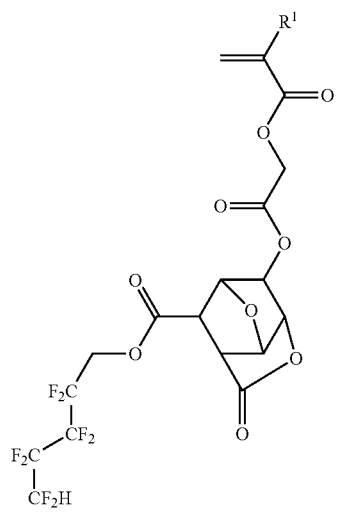

Herein $R^1$ is as defined above.

Of the monomers from which recurring units of formula (5L-1) are derived, those monomers wherein M'=1 are described in JP-A 2008-031298. Those monomers wherein M'=3 may be similarly synthesized aside from using chlorobutyric chloride instead of chloroacetyl chloride used as the reactant in the synthesis of the compounds wherein M'=1.

Illustrative examples of the recurring units of formula (5) are given below.

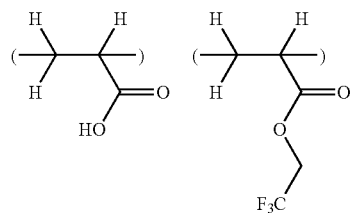

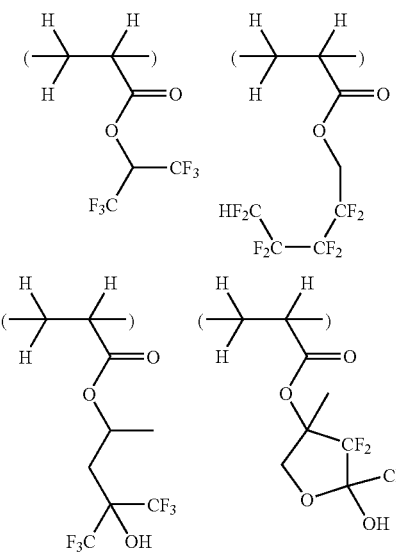

-continued
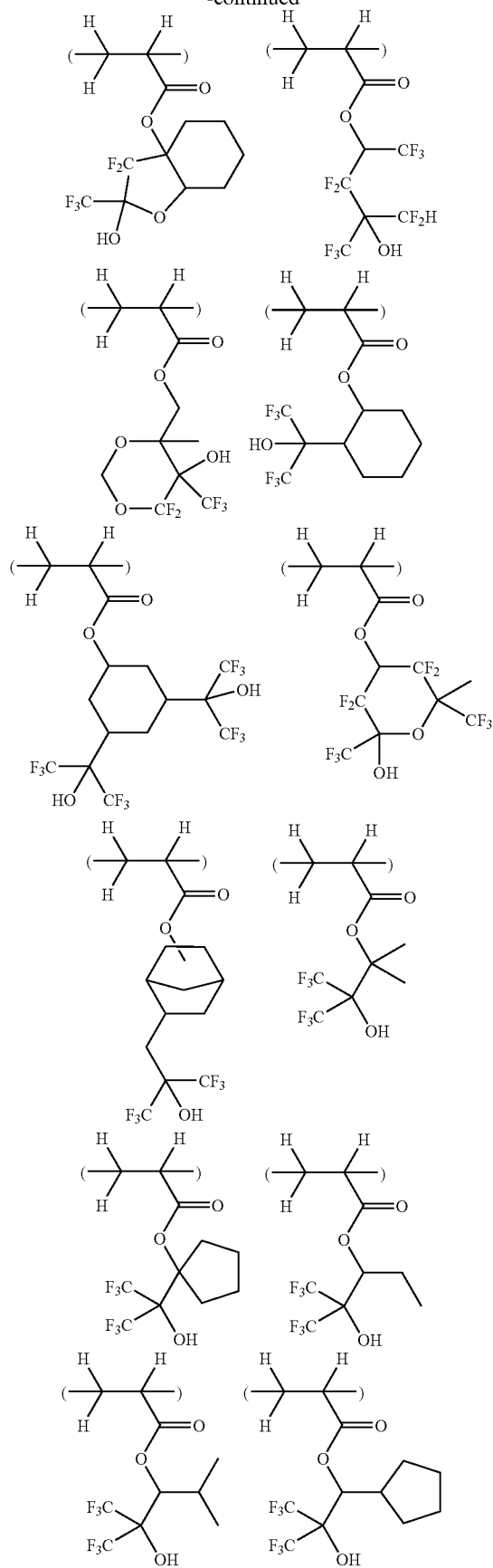
-continued
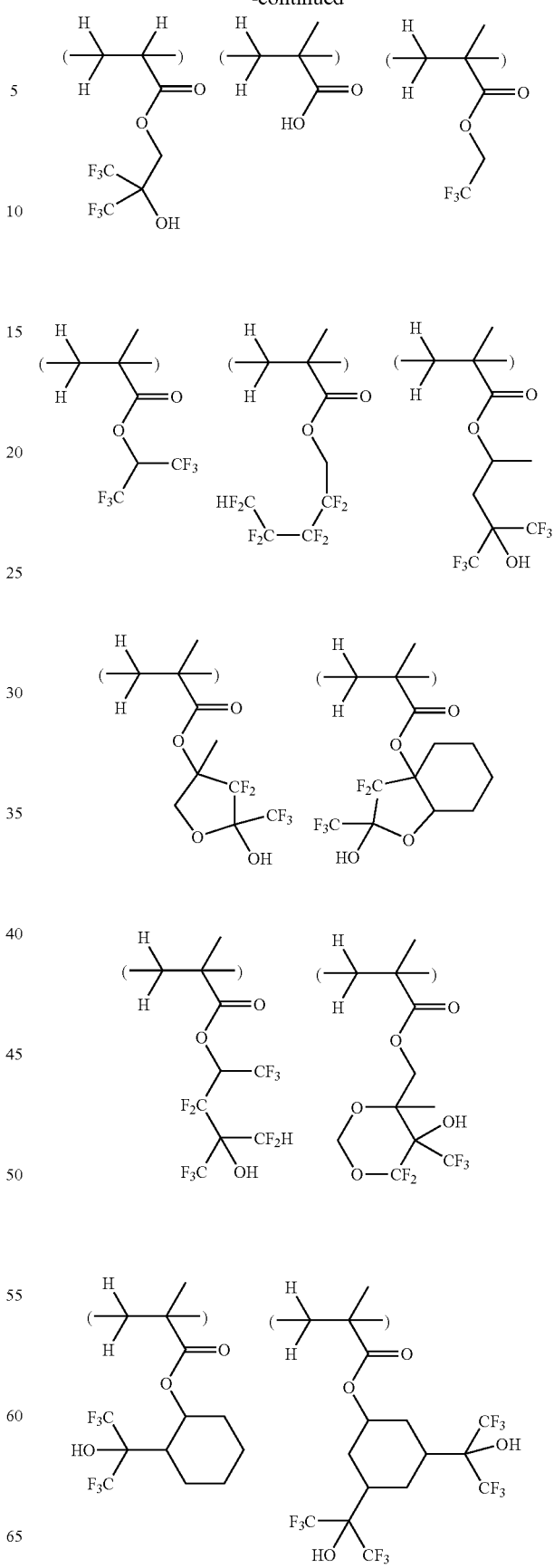

-continued
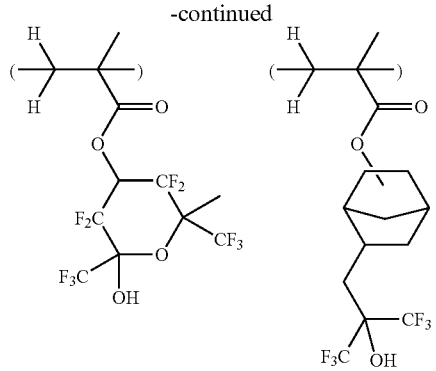
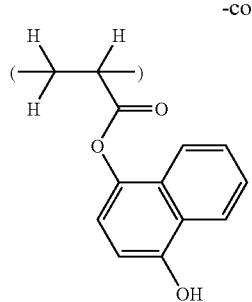
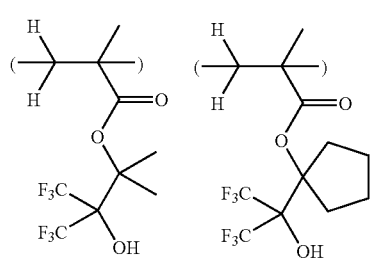
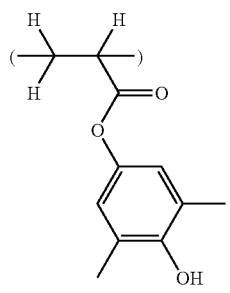
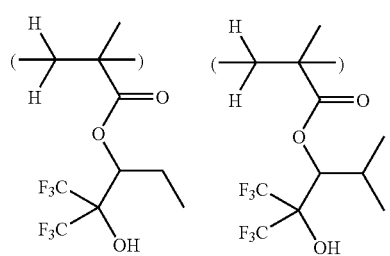
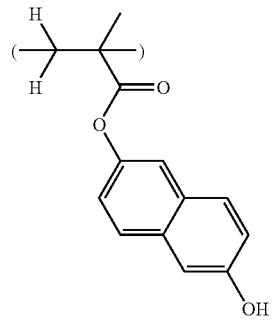
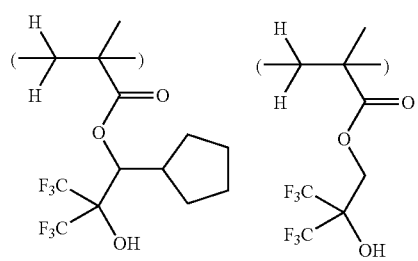
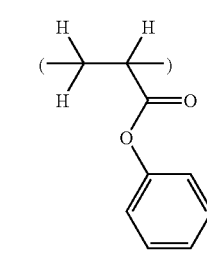
Illustrative examples of the recurring units of formula (6) are given below.
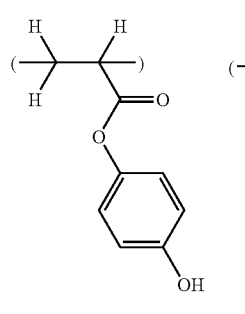
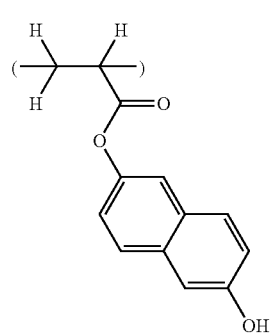
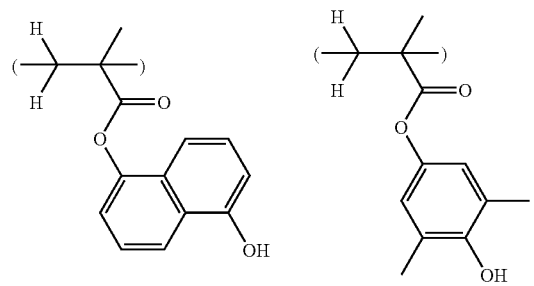
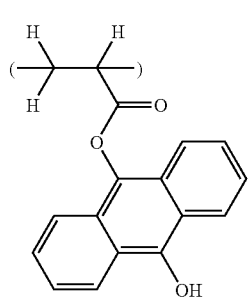
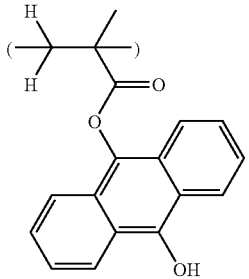

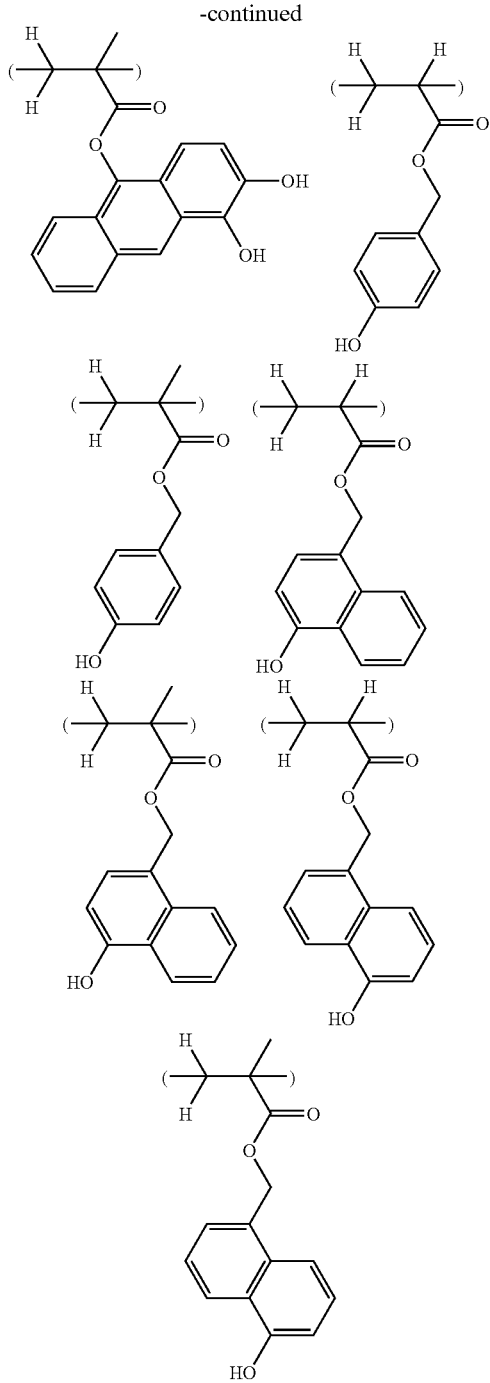

In a still further embodiment, the polymer comprising recurring units of formula (1b) may further comprise recurring units of at least one type selected from the general formulae (7) to (11) and optionally, recurring units of at least one type selected from the general formulae (2) to (6).

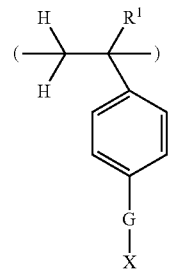

(7)

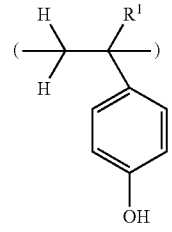

(8)

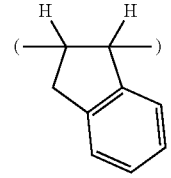

(9)

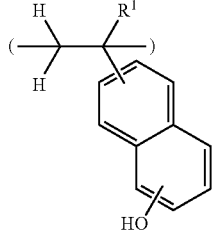

(10)

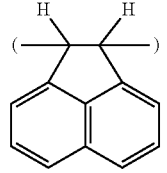

(11)

The polymer of the invention may further comprise recurring units derived from another monomer having a carbon-to-carbon double bond other than the foregoing. Examples of the additional monomer include substituted acrylates such as methyl methacrylate, methyl crotonate, dimethyl maleate, and dimethyl itaconate, unsaturated carboxylic acids such as maleic acid, fumaric acid and itaconic acid, cyclic olefins such as norbornene, norbornene derivatives, and tetracyclo[6.2.1.1$^{3,6}$.0$^{2,7}$]dodecene derivatives, unsaturated acid anhydrides such as itaconic anhydride, and other monomers.

The polymers of the invention are applicable not only to the ArF photolithography, but also to another lithography such as KrF, EB or EUV lithography.

Herein $R^1$ is as defined above, X is an acid labile group, and G is an oxygen atom or carbonyloxy group (—C(=O)O—).

Under the action of an acid, a polymer comprising recurring units of formula (7) is decomposed to generate a phenolic hydroxyl group and/or carboxylic acid whereby it becomes alkali soluble. The acid labile group X may be selected from a variety of such groups, for example, groups of formulae (L1) to (L4), tertiary alkyl groups of 4 to 20 carbon atoms, preferably 4 to 15 carbon atoms, trialkylsilyl groups in which each alkyl moiety has 1 to 6 carbon atoms, and oxoalkyl groups of 4 to 20 carbon atoms, as illustrated previously.

Illustrative non-limiting examples of the recurring units of formula (7) are given below.

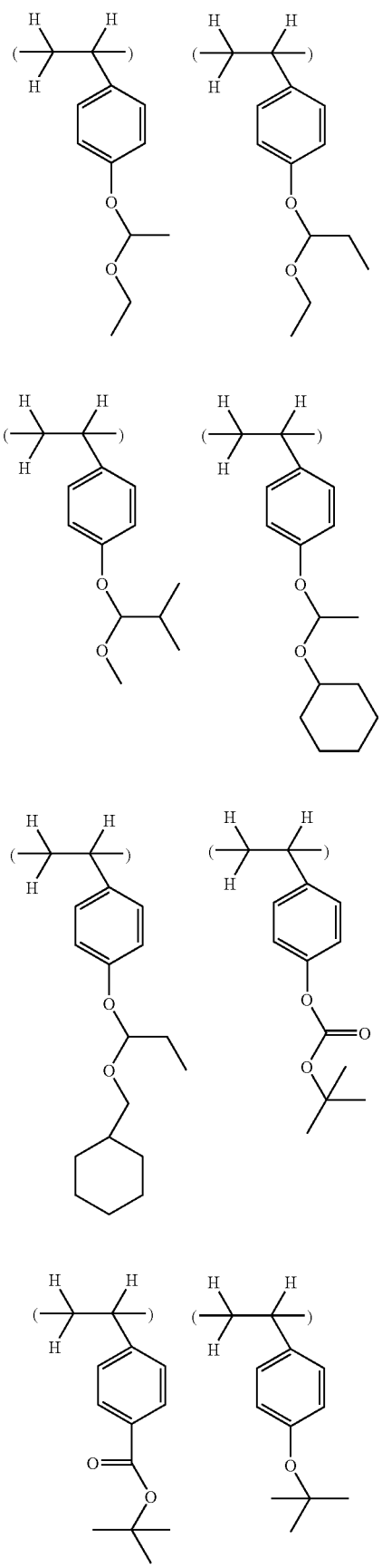
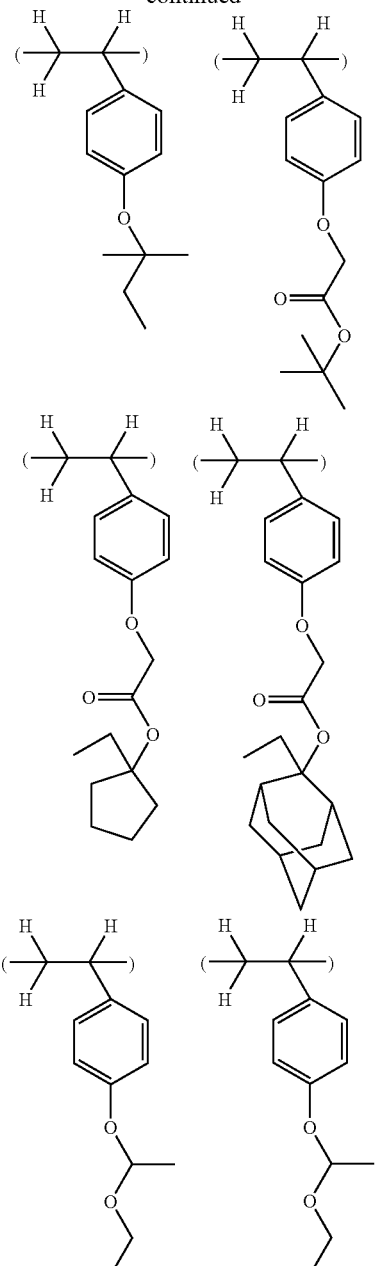

While hydroxyvinylnaphthalene of formula (10) may be substituted at arbitrary positions, typical substituted ones include 6-hydroxy-2-vinylnaphthalene and 4-hydroxy-1-vinylnaphthalene, with 6-hydroxy-2-vinylnaphthalene being preferred.

More preferred are those polymers comprising recurring units of any one type selected from formulae (7) to (11) and recurring units of formula (2) selected from among the recurring units of formulae (2) to (6).

The polymer of the invention comprising recurring units having a sulfonium salt with a polymerizable anion and recurring units of any one or more type selected from formulae (7) to (11) may further comprise recurring units derived from another monomer having a carbon-to-carbon double bond other than the foregoing. Examples of the additional monomer include substituted acrylates such as methyl methacrylate, methyl crotonate, dimethyl maleate, and dimethyl itaconate, unsaturated carboxylic acids such as maleic acid, fumaric acid and itaconic acid, cyclic olefins such as norbornene, norbornene derivatives, tetracyclo[6.2.1.1$^{3,6}$.0$^{2,7}$] dodecene derivatives, and norbornadiens, unsaturated acid anhydrides such as itaconic anhydride, styrene, acenaphthylene, vinylnaphthalene, and other monomers.

The polymers have a weight average molecular weight (Mw) of 1,000 to 500,000, and preferably 3,000 to 100,000. Outside the range, a polymer may suffer an extreme drop of etching resistance or a reduced resolution due to a failure to provide a difference in dissolution rate before and after exposure. The measurement of molecular weight may be performed by gel permeation chromatography (GPC) versus polystyrene standards.

In the inventive polymer, the preferred proportion of respective recurring units derived from discrete monomers may fall, for example, in the range (mol %) shown below, but is not limited thereto. The polymer may consist essentially of:

(I) from more than 0 mol % to 100 mol %, preferably 1 to 30 mol %, and more preferably 5 to 20 mol % of constituent units of one or more type having formula (1b) derived from monomer of formula (1);

(II) from 0 mol % to less than 100 mol %, preferably 70 to 99 mol %, and more preferably 80 to 95 mol % of constituent units of one or more type having formulae (2) to (6) and/or (7) to (11); and optionally (III) from 0 mol % to 80 mol %, preferably 0 to 70 mol %, and more preferably 0 to 50 mol % of constituent units of one or more type derived from the additional monomer(s).

The polymer may be prepared through copolymerization reaction using the compound of formula (1) as a first monomer and one or more compounds having a polymerizable double bond as second and subsequent monomers. Various modes of copolymerization reaction may be used for the preparation of the inventive polymer. The preferred modes are radical polymerization, anionic polymerization and coordination polymerization.

For radical polymerization, preferred reaction conditions include (a) a solvent selected from hydrocarbon solvents such as benzene, ether solvents such as tetrahydrofuran, alcohol solvents such as ethanol, and ketones such as methyl isobutyl ketone; (b) a polymerization initiator selected from azo compounds such as 2,2'-azobisisobutyronitrile and peroxides such as benzoyl peroxide and lauroyl peroxide; (c) a reaction temperature in the range of about 0° C. to about 100° C.; and (d) a reaction time in the range of about 0.5 to about 48 hours. Reaction parameters outside these ranges need not be excluded.

For anionic polymerization, preferred reaction conditions include (a) a solvent selected from among hydrocarbons such as benzene, ethers such as tetrahydrofuran, and liquid ammonia, (b) a polymerization initiator selected from metals such as sodium and potassium, alkyl metals such as n-butyllithium and sec-butyllithium, ketyl, and Grignard reagents, (c) a temperature of about −78° C. to about 0° C., (d) a time of about 0.5 to about 48 hours, and (e) a stopper selected from among proton-donative compounds such as methanol, halides such as methyl iodide, and electrophilic compounds. Reaction conditions outside the described range may be employed if desired.

For coordination polymerization, preferred reaction conditions include (a) a solvent selected from among hydrocarbons such as n-heptane and toluene, (b) a catalyst selected from Ziegler-Natta catalysts comprising a transition metal (e.g., titanium) and alkylaluminum, Phillips catalysts of metal oxides having chromium or nickel compounds carried thereon, and olefin-metathesis mixed catalysts as typified by tungsten and rhenium mixed catalysts, (c) a temperature of about 0° C. to about 100° C., and (d) a time of about 0.5 hour to about 48 hours. Reaction conditions outside the described range may be employed if desired.

Once a polymer is prepared by any of the above-described procedures, it may be modified by deprotecting some or all acid labile groups so that the polymer may be used in negative resist compositions as will be described later. Into the polymer in which acid labile groups have been deprotected, different acid labile groups may be introduced again. This indicates that acid labile groups different from the acid labile groups initially introduced during polymerization are introduced into the polymer.

For example, once a polymer is formed through radical polymerization of 4-ethoxyethoxystyrene with a polymerizable anion-containing sulfonium salt of formula (1), the polymer may be tailored into a copolymer with hydroxystyrene by eliminating ethoxyethoxy groups from the polymer using acetic acid, pyridinium tosylate or the like. The tailored copolymer may be used as a base resin in negative resist compositions. By further reacting hydroxystyrene units of the copolymer with di-tert-butyl dicarbonate, tert-butyl chloroacetate, vinyl ether or the like, acid labile groups different from the acid labile groups (ethoxyethoxy) initially introduced during polymerization may be introduced into the copolymer.

Resist Composition

The polymer of the invention is advantageously used as a base resin in a resist composition, and specifically a chemically amplified positive resist composition. Thus the invention provides a resist composition comprising the polymer, and especially a positive resist composition comprising the polymer. The positive resist composition preferably comprises:

(A) a base resin comprising the inventive polymer,
(B) an organic solvent, and optionally,
(C) an acid generator,
(D) a quencher, and
(E) a surfactant.

Also the polymer of the invention may be used as a base resin in a chemically amplified negative resist composition. The negative resist composition preferably comprises:

(A) a base resin comprising the inventive polymer,
(B) an organic solvent,
(F) a crosslinker for inducing crosslinkage under the action of an acid, and optionally,
(C) an acid generator,
(D) a quencher, and
(E) a surfactant.

For the positive resist composition, the base resin as component (A) may comprise another resin, specifically another polymer free of recurring units of formula (1b), having a dissolution rate in an alkaline developer that increases under the action of an acid, if desired, as well as the inventive polymer. Exemplary other resins include, but are not limited to, (i) poly(meth)acrylic acid derivatives, (ii) norbornene derivative/maleic anhydride copolymers, (iii) hydrogenated products of ring-opening metathesis polymerization (ROMP) polymers, (iv) vinyl ether/maleic anhydride/(meth)acrylic acid derivative copolymers, and (v) polyhydroxystyrene derivatives.

Of these, the poly(meth)acrylic acid derivatives (i) are polymers comprising units of formulae (2) to (6) and other units in combination. The polyhydroxystyrene derivatives (v) include polymers comprising units of formulae (7) to (11) in combination and polymers comprising units of formulae (2)

to (11) in combination. In these polymers, a proportion of those units having acid labile groups, for example, monomer units of one or more types selected from among formulae (2) and (7) and a combination thereof is from more than 0 mole % to 80 mole %, preferably 1 to 50 mole %, and more preferably 10 to 40 mole %.

The hydrogenated products of ROMP (iii) are synthesized by the method illustrated in Examples of JP-A 2003-66612. Illustrative examples of such hydrogenated polymers include those polymers having the recurring units shown below, but are not limited thereto.

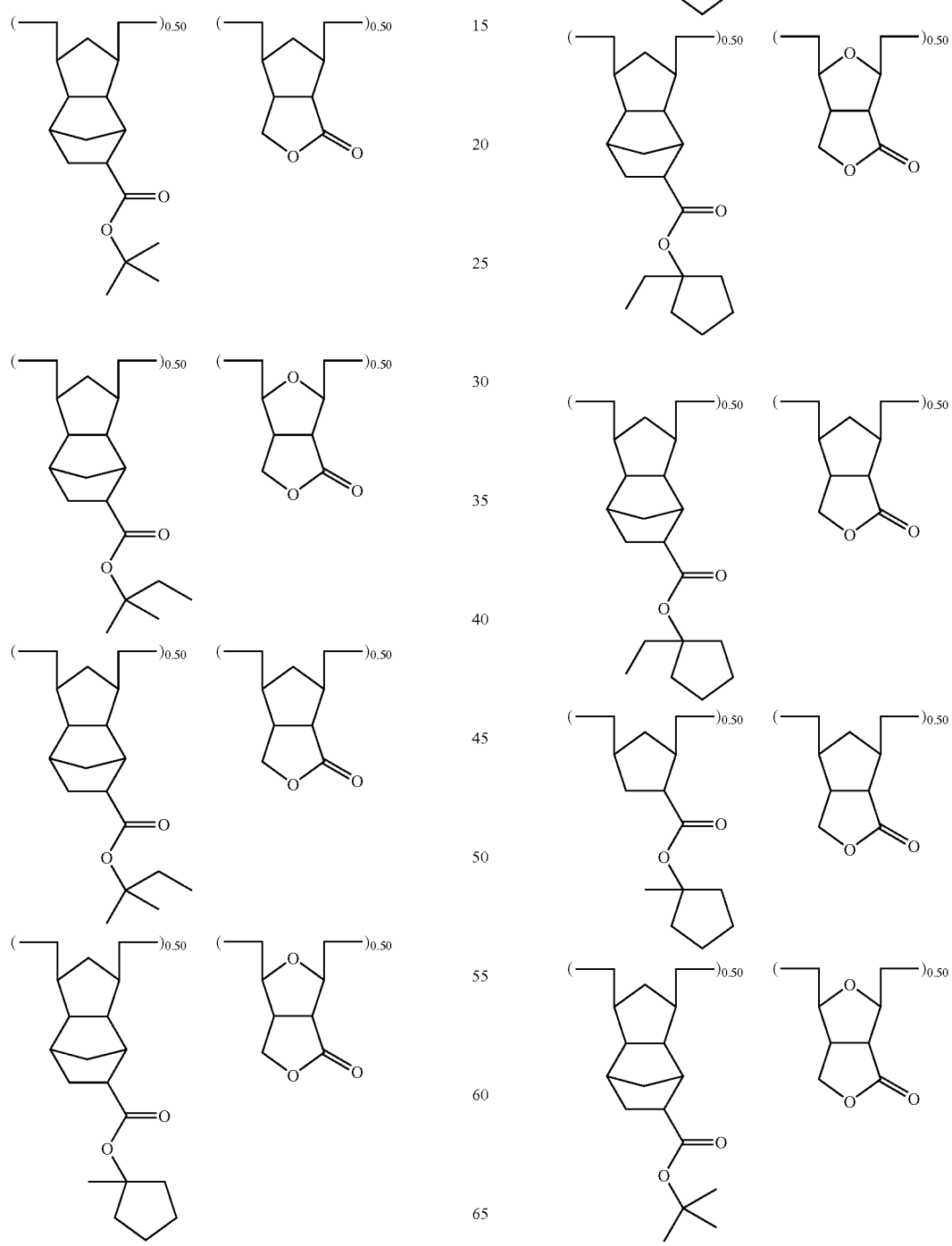

71
-continued
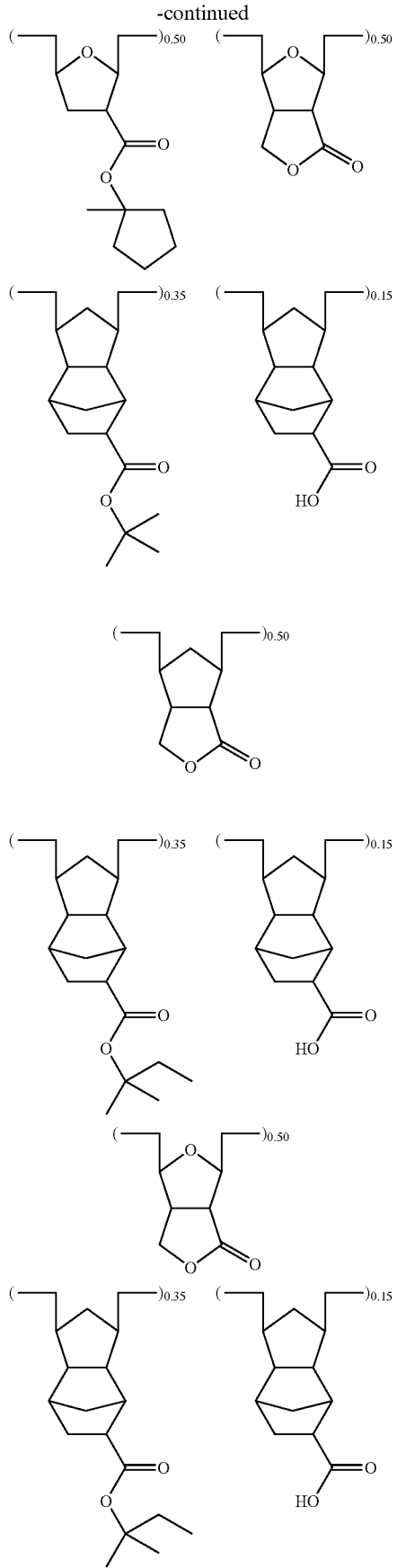
72
-continued
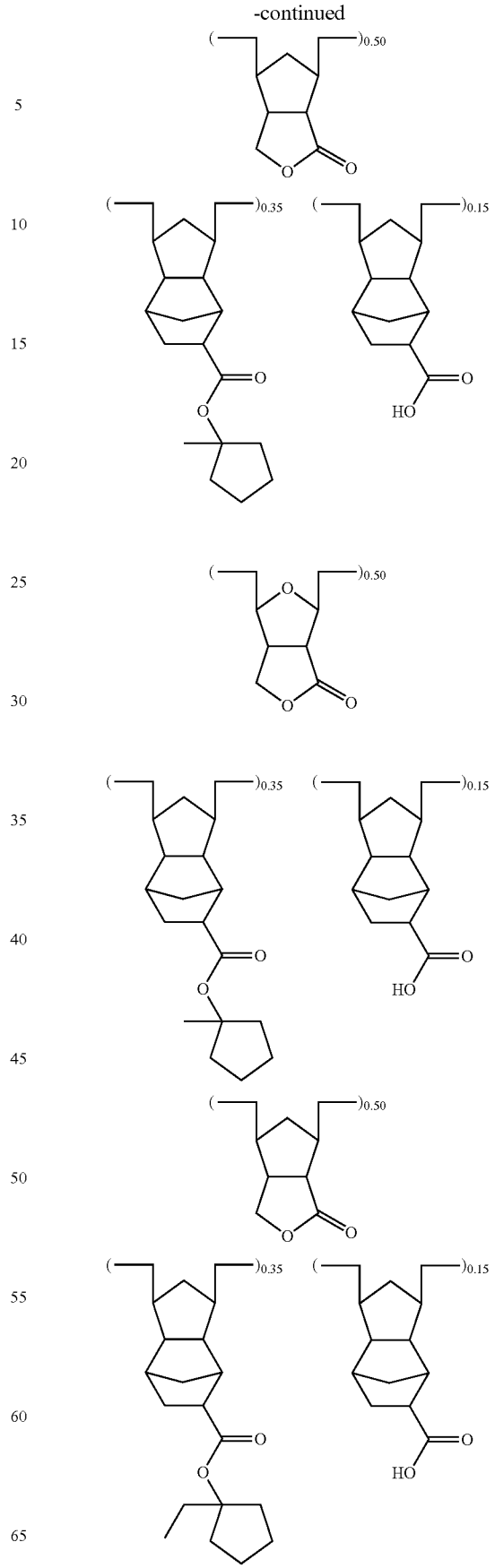

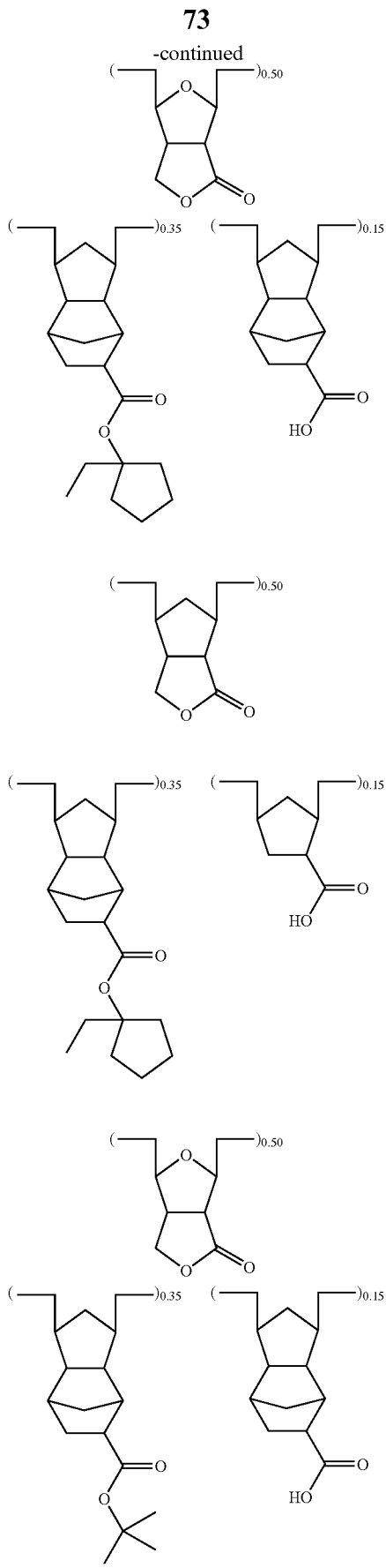

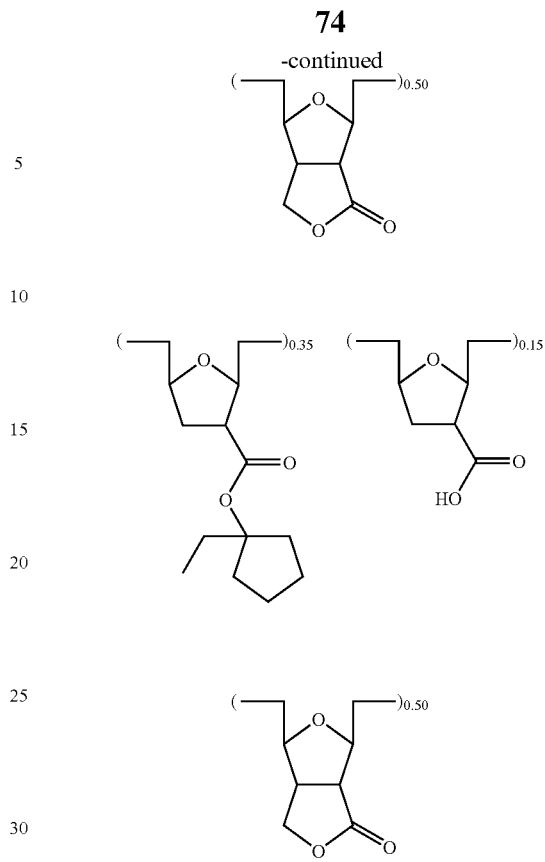

The inventive polymer and the other polymer are preferably blended in a weight ratio from 100:0 to 10:90, more preferably from 100:0 to 20:80. If the blend ratio of the inventive polymer is below this range, the resist composition would become poor in some of the desired properties. The properties of the resist composition can be adjusted by properly changing the blend ratio of the inventive polymer. The polymer is not limited to one type and a mixture of two or more polymers may be added. The use of plural polymers allows for easy adjustment of resist properties.

Organic Solvent

The organic Solvent (B) used herein may be any organic solvent in which the base resin, acid generator, and other components are soluble. Examples of the organic solvent are described in U.S. Pat. No. 7,537,880 or JP-A 2008-111103, paragraphs [0144] to [0145]. An appropriate amount of the organic solvent used is 200 to 15,000 parts, especially 400 to 8,000 parts by weight per 100 parts by weight of the base resin.

Photoacid Generator

In the practice of the invention, an acid generator is optionally used as component (C). Where a photoacid generator is added as the acid generator, it may be any compound capable of generating an acid upon exposure to high-energy radiation. Suitable photoacid generators include sulfonium salts, iodonium salts, sulfonyldiazomethane, N-sulfonyloxyimide, and oxime-O-sulfonate acid generators. The acid generators may be used alone or in admixture of two or more.

Examples of the acid generator are described in U.S. Pat. No. 7,537,880 or JP-A 2008-111103, paragraphs [0122] to [0138].

Among others, acid generators having the general formula (C)-1 are preferred.

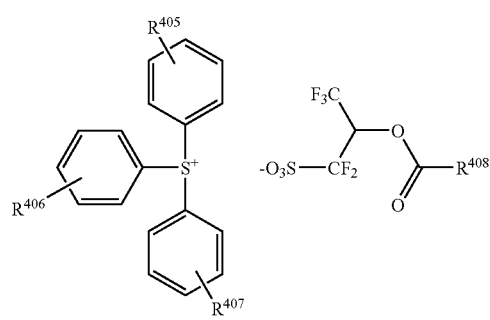

(C-1)

Herein $R^{405}$, $R^{406}$, and $R^{407}$ are each independently hydrogen or a straight, branched or cyclic, monovalent $C_1$-$C_{20}$ hydrocarbon group, typically an alkyl or alkoxy group, which may contain a heteroatom. Examples of hydrocarbon groups optionally containing a heteroatom include methyl, ethyl, propyl, isopropyl, n-butyl, sec-butyl, tert-butyl, tert-amyl, n-pentyl, n-hexyl, cyclopentyl, cyclohexyl, ethylcyclopentyl, butylcyclopentyl, ethylcyclohexyl, butylcyclohexyl, adamantyl, ethyladamantyl, butyladamantyl, and modified forms of the foregoing in which any carbon-to-carbon bond is separated by a hetero-atomic grouping such as —O—, —S—, —SO—, —SO$_2$—, —NH—, —C(=O)—, —C(=O)O—, or —C(=O)NH—, or any hydrogen atom is replaced by a functional group such as —OH, —NH$_2$, —CHO, or —CO$_2$H. $R^{408}$ is a straight, branched or cyclic, monovalent $C_7$-$C_{30}$ hydrocarbon group which may contain a heteroatom, examples of which are exemplified below, but are not limited thereto.

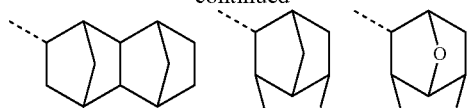

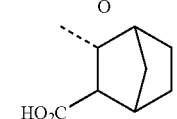

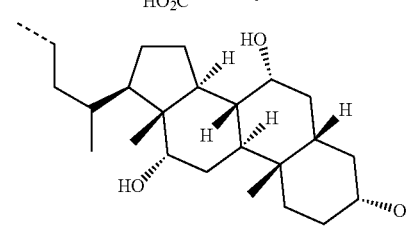

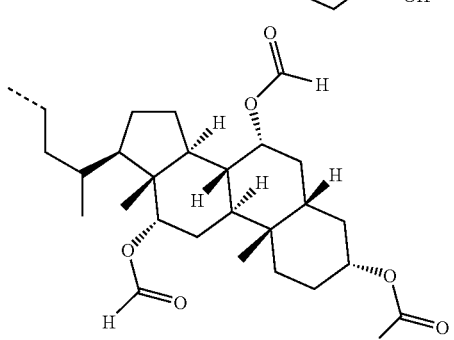

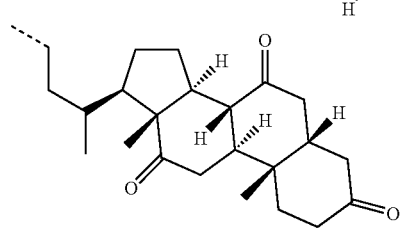

Illustrative examples of acid generators (C)-1 are shown below.

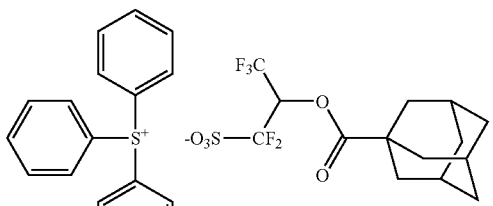

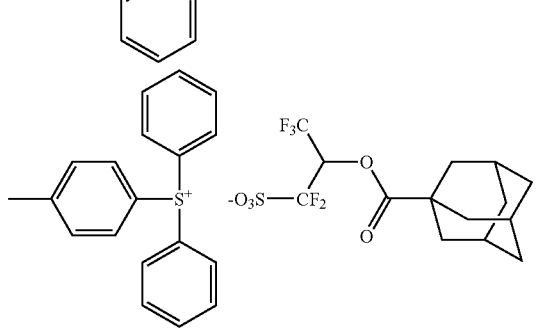

77
-continued
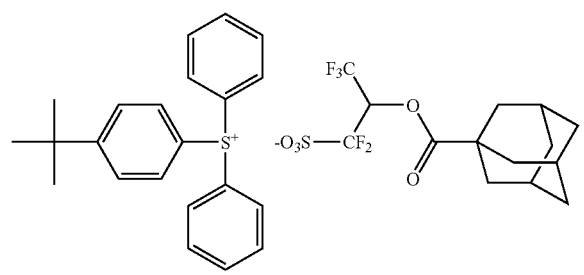
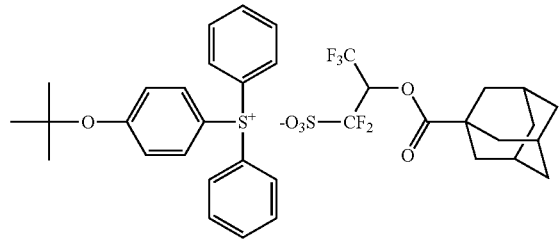
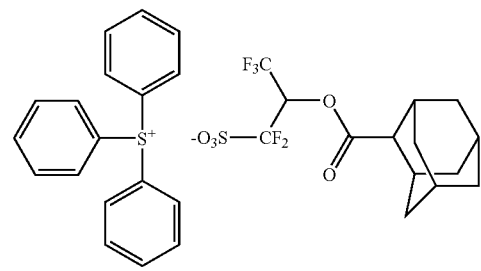
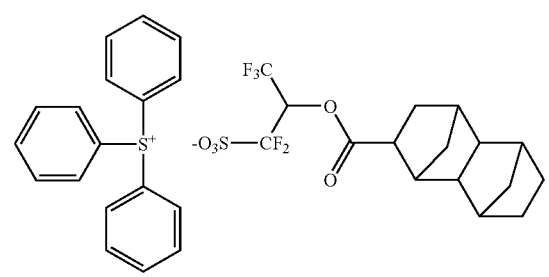
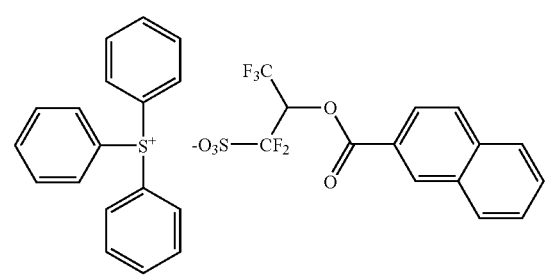
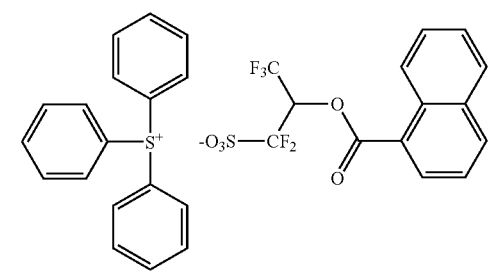
78
-continued
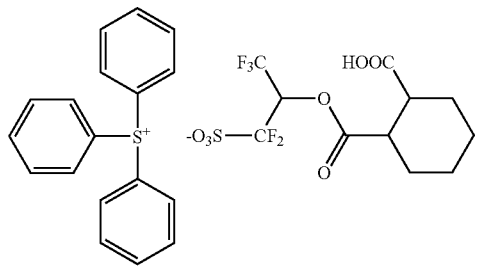
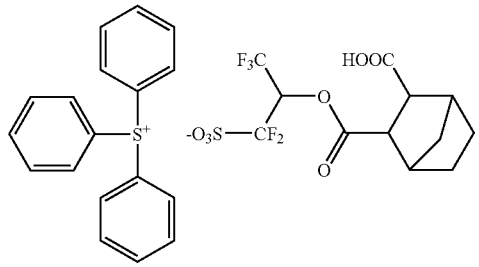
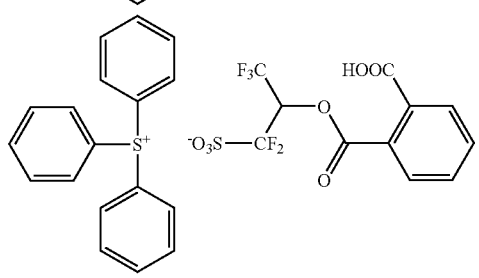
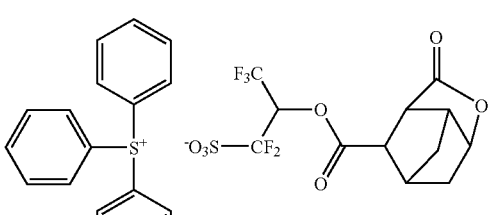
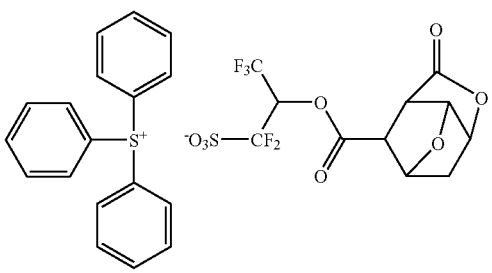

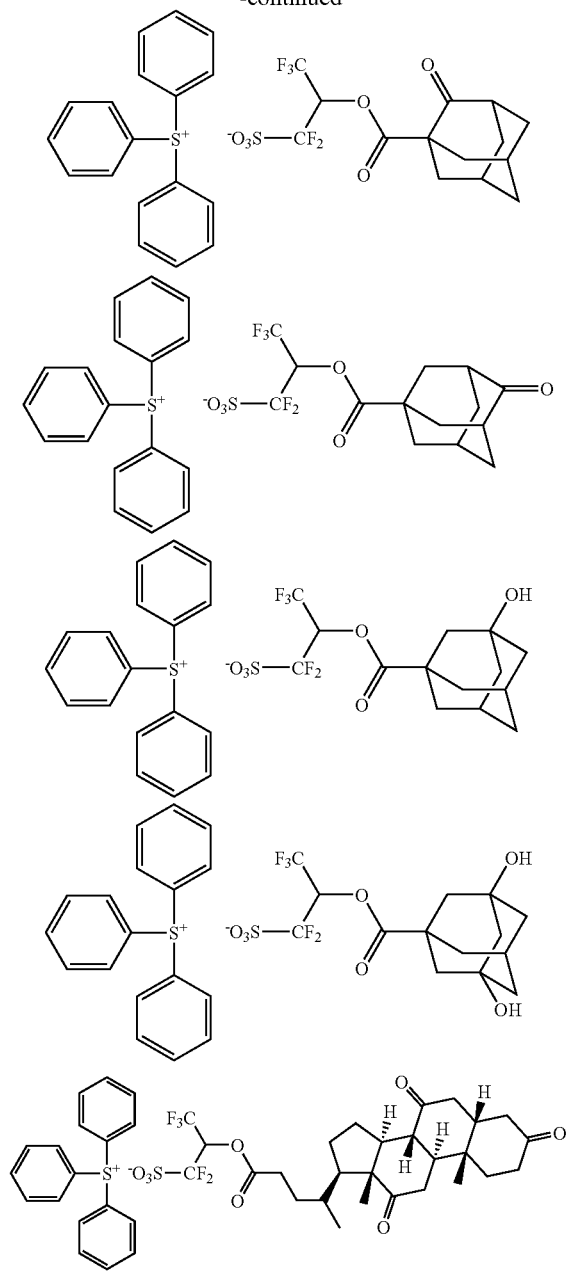

In the chemically amplified resist composition, the photoacid generator (C) may be added in any desired amount as long as the objects of the invention are not compromised. An appropriate amount of the photoacid generator (C), when added, is 0.1 to 10 parts, and more preferably 0.1 to 5 parts by weight per 100 parts by weight of the base resin in the composition. Too high a proportion of the photoacid generator (C) may give rise to problems of degraded resolution and foreign matter upon development and resist film peeling. The photoacid generators (C) may be used alone or in admixture of two or more. The transmittance of the resist film can be controlled by using a photoacid generator having a low transmittance at the exposure wavelength and adjusting the amount of the photoacid generator added.

It is noted that an acid diffusion controlling function may be provided when two or more photoacid generators are used in admixture provided that one photoacid generator is an onium salt capable of generating a weak acid. Specifically, in a system using a mixture of a photoacid generator capable of generating a strong acid (e.g., fluorinated sulfonic acid) and an onium salt capable of generating a weak acid (e.g., non-fluorinated sulfonic acid or carboxylic acid), if the strong acid generated from the photoacid generator upon exposure to high-energy radiation collides with the unreacted onium salt having a weak acid anion, then a salt exchange occurs whereby the weak acid is released and an onium salt having a strong acid anion is formed. In this course, the strong acid is exchanged into the weak acid having a low catalysis, incurring apparent deactivation of the acid for enabling to control acid diffusion.

If the photoacid generator capable of generating a strong acid is also an onium salt, an exchange from the strong acid (generated upon exposure to high-energy radiation) to a weak acid as above can take place, but it never happens that the weak acid (generated upon exposure to high-energy radiation) collides with the unreacted onium salt capable of generating a strong acid to induce a salt exchange. This is because of a likelihood of an onium cation forming an ion pair with a stronger acid anion.

In the resist composition of the invention, there may be added a compound which is decomposed with an acid to generate another acid, that is, acid amplifier compound. For these compounds, reference should be made to J. Photopolym. Sci. and Tech., 8, 43-44, 45-46 (1995), and ibid., 9, 29-30 (1996).

Examples of the acid amplifier compound include tert-butyl-2-methyl-2-tosyloxymethyl acetoacetate and 2-phenyl-2-(2-tosyloxyethyl)-1,3-dioxolane, but are not limited thereto. Of well-known photoacid generators, many of those compounds having poor stability, especially poor thermal stability exhibit an acid amplifier-like behavior.

In the resist composition of the invention, an appropriate amount of the acid amplifier compound is up to 2 parts, and especially up to 1 part by weight per 100 parts by weight of the base resin. Excessive amounts of the acid amplifier compound make diffusion control difficult, leading to degradation of resolution and pattern profile.

Quencher

A quencher (D) may be optionally used in the resist composition of the invention. The term "quencher" as used herein has a meaning generally known in the art and refers to a compound capable of suppressing the rate of diffusion when the acid generated by the acid generator diffuses within the resist film. The inclusion of quencher facilitates adjustment of resist sensitivity and holds down the rate of acid diffusion within the resist film, resulting in better resolution. In addition, it suppresses changes in sensitivity following exposure and reduces substrate and environment dependence, as well as improving the exposure latitude and the pattern profile.

Examples of suitable quenchers include primary, secondary, and tertiary aliphatic amines, mixed amines, aromatic amines, heterocyclic amines, nitrogen-containing compounds with carboxyl group, nitrogen-containing compounds with sulfonyl group, nitrogen-containing compounds with hydroxyl group, nitrogen-containing compounds with hydroxyphenyl group, alcoholic nitrogen-containing compounds, amide derivatives, imide derivatives, carbamate derivatives, and ammonium salts.

Examples of the quencher are described in U.S. Pat. No. 7,537,880 or JP-A 2008-111103, paragraphs [0146] to [0163].

Tertiary amines are especially preferred as the quencher. Examples include tri-n-butylamine, tri-n-pentylamine, tri-n-hexylamine, tri-n-octylamine, N,N-dimethylaniline, triethanolamine, triisopropanolamine, tris(2-methoxymethoxyethyl)amine, tris(2-methoxyethoxyethyl)amine, tris{2-(2-methoxyethoxy)ethyl}amine, tris{2-(2-methoxyethoxymethoxy)ethyl}amine, tris{2-(1-methoxyethoxy)ethyl}amine, tris{2-(1-ethoxyethoxy)ethyl}amine, tris{2-(1-ethoxypropoxy)ethyl}amine, tris[2-{2-(2-hydroxyethoxy)ethoxy}ethyl]amine, 4,7,13,16,21,24-hexaoxa-1,10-diazabicyclo[8.8.8]hexacosane, 4,7,13,18-tetraoxa-1,10-diazabicyclo[8.5.5]eicosane, 1,4,10,13-tetraoxa-7,16-diazabicyclooctadecane, 1-aza-12-crown-4, 1-aza-15-crown-5, 1-aza-18-crown-6, tris(2-formyloxyethyl)amine, tris(2-acetoxyethyl)amine, tris(2-propionyloxyethyl)amine, tris(2-butyryloxyethyl)amine, tris(2-isobutyryloxyethyl)amine, tris(2-valeryloxyethyl)amine, tris(2-pivaloyloxyethyl)amine, N,N-bis(2-acetoxyethyl)-2-(acetoxyacetoxy)ethylamine, tris(2-methoxycarbonyloxyethyl)amine, tris(2-tert-butoxycarbonyloxyethyl)amine, tris[2-(2-oxopropoxy)ethyl]amine, tris[2-(methoxycarbonylmethyl)oxyethyl]amine, tris[2-(tert-butoxycarbonylmethyloxy)ethyl]amine, tris[2-(cyclohexyloxycarbonylmethyloxy)ethyl]amine, tris (2-methoxycarbonylethyl)amine, tris(2-ethoxycarbonylethyl)amine, tris(2-benzoyloxyethyl)amine, tris[2-(4-methoxybenzoyloxy)ethyl]amine, N,N-bis(2-hydroxyethyl)-2-(methoxycarbonyl)ethylamine, N,N-bis(2-acetoxyethyl)-2-(methoxycarbonyl)ethylamine, N,N-bis(2-hydroxyethyl)-2-(ethoxycarbonyl)ethylamine, N,N-bis(2-acetoxyethyl)-2-(ethoxycarbonyl)ethylamine, N,N-bis(2-acetoxyethyl)-2-(2-methoxyethoxycarbonyl)ethylamine, N,N-bis(2-acetoxyethyl)-2-(2-methoxyethoxycarbonyl)ethylamine, N,N-bis(2-hydroxyethyl)-2-(2-hydroxyethoxycarbonyl)ethylamine, N,N-bis(2-acetoxyethyl)-2-(2-acetoxyethoxycarbonyl)ethylamine, N,N-bis(2-hydroxyethyl)-2-[(methoxycarbonyl)methoxycarbonyl]-ethylamine, N,N-bis(2-acetoxyethyl)-2-[(methoxycarbonyl)methoxycarbonyl]-ethylamine, N,N-bis(2-hydroxyethyl)-2-(2-oxopropoxycarbonyl)ethylamine, N,N-bis(2-acetoxyethyl)-2-(2-oxopropoxycarbonyl)ethylamine, N,N-bis(2-hydroxyethyl)-2-(tetrahydrofurfuryloxycarbonyl)-ethylamine, N,N-bis(2-acetoxyethyl)-2-(tetrahydrofurfuryloxycarbonyl)-ethylamine, N,N-bis(2-hydroxyethyl)-2-[(2-oxotetrahydrofuran-3-yl)oxy-carbonyl]ethylamine, N,N-bis(2-acetoxyethyl)-2-[(2-oxotetrahydrofuran-3-yl)oxy-carbonyl]ethylamine, N,N-bis (2-hydroxyethyl)-2-(4-hydroxybutoxycarbonyl)ethylamine, N,N-bis(2-formyloxyethyl)-2-(4-formyloxybutoxycarbonyl)-ethylamine, N,N-bis(2-formyloxyethyl)-2-(2-formyloxyethoxycarbonyl)-ethylamine, N,N-bis(2-methoxyethyl)-2-(methoxycarbonyl)ethylamine, N-(2-hydroxyethyl)-bis[2-(methoxycarbonyl)ethyl]amine, N-(2-acetoxyethyl)-bis[2-(methoxycarbonyl)ethyl]amine, N-(2-hydroxyethyl)-bis[2-(ethoxycarbonyl)ethyl]amine, N-(2-acetoxyethyl)-bis[2-(ethoxycarbonyl)ethyl]amine, N-(3-hydroxy-1-propyl)-bis[2-(methoxycarbonyl)ethyl]amine, N-(3-acetoxy-1-propyl)-bis[2-(methoxycarbonyl)ethyl]amine, N-(2-methoxyethyl)-bis[2-(methoxycarbonyl)ethyl]amine, N-butyl-bis[2-(methoxycarbonyl)ethyl]amine, N-butyl-bis[2-(2-methoxyethoxycarbonyl)ethyl]amine, N-methyl-bis(2-acetoxyethyl)amine, N-ethyl-bis(2-acetoxyethyl)amine, N-methyl-bis(2-pivaloyloxyethyl)amine, N-ethyl-bis[2-(methoxycarbonyloxy)ethyl]amine, N-ethyl-bis[2-(tert-butoxycarbonyloxy)ethyl]amine, tris(methoxycarbonylmethyl)amine, tris(ethoxycarbonylmethyl)amine, N-butyl-bis(methoxycarbonylmethyl)amine, N-hexyl-bis(methoxycarbonylmethyl)amine, and β-(diethylamino)-δ-valerolactone.

Further examples of the quencher include 1-[2-(methoxymethoxy)ethyl]pyrrolidine, 1-[2-(methoxymethoxy)ethyl]piperidine, 4-[2-(methoxymethoxy)ethyl]morpholine, 1-[2-(methoxymethoxy)ethyl]imidazole, 1-[2-(methoxymethoxy)ethyl]benzimidazole, 1-[2-(methoxymethoxy)ethyl]-2-phenylbenzimidazole, 1-[2-[(2-methoxyethoxy)methoxy]ethyl]pyrrolidine, 1-[2-[(2-methoxyethoxy)methoxy]ethyl]piperidine, 4-[2-[(2-methoxyethoxy)methoxy]ethyl]morpholine, 1-[2-[(2-methoxyethoxy)methoxy]ethyl]imidazole, 1-[2-[(2-methoxyethoxy)methoxy]ethyl]benzimidazole, 1-[2-[(2-methoxyethoxy)methoxy]ethyl]-2-phenylbenzimidazole, 1-[2-[2-(2-methoxyethoxy)ethoxy]ethyl]pyrrolidine, 1-[2-[2-(2-methoxyethoxy)ethoxy]ethyl]piperidine, 4-[2-[2-(2-methoxyethoxy)ethoxy]ethyl]morpholine, 1-[2-[2-(2-methoxyethoxy)ethoxy]ethyl]imidazole, 1-[2-[2-(2-methoxyethoxy)ethoxy]ethyl]benzimidazole, 1-[2-[2-(2-methoxyethoxy)ethoxy]ethyl]-2-phenylbenzimidazole, 1-[2-[2-(2-butoxyethoxy)ethoxy]ethyl]pyrrolidine, 1-[2-[(2-(2-butoxyethoxy)ethoxy]ethyl]piperidine, 4-[2-[2-(2-butoxyethoxy)ethoxy]ethyl]morpholine, 1-[2-[2-(2-butoxyethoxy)ethoxy]ethyl]imidazole, 1-[2-[2-(2-butoxyethoxy)ethoxy]ethyl]benzimidazole, 1-[2-[2-(2-butoxyethoxy)ethoxy]ethyl]-2-phenylbenzimidazole, 1-[2-[2-[2-(2-methoxyethoxy)ethoxy]ethoxy]ethyl]pyrrolidine, 1-[2-[2-[2-(2-methoxyethoxy)ethoxy]ethoxy]ethyl]piperidine, 4-[2-[2-[2-(2-methoxyethoxy)ethoxy]ethoxy]ethyl]morpholine, 1-[2-[2-[2-(2-methoxyethoxy)ethoxy]ethoxy]ethyl]imidazole, 1-[2-[2-[2-(2-methoxyethoxy)ethoxy]ethoxy]ethyl]benzimidazole, 1-[2-[2-[2-(2-methoxyethoxy)ethoxy]ethoxy]ethyl]-2-phenyl-benzimidazole, 4-[2-{2-[2-(2-butoxyethoxy)ethoxy]ethoxy}ethyl]morpholine, 2-(1-pyrrolidinyl)ethyl acetate, 2-piperidinoethyl acetate, 2-morpholinoethyl acetate, 2-(1-imidazolyl)ethyl acetate, 2-(1-benzimidazolyl)ethyl acetate, 2-(2-phenyl-1-benzimidazolyl)ethyl acetate, 2-methoxyethyl morpholinoacetate, 2-(1-pyrrolidinyl)ethyl 2-methoxyacetate, 2-piperidinoethyl 2-methoxyacetate, 2-morpholinoethyl 2-methoxyacetate, 2-(1-imidazolyl)ethyl 2-methoxyacetate, 2-(1-benzimidazolyl)ethyl 2-methoxyacetate, 2-(2-phenyl-1-benzimidazolyl)ethyl 2-methoxyacetate, 2-(1-pyrrolidinyl)ethyl 2-(2-methoxyethoxy)acetate, 2-piperidinoethyl 2-(2-methoxyethoxy)acetate, 2-morpholinoethyl 2-(2-methoxyethoxy)acetate, 2-(1-imidazolyl)ethyl 2-(2-methoxyethoxy)acetate, 2-(1-benzimidazolyl)ethyl 2-(2-methoxyethoxy)acetate, 2-(2-phenyl-1-benzimidazolyl)ethyl 2-(2-methoxyethoxy)acetate, 2-(1-pyrrolidinyl)ethyl 2-[2-(2-methoxyethoxy)ethoxy]acetate, 2-piperidinoethyl 2-[2-(2-methoxyethoxy)ethoxy]acetate, 2-morpholinoethyl 2-[2-(2-methoxyethoxy)ethoxy]acetate, 2-(1-imidazolyl)ethyl 2-[2-(2-methoxyethoxy)ethoxy]acetate, 2-(1-benzimidazolyl)ethyl 2-[2-(2-methoxyethoxy)ethoxy]acetate, 2-(2-phenyl-1-benzimidazolyl)ethyl 2-[2-(2-methoxyethoxy)-ethoxy]acetate, 2-morpholinoethyl butyrate, 2-morpholinoethyl hexanoate, 2-morpholinoethyl octanoate, 2-morpholinoethyl decanoate, 2-morpholinoethyl laurate, 2-morpholinoethyl myristate, 2-morpholinoethyl palmitate, 2-morpholinoethyl stearate, 2-morpholinoethyl behenate, 2-morpholinoethyl cholate, 2-morpholinoethyl tris(O-acetyl)cholate, 2-morpholinoethyl tris(O-formyl)cholate, 2-morpholinoethyl dehydrocholate, 2-morpholinoethyl cyclopentanecarboxylate, 2-morpholinoethyl cyclohexanecarboxylate, 2-(1-pyrrolidinyl)ethyl 7-oxanorbornane-2-carboxylate, 2-piperidinoethyl 7-oxanorbornane-2-carboxylate, 2-morpholinoethyl 7-oxanorbornane-2-carboxylate, 2-(1-imidazolyl)ethyl 7-oxanorbornane-2-carboxylate, 2-(1-benzimidazolyl)ethyl 7-oxanorbornane-2- carboxylate, 2-(2-phenyl-1-benzimidazolyl)ethyl 7-oxanorbornane-2-carboxylate, 2-morpholinoethyl adamantanecarboxylate, 2-(1-pyrrolidinyl)ethyl formate, 2-piperidinoethyl propionate, 2-morpholinoethyl acetoxyacetate, 2-(1-pyrrolidinyl)ethyl methoxyacetate, 2-(1-pyrrolidinyl) ethyl benzoate, 2-piperidinoethyl benzoate, 2-morpholinoethyl benzoate, 2-(1-imidazolyl)ethyl benzoate, 2-(1-benzimidazolyl)ethyl benzoate, 2-(2-phenyl-1-benzimidazolyl)ethyl benzoate, 2-(1-pyrrolidinyl)ethyl 4-methoxybenzoate, 2-piperidinoethyl 4-methoxybenzoate, 2-morpholinoethyl 4-methoxybenzoate, 2-(1-imidazolyl)ethyl 4-methoxybenzoate, 2-(1-benzimidazolyl)ethyl 4-methoxybenzoate, 2-(2-phenyl-1-benzimidazolyl)ethyl 4-methoxybenzoate, 2-(1-pyrrolidinyl)ethyl 4-phenylbenzoate, 2-piperidinoethyl 4-phenylbenzoate, 2-morpholinoethyl 4-phenylbenzoate, 2-(1-imidazolyl)ethyl 4-phenylbenzoate, 2-(1-benzimidazolyl)ethyl 4-phenylbenzoate, 2-(2-phenyl-1-benzimidazolyl)ethyl 4-phenylbenzoate, 2-(1-pyrrolidinyl)ethyl 1-naphthalenecarboxylate, 2-piperidinoethyl 1-naphthalenecarboxylate, 2-morpholinoethyl 1-naphthalenecarboxylate, 2-(1-imidazolyl)ethyl 1-naphthalenecarboxylate, 2-(1-benzimidazolyl)ethyl 1-naphthalenecarboxylate, 2-(2-phenyl-1-benzimidazolyl)ethyl 1-naphthalenecarboxylate, 2-(1-pyrrolidinyl)ethyl 2-naphthalenecarboxylate, 2-piperidinoethyl 2-naphthalenecarboxylate, 2-morpholinoethyl 2-naphthalenecarboxylate, 2-(1-imidazolyl)ethyl 2-naphthalenecarboxylate, 2-(1-benzimidazolyl)ethyl 2-naphthalenecarboxylate, 2-(2-phenyl-1-benzimidazolyl)ethyl 2-naphthalenecarboxylate, 4-[2-(methoxycarbonyloxy)ethyl]morpholine, 1-[2-(t-butoxycarbonyloxy)ethyl]piperidine, 4-[2-(2-methoxyethoxycarbonyloxy)ethyl]morpholine, methyl 3-(1-pyrrolidinyl)propionate, methyl 3-piperidinopropionate, methyl 3-morpholinopropionate, methyl 3-(thiomorpholino) propionate, methyl 2-methyl-3-(1-pyrrolidinyl)propionate, ethyl 3-morpholinopropionate, methoxycarbonylmethyl 3-piperidinopropionate, 2-hydroxyethyl 3-(1-pyrrolidinyl) propionate, 2-acetoxyethyl 3-morpholinopropionate, 2-oxotetrahydrofuran-3-yl 3-(1-pyrrolidinyl)propionate, tetrahydrofurfuryl 3-morpholinopropionate, glycidyl 3-piperidinopropionate, 2-methoxyethyl 3-morpholinopropionate, 2-(2-methoxyethoxy)ethyl 3-(1-pyrrolidinyl)propionate, butyl 3-morpholinopropionate, cyclohexyl 3-piperidinopropionate, α-(1-pyrrolidinyl)methyl-γ-butyrolactone, β-piperidino-γ-butyrolactone, β-morpholino-δ-valerolactone, methyl 1-pyrrolidinylacetate, methyl piperidinoacetate, methyl morpholinoacetate, methyl thiomorpholinoacetate, ethyl 1-pyrrolidinylacetate, etc.

The quenchers may be used alone or in admixture of two or more. The quencher is preferably formulated in an amount of 0.001 to 5 parts, and especially 0.01 to 3 parts by weight, per 100 parts by weight of the total base resin. Less than 0.001 phr of the quencher may achieve no addition effect whereas more than 5 phr may lead to too low a sensitivity.

Surfactant

Optionally, the resist composition of the invention may further comprise (E) a surfactant which is commonly used for facilitating the coating operation. The surfactant may be added in conventional amounts so long as this does not compromise the objects of the invention.

Examples of the surfactant are described in U.S. Pat. No. 7,537,880 or JP-A 2008-111103, paragraphs [0165] to [0166].

Additional useful surfactants include partially fluorinated oxetane ring-opened polymers having the structural formula (surf-1).

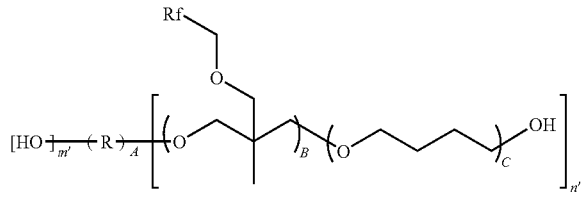

(surf-1)

It is provided herein that R, Rf, A, B, C, m', and n' are applied to only formula (surf-1), independent of their descriptions other than for the surfactant. R is a di- to tetra-valent $C_2$-$C_5$ aliphatic group. Exemplary divalent groups include ethylene, 1,4-butylene, 1,2-propylene, 2,2-dimethyl-1,3-propylene and 1,5-pentylene. Exemplary tri- and tetra-valent groups are shown below.

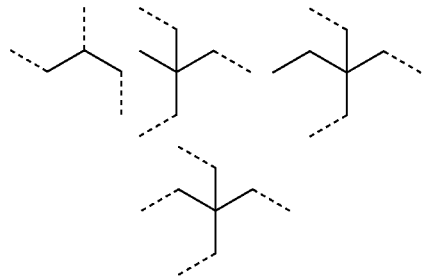

Herein the broken line denotes a valence bond. These formulae are partial structures derived from glycerol, trimethylol ethane, trimethylol propane, and pentaerythritol, respectively. Of these, 1,4-butylene and 2,2-dimethyl-1,3-propylene are preferably used.

Rf is trifluoromethyl or pentafluoroethyl, and preferably trifluoromethyl. The letter m' is an integer of 0 to 3, n' is an integer of 1 to 4, and the sum of m' and n', which represents the valence of R, is an integer of 2 to 4. A is equal to 1, B is an integer of 2 to 25, and C is an integer of 0 to 10. Preferably, B is an integer of 4 to 20, and C is 0 or 1. Note that the above structural formula does not prescribe the arrangement of respective constituent units while they may be arranged either in blocks or randomly. For the preparation of surfactants in the form of partially fluorinated oxetane ring-opened polymers, reference should be made to U.S. Pat. No. 5,650,483, for example.

Of the foregoing surfactants, FC-4430 (3M), Surflon S-381, Surfynol E1004, KH-20 and KH-30 (Asahi Glass Co., Ltd.), and oxetane ring-opened polymers of formula (surf-1) are preferred. These surfactants may be used alone or in admixture.

In the resist composition, the surfactant is preferably compounded in an amount of up to 2 parts, and especially up to 1 part by weight, per 100 parts by weight of the base resin. The amount of the surfactant, if added, is preferably at least 0.01 phr.

In one embodiment wherein the immersion lithography using water is applied to the resist composition of the invention, particularly in the absence of a resist protective film, the resist composition may have added thereto another surfactant having a propensity to segregate at the resist surface after spin coating for achieving a function of minimizing water penetration or leaching. The preferred other surfactant is a polymeric surfactant which is insoluble in water, but soluble in alkaline developer, and especially which is water repellent and enhances water slippage. Suitable polymeric surfactants are shown below.

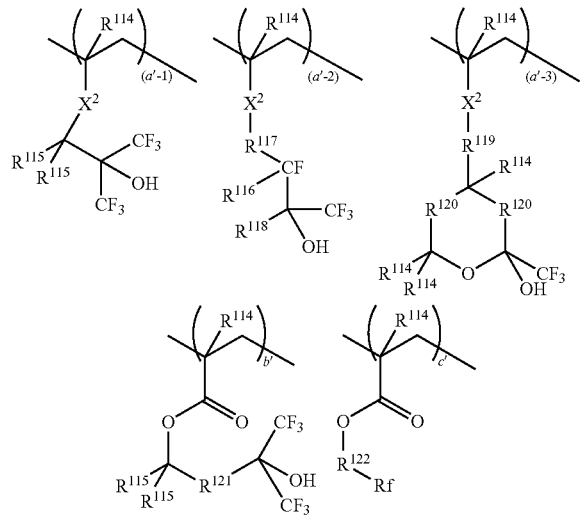

Herein $R^{114}$ is each independently hydrogen, fluorine, methyl or trifluoromethyl. $R^{115}$ is each independently hydrogen or a straight, branched or cyclic $C_1$-$C_{20}$ alkyl or fluoroalkyl group, or two $R^{115}$ in a common monomer may bond together to form a ring with the carbon atom to which they are attached, and in this event, they together represent a straight, branched or cyclic $C_2$-$C_{20}$ alkylene or fluoroalkylene group. $R^{116}$ is fluorine or hydrogen, or $R^{116}$ may bond with $R^{117}$ to form a non-aromatic ring of 3 to 10 carbon atoms in total with the carbon atom to which they are attached. $R^{111}$ is a straight, branched or cyclic $C_1$-$C_6$ alkylene group in which at least one hydrogen atom may be substituted by a fluorine atom. $R^{118}$ is a straight or branched $C_1$-$C_{10}$ alkyl group in which at least one hydrogen atom is substituted by a fluorine atom. Alternatively, $R^{117}$ and $R^{118}$ may bond together to form a non-aromatic ring with the carbon atoms to which they are attached. In this event, $R^{117}$, $R^{118}$ and the carbon atoms to which they are attached together represent a trivalent organic group of 2 to 12 carbon atoms in total. $R^{119}$ is a single bond or a $C_1$-$C_4$ alkylene. $R^{120}$ is each independently a single bond, —O—, or —$CR^{114}R^{114}$—. $R^{121}$ is a straight or branched $C_1$-$C_4$ alkylene group, or may bond with $R^{115}$ within a common monomer to form a $C_3$-$C_6$ non-aromatic ring with the carbon atom to which they are attached. $R^{122}$ is 1,2-ethylene, 1,3-propylene, or 1,4-butylene. Rf is a linear perfluoroalkyl group of 3 to 6 carbon atoms, typically 3H-perfluoropropyl, 4H-perfluorobutyl, 5H-perfluoropentyl, or 6H-perfluorohexyl. $X^2$ is each independently —C(=O)—O—, —O—, or —C(=O)—$R^{123}$— —C(=O)—O—. $R^{123}$ is a straight, branched or cyclic $C_1$-$C_{10}$ alkylene group. The subscripts are in the range: $0 \leq (a'-1) < 1$, $0 \leq (a'-2) < 1$, $0 \leq (a'-3) < 1$, $0 < (a'-1)+(a'-2)+(a'-3) < 1$, $0 \leq b' < 1$, $0 \leq c' < 1$, and $0 < (a'-1)+(a'-2)+(a'-3)+b'+c' \leq 1$.

In the chemically amplified resist composition of the invention, the polymeric surfactant is preferably formulated in an amount of 0.001 to 20 parts, and more preferably 0.01 to 10 parts by weight, per 100 parts by weight of the base resin. Reference should also be made to JP-A 2007-297590.

A further embodiment is a chemically amplified negative working resist composition comprising the inventive polymer. When used in this embodiment, the inventive polymer should contain recurring units having a substituent group capable of forming a crosslinked structure with an acid crosslinker, in addition to recurring units of formula (2). Examples of additional recurring units include, but are not limited to, those units derived from acrylic acid, methacrylic acid, hydroxystyrene (which may be substituted at any positions), and hydroxyvinylnaphthalene (which may be substituted at any positions).

Besides the inventive polymer, any alkali-soluble resins may be added. Examples of the alkali-soluble resin include poly(p-hydroxystyrene), poly(m-hydroxystyrene), poly(4-hydroxy-2-methylstyrene), poly(4-hydroxy-3-methylstyrene), poly(α-methyl-p-hydroxystyrene), partially hydrogenated p-hydroxystyrene copolymers, p-hydroxystyrene-α-methyl-p-hydroxystyrene copolymers, p-hydroxystyrene-α-methylstyrene copolymers, p-hydroxystyrene-styrene copolymers, p-hydroxystyrene-m-hydroxystyrene copolymers, p-hydroxystyrene-styrene copolymers, p-hydroxystyrene-acrylic acid copolymers, p-hydroxystyrene-methacrylic acid copolymers, p-hydroxystyrene-methyl methacrylate copolymers, p-hydroxystyrene-acrylic acid-methyl methacrylate copolymers, p-hydroxystyrene-methyl acrylate copolymers, p-hydroxystyrene-methacrylic acid-methyl methacrylate copolymers, poly(methacrylic acid), poly (acrylic acid), acrylic acid-methyl acrylate copolymers, methacrylic acid-methyl methacrylate copolymers, acrylic acid-maleimide copolymers, methacrylic acid-maleimide copolymers, p-hydroxystyrene-acrylic acid-maleimide copolymers, and p-hydroxystyrene-methacrylic acid-maleimide copolymers, but are not limited to these combinations.

The inventive polymer and the other alkali-soluble resin are preferably blended in a weight ratio from 100:0 to 10:90, more preferably from 100:0 to 20:80. If the blend ratio of the inventive polymer is below this range, the resist composition would become poor in some of the desired properties. The properties of the resist composition can be adjusted by properly changing the blend ratio of the inventive polymer.

Notably, the alkali-soluble resin is not limited to one type and a mixture of two or more resins may be added. The use of plural resins allows for easy adjustment of resist properties.

Crosslinker

Formulated in the negative resist composition is an acid crosslinker (F) which forms a crosslinked structure under the action of acid. Typical crosslinkers are compounds having at least two hydroxymethyl, alkoxymethyl, epoxy or vinyl ether groups within a molecule. Substituted glycoluril derivatives, urea derivatives, and hexa(methoxymethyl)melamine compounds are suitable as the acid crosslinker. Examples include N,N,N',N'-tetramethoxymethylurea, hexamethoxymethylmelamine, tetraalkoxymethyl-substituted glycoluril compounds such as tetrahydroxymethyl-substituted glycoluril and tetramethoxymethylglycoluril, and condensates of phenolic compounds such as substituted or unsubstituted bis (hydroxymethylphenol) compounds and bisphenol A with epichlorohydrin. Especially preferred crosslinkers are 1,3,5, 7-tetraalkoxymethylglycolurils such as 1,3,5,7-tetramethoxymethylglycoluril, 1,3,5,7-tetrahydroxymethylglycoluril, 2,6-dihydroxymethyl-p-cresol, 2,6-dihydroxymethylphenol, 2,2',6,6'-tetrahydroxymethyl-bisphenol A, 1,4-bis[2-(2-hydroxypropyl)]benzene, N,N,N', N'-tetramethoxymethylurea, and hexamethoxymethylmelamine.

In the chemically amplified resist composition, an appropriate amount of the acid crosslinker (F) is, though not limited thereto, 1 to 20 parts, and especially 5 to 15 parts by weight per 100 parts by weight of the base resin. The crosslinkers may be used alone or in admixture of two or more.

While the resist composition of the invention typically comprises a polymer or base resin, acid generator, organic solvent and quencher as described above, there may be added optional other ingredients such as surfactants and crosslinkers, as well as dissolution inhibitors, acidic compounds, stabilizers, and dyes. Optional ingredients may be added in conventional amounts so long as this does not compromise the objects of the invention.

In forming a pattern from the resist composition of the invention, any well-known lithography may be employed. For example, the composition is applied onto a substrate for integrated circuitry fabrication (e.g., Si, $SiO_2$, SiN, SiON, TiN, WSi, BPSG, SOG, organic antireflective coating, etc.) or a substrate for mask circuitry fabrication (e.g., Cr, CrO, CrON, MoSi, etc.) by a suitable coating technique such as spin coating. The coating is prebaked on a hot plate at a temperature of 60 to 150° C. for 1 to 10 minutes, preferably 80 to 140° C. for 1 to 5 minutes, to form a resist film of 0.05 to 2.0 µm thick. A patterning mask having the desired pattern is then placed over the resist film, and the film exposed through the mask to an electron beam or to high-energy radiation such as deep-UV, excimer laser or x-ray in a dose of 1 to 200 $mJ/cm^2$, and preferably 10 to 100 $mJ/cm^2$. Alternatively, pattern formation may be performed by writing with an electron beam directly (not through a mask). Light exposure may be done by a conventional exposure process or in some cases, by an immersion process of providing liquid impregnation between the mask and the resist. In the case of immersion lithography, a protective coating which is insoluble in water may be used. The resist film is then post-exposure baked (PEB) on a hot plate at 60 to 150° C. for 1 to 5 minutes, and preferably at 80 to 140° C. for 1 to 3 minutes. Finally, development is carried out using as the developer an aqueous alkali solution, such as a 0.1 to 5 wt %, preferably 2 to 3 wt %, aqueous solution of tetramethylammonium hydroxide (TMAH), this being done by a conventional method such as dip, puddle, or spray development for a period of 0.1 to 3 minutes, and preferably 0.5 to 2 minutes. These steps result in the formation of the desired pattern on the substrate. Of the various types of high-energy radiation that may be used, the resist composition of the invention is best suited to fine pattern formation with, in particular, deep-UV having a wavelength of 250 to 190 nm, excimer laser, x-ray, or electron beam. The desired pattern may not be obtainable outside the upper and lower limits of the above range.

The water-insoluble protective coating which is used in the immersion lithography is to prevent the resist coating from being leached and to improve water slippage at the coating surface and is generally divided into two types. The first type is an organic solvent-strippable protective coating which must be stripped, prior to alkaline development, with an organic solvent in which the resist coating is not dissolvable. The second type is an alkali-soluble protective coating which is soluble in an alkaline developer so that it can be removed simultaneously with the removal of solubilized areas of the resist coating. The protective coating of the second type is preferably of a material comprising a polymer having a 1,1,1,3,3,3-hexafluoro-2-propanol residue (which is insoluble in water and soluble in an alkaline developer) as a base in an alcohol solvent of at least 4 carbon atoms, an ether solvent of 8 to 12 carbon atoms or a mixture thereof. Alternatively, the aforementioned surfactant which is insoluble in water and soluble in an alkaline developer may be dissolved in an alcohol solvent of at least 4 carbon atoms, an ether solvent of 8 to 12 carbon atoms or a mixture thereof to form a material from which the protective coating of the second type is formed.

Any desired step may be added to the pattern forming process. For example, after a photoresist coating is formed, a step of rinsing with pure water (post-soaking) may be introduced to extract the acid generator or the like from the coating surface or wash away particles. After exposure, a step of rinsing (post-soaking) may be introduced to remove any water remaining on the coating after exposure.

EXAMPLE

Examples and Comparative Examples are given below by way of illustration and not by way of limitation.

Sulfonium salts having a polymerizable anion within the scope of the invention were synthesized according to the following formulation.

Synthesis Example 1-1

Synthesis of Triphenylsulfonium Chloride

Diphenyl sulfoxide, 40 g (0.2 mole), was dissolved in 400 g of dichloromethane, which was stirred under ice cooling. At a temperature below 20° C., 65 g (0.6 mole) of trimethylsilyl chloride was added dropwise to the solution, which was allowed to mature for 30 minutes at the temperature. Then, a Grignard reagent which had been prepared from 14.6 g (0.6 mole) of metallic magnesium, 67.5 g (0.6 mole) of chlorobenzene and 168 g of tetrahydrofuran (THF) was added dropwise at a temperature below 20° C. The reaction solution was allowed to mature for one hour, after which 50 g of water at a temperature below 20° C. was added to quench the reaction. To this solution, 150 g of water, 10 g of 12N hydrochloric acid, and 200 g of diethyl ether were further added. The water layer was separated and washed with 100 g of diethyl ether, yielding an aqueous solution of triphenylsulfonium chloride. The compound in aqueous solution form was used in the subsequent reaction without further isolation.

Synthesis Example 1-2

Synthesis of 4-tert-butylphenyldiphenylsulfonium bromide

The target compound was obtained by following the procedure of Synthesis Example 1-1 aside from using 4-tert-butylbromobenzene instead of the chlorobenzene in Synthesis Example 1 and increasing the amount of water for extraction.

Synthesis Example 1-3

Synthesis of 4-tert-butoxyphenyldiphenylsulfonium chloride

The target compound was obtained by following the procedure of Synthesis Example 1-1 aside from using 4-tert-butoxychlorobenzene instead of the chlorobenzene in Synthesis Example 1-1, using dichloromethane containing 5 wt % of triethylamine as the solvent, and increasing the amount of water for extraction.

Synthesis Example 1-4

Synthesis of tris(4-methylphenyl)sulfonium chloride

The target compound was obtained by following the procedure of Synthesis Example 1-1 aside from using bis(4- methylphenyl) sulfoxide instead of the diphenyl sulfoxide and 4-chlorotoluene instead of the chlorobenzene in Synthesis Example 1-1, and increasing the amount of water for extraction.

Synthesis Example 1-5

Synthesis of tris(4-tert-butylphenyl)sulfonium bromide

The target compound was obtained by following the procedure of Synthesis Example 1-1 aside from using bis(4-tert-butylphenyl) sulfoxide instead of the diphenyl sulfoxide and 4-tert-butylbromobenzene instead of the chlorobenzene in Synthesis Example 1-1, and increasing the amount of water for extraction.

Synthesis Example 1-6

Synthesis of bis(4-tert-butylphenyl)iodonium hydrogen sulfate

A mixture of 84 g (0.5 mole) of tert-butylbenzene, 53 g (0.25 mole) of potassium iodate and 50 g of acetic anhydride was stirred under ice cooling. A mixture of 35 g of acetic anhydride and 95 g of conc. sulfuric acid was added dropwise thereto at a temperature below 30° C. The resulting solution was allowed to mature for 3 hours at room temperature and ice cooled again, after which 250 g of water was added dropwise to quench the reaction. The reaction solution was extracted with 400 g of dichloromethane. The organic layer was discolored by adding 6 g of sodium hydrogen sulfite. The organic layer was washed three times with 250 g of water. The washed organic layer was concentrated in vacuum, obtaining a crude target product. The product was used in the subsequent reaction without further purification.

Synthesis Example 1-7

Synthesis of Dimethylphenylsulfonium Sulfate

At room temperature, 6.2 g (0.05 mole) of thioanisole and 6.9 g (0.055 mole) of dimethyl sulfate were stirred for 12 hours. 100 g of water and 50 ml of diethyl ether were added to the reaction solution. The aqueous layer was taken out, which was an aqueous solution of the target compound, dimethylphenylsulfonium sulfate.

Synthesis Example 1-8

Synthesis of Phenacyltetrahydrothiophenium Bromide

In 220 g of nitromethane were dissolved 88.2 g (0.44 mole) of phenacyl bromide and 39.1 g (0.44 mole) of tetrahydrothiophene. The solution was stirred for 4 hours at room temperature. 800 g of water and 400 g of diethyl ether were added to the reaction solution. The aqueous layer was taken out, which was an aqueous solution of the target compound, phenacyltetrahydrothiophenium bromide.

Synthesis Example 1-9

Synthesis of sodium 2-(pivaloyloxy)-1,1-difluoroethane-sulfonate [Anion 1]

Pivalic chloride and 2-bromo-2,2-difluoroethanol were mixed in tetrahydrofuran and ice cooled. Triethylamine was added to the mixture, from which 2-bromo-2,2-difluoroethyl pivalate was obtained by standard separatory operation and solvent distillation. The compound was reacted with sodium dithionite to form sodium sulfinate and oxidized with hydrogen peroxide, obtaining the target compound, sodium 2-(pivaloyloxy)-1,1-difluoroethanesulfonate.

The synthesis of carboxylate is well known, and the synthesis of sulfinic acid and sulfonic acid from alkyl halides is well known. The latter is described, for example, in JP-A 2004-2252.

Synthesis Example 1-10

Synthesis of triphenylsulfonium 2-(pivaloyloxy)-1,1-difluoroethanesulfonate

In 700 g of dichloromethane and 400 g of water were dissolved 159 g (0.37 mole) of sodium 2-(pivaloyloxy)-1,1-difluoroethanesulfonate (purity 63%) and 132 g (0.34 mole) of triphenylsulfonium iodide. The organic layer was separated and washed three times with 200 g of water. The organic layer was concentrated and diethyl ether was added to the residue for recrystallization. The target compound was obtained as white crystals, 164 g (yield 95%).

Synthesis Example 1-11

Synthesis of 4-tert-butylphenyldiphenylsulfonium 2-(pivaloyloxy)-1,1-difluoroethanesulfonate In 150 g of dichloromethane were dissolved 20 g (0.052 mole) of sodium 2-(pivaloyloxy)-1,1-difluoroethanesulfonate (purity 70%) and 217 g (0.052 mole) of 4-tert-butylphenyl-diphenylsulfonium bromide in water. The organic layer was separated and washed three times with 50 g of water. The organic layer was concentrated and diethyl ether was added to the residue for recrystallization. The target compound was obtained as white crystals, 26 g (yield 79%).

Synthesis Example 1-12

Synthesis of triphenylsulfonium 1,1-difluoro-2-hydroxy-ethanesulfonate [PAG1]

In 760 g of methanol was dissolved 243.5 g (0.48 mole) of triphenylsulfonium 2-(pivaloyloxy)-1,1-difluoroethane-sulfonate. To this solution under ice cooling, an aqueous sodium hydroxide solution (40 g sodium hydroxide in 120 g water) was added dropwise at a temperature below 5° C. The reaction solution was allowed to mature at room temperature for 8 hours, and dilute hydrochloric acid (99.8 g 12N hydrochloric acid in 200 g water) was added thereto at a temperature below 10° C. to quench the reaction. The methanol was distilled off in vacuum. To the residue was added 1,000 g of dichloromethane. The organic layer was washed three times with 30 g of saturated saline and concentrated. Diisopropyl ether, 1 L, was added to the concentrate for crystallization. The crystals were filtered and dried, obtaining the target compound (PAG1), 187 g (purity 78%, net yield 78%). PAG1 has the following structure.

PAG 1

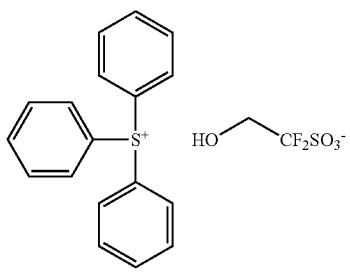

Synthesis Example 1-13

Synthesis of triphenylsulfonium 1,1-difluoro-2-hydroxy-ethanesulfonate [PAG1]

In 200 g of methanol was dissolved 50.9 g (0.1 mole) of triphenylsulfonium 2-(pivaloyloxy)-1,1-difluoroethane-sulfonate. To this solution under ice cooling, 2.0 g of a 28 wt % methanol solution of sodium methoxide was added. The reaction solution was allowed to mature at room temperature for 24 hours, and 1.0 g of 12N hydrochloric acid was added thereto at a temperature below 10° C. to quench the reaction. The methanol was distilled off in vacuum. To the residue was added 250 g of dichloromethane. After the inorganic salt was filtered off, the filtrate was concentrated. Diisopropyl ether, 150 g, was added to the concentrate for crystallization. The crystals were filtered and dried, obtaining the target compound (PAG1), 42 g (purity 99%, net yield 99%).

Synthesis Examples 1-14 to 1-20

Target compounds were synthesized as in Synthesis Examples 1-10 and 1-12 except that the sulfonium or iodonium salts prepared in Synthesis Examples 1-2 to 1-8 were used. The resulting onium salts PAG2 to PAG8 are shown below.

PAG 2

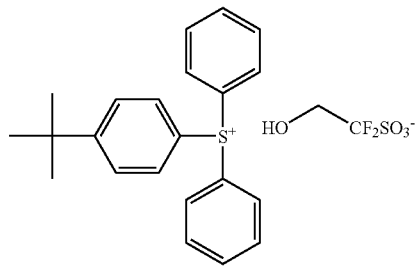

PAG 3

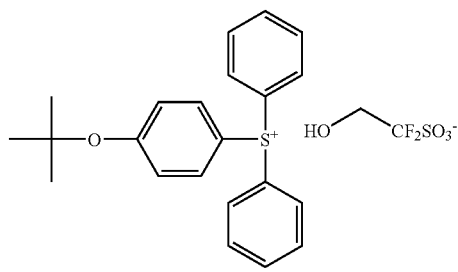

PAG 4

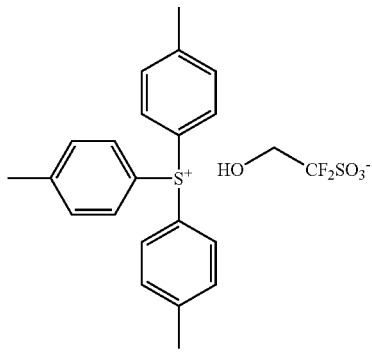

PAG 5

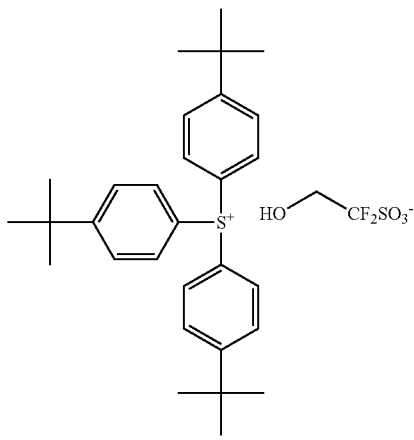

PAG 6

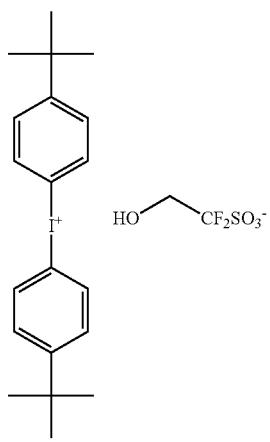

PAG 7

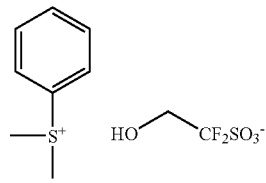

PAG 8

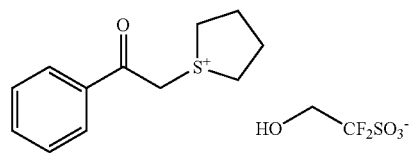

Synthesis Example 1-21

Synthesis of triphenylsulfonium 1,1-difluoro-2-(3-methacryloyloxy-adamantane-1-carbonyloxy)-ethane-1-sulfonate [Monomer 1]

In toluene medium, 3-methacryloyloxyadamantane-carboxylic acid was reacted with oxalyl chloride to form a corresponding carboxylic acid chloride.

To 3.3 g (11 mmol) of the 3-methacryloyloxyadamantane-carbonyl chloride were added 4.2 g (10 mmol) of triphenylsulfonium 1,1-difluoro-2-hydroxyethanesulfonate in Synthesis Example 1-13 and 20 g of methylene chloride. To the mixture under ice cooling, a solution containing 1.1 g (11 mmol) of triethylamine and 0.25 g (2 mmol) of N,N-dimethylaminopyridine in 5 g of methylene chloride was added at a temperature below 5° C., and the resulting mixture was stirred for 2 hours at room temperature. Thereafter, 11 g of 5% dilute hydrochloric acid was added to the reaction mixture. The organic layer was taken out and washed with water, from which methylene chloride was distilled off in vacuum. 30 g of methyl isobutyl ketone was added to the residue, from which the residual water was distilled off in vacuum together with methyl isobutyl ketone. Diethyl ether was added to the residue for recrystallization. The resulting crystals were recovered and dried, obtaining the target compound, triphenylsulfonium 1,1-difluoro-2-(3-methacryloyloxy-adamantane-1-carbonyloxy)-ethane-1-sulfonate. White crystals, 5.5 g (yield 82%). The compound has the following structure.

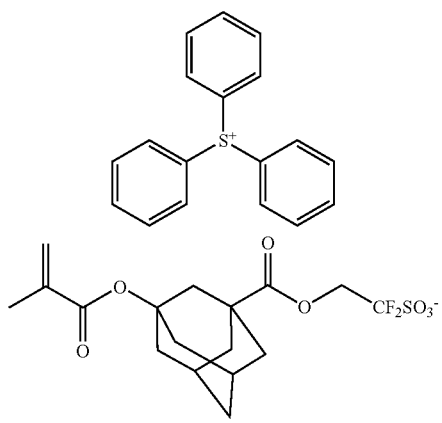

Figure 2:
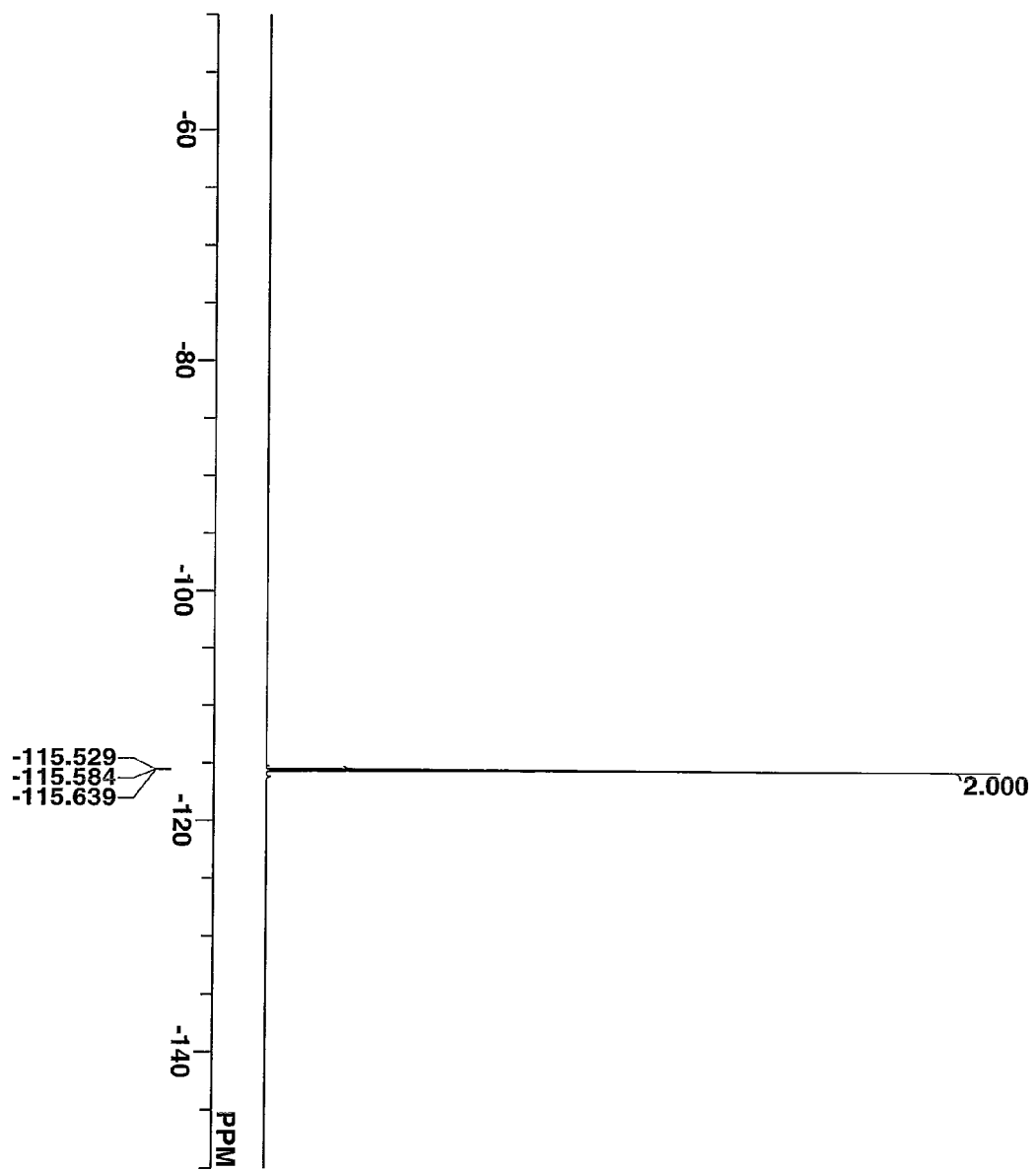
FIG. 2 is a diagram showing the ¹⁹F-NMR spectrum of Monomer 1 in Synthesis Example 1-21.

The compound was analyzed by spectroscopy. The nuclear magnetic resonance spectra, $^1$H-NMR and $^{19}$F-NMR/DMSO-$d_6$ are shown in FIGS. 1 and 2. Note that in $^1$H-NMR, traces of residual solvents (dichloromethane, methyl isobutyl ketone, water) were observed. The data of time-of-flight mass spectrometry (TOFMS) are also shown.

IR spectrum (KBr, cm$^{-1}$)

2942, 2927, 2861, 1731, 1708, 1635, 1479, 1448, 1375, 1328, 1303, 1274, 1261, 1232, 1178, 1151, 1135, 1103, 1087, 1024, 1010, 995, 950, 765, 750, 682, 644, 549, 530, 514, 499

TOFMS (MALDI)

Positive M$^+$263 (corresponding to $(C_6H_5)_3S^+$)

Negative M$^-$407 (corresponding to $CH_2(OCO-C_{14}H_{19}O_2)CF_2SO_3^-$)

Synthesis Example 1-22

Synthesis of triphenylsulfonium 1,1-difluoro-2-(9-methacryloyloxy-4-oxo-5-oxatricyclo[4.2.1.0$^{3,7}$]-non-2-ylcarbonyloxy)-ethane-1-sulfonate [Monomer 2]

In toluene medium, 2-methacryloyloxy-5-oxo-4-oxa-tricyclo[4.2.1.0$^{3,7}$]-nonane-9-carboxylic acid was reacted with oxalyl chloride to form a corresponding carboxylic acid chloride.

To 2.8 g (10 mmol) of the 2-methacryloyloxy-5-oxo-4-oxa-tricyclo[4.2.1.0$^{3,7}$]-non-9-ylcarbonyl chloride were added 4.2 g (10 mmol) of triphenylsulfonium 1,1-difluoro-2-hydroxy-ethanesulfonate in Synthesis Example 1-13 and 20 g of methylene chloride. To the mixture under ice cooling, a solution containing 1.0 g (10 mmol) of triethylamine and 0.25 g (2 mmol) of N,N-dimethylaminopyridine in 5 g of methylene chloride was added at a temperature below 5° C., and the resulting mixture was stirred for 2 hours at room temperature. Thereafter, 11 g of 5% dilute hydrochloric acid was added to the reaction mixture. The organic layer was taken out and washed with water, from which methylene chloride was distilled off in vacuum. 30 g of methyl isobutyl ketone was added to the residue, from which the residual water was distilled off in vacuum together with methyl isobutyl ketone. The resulting residue was purified by silica gel chromatography, obtaining the target compound, triphenylsulfonium 1,1-difluoro-2-(9-methacryloyloxy-4-oxo-5-oxatricyclo[4.2.1.0$^{3,7}$]-non-2-ylcarbonyloxy)-ethane-1-sulfonate. Colorless solids, 4.0 g (yield 61%). The compound has the following structure.

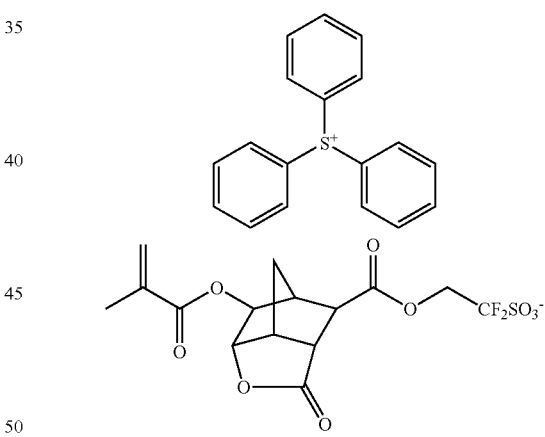

Figure 3:
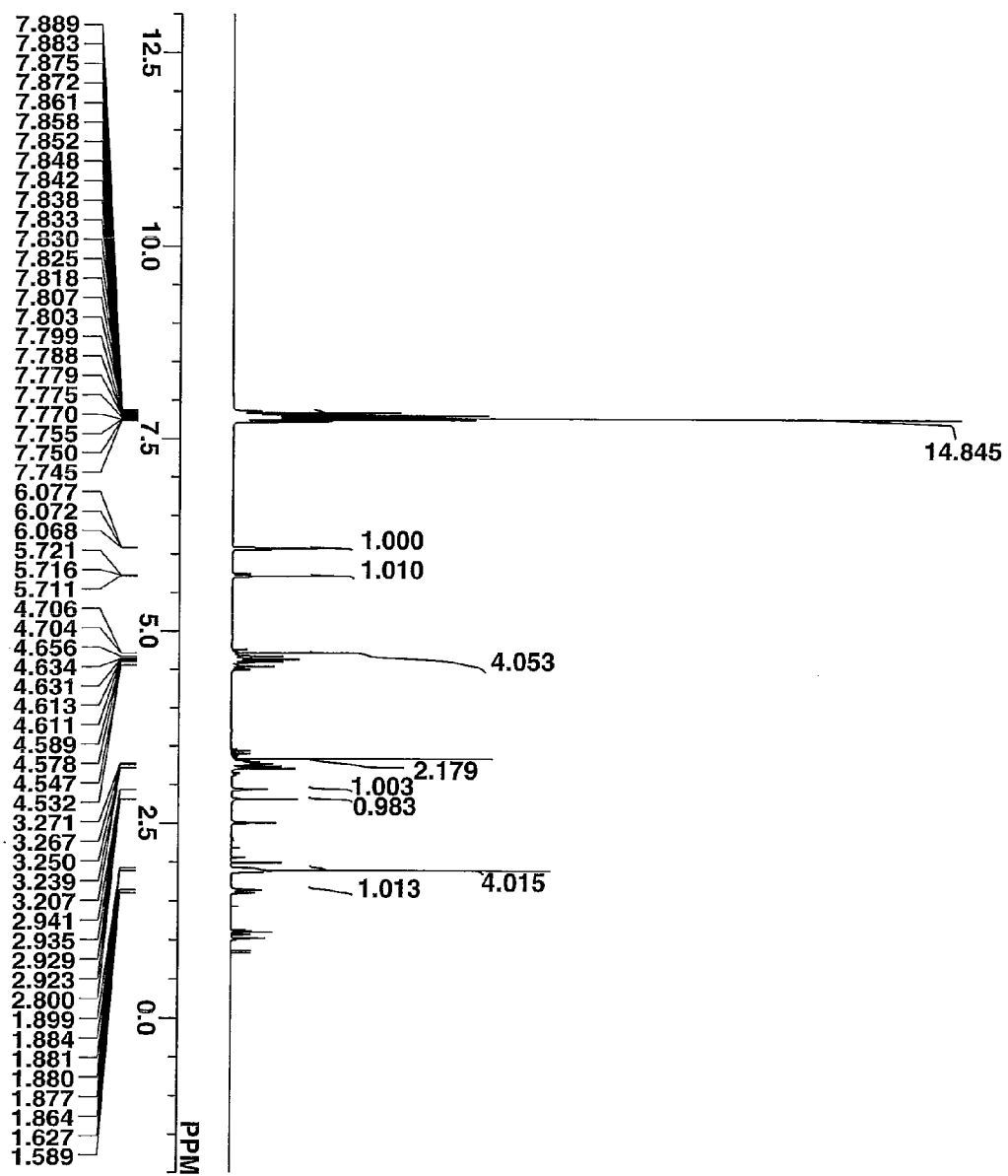
FIG. 3 is a diagram showing the ¹H-NMR spectrum of Monomer 2 in Synthesis Example 1-22.
Figure 4:
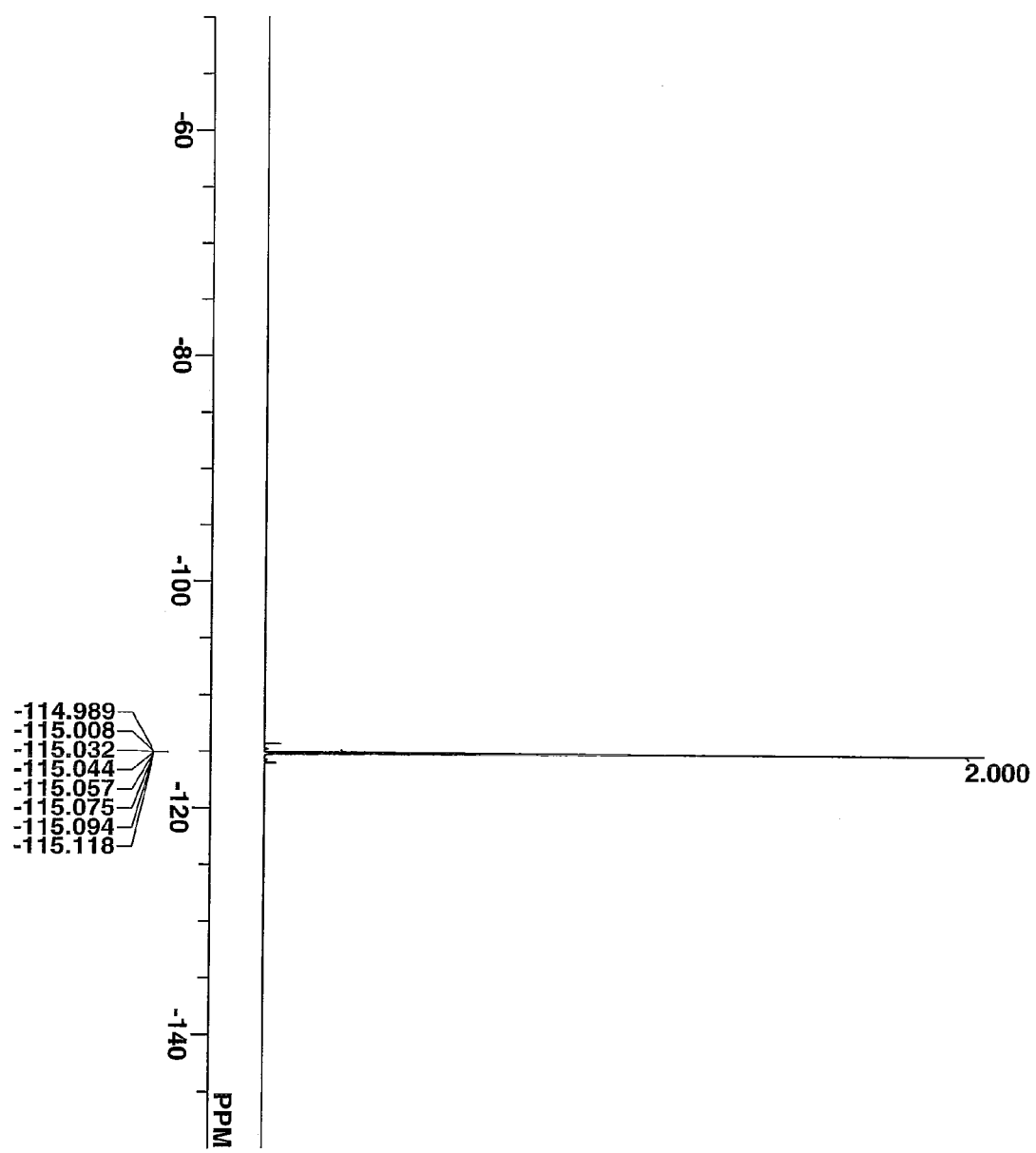
FIG. 4 is a diagram showing the ¹⁹F-NMR spectrum of Monomer 2 in Synthesis Example 1-22.

The compound was analyzed by spectroscopy. The $^1$H-NMR and $^{19}$F-NMR/DMSO-$d_6$ are shown in FIGS. 3 and 4. Note that in $^1$H-NMR, traces of residual solvents (methylene chloride, methyl isobutyl ketone, diisopropyl ether, water) were observed. The data of time-of-flight mass spectrometry (TOFMS) are also shown.

IR spectrum (KBr, cm$^{-1}$)

1785, 1747, 1718, 1635, 1477, 1448, 1382, 1340, 1321, 1255, 1157, 1112, 1066, 1016, 997, 946, 929, 750, 684, 642, 549, 522, 501

TOFMS (MALDI)

Positive M$^+$263 (corresponding to $(C_6H_5)_3S^+$)

Negative M$^-$409 (corresponding to $CH_2(OCO-C_{12}H_{13}O_4)CF_2SO_3^-$)

Synthesis Example 1-23

Synthesis of triphenylsulfonium 1,1-difluoro-2-(4-vinyl-benzoyloxy)-ethane-1-sulfonate [Monomer 3]

In toluene medium, 4-vinylbenzoic acid was reacted with oxalyl chloride to form a corresponding carboxylic acid chloride.

Under ice cooling, 2.0 g (12 mmol) of the 4-vinylbenzoyl chloride in methylene chloride was added dropwise to a mixture of 4.2 g (10 mmol) of triphenylsulfonium 1,1-difluoro-2-hydroxyethanesulfonate in Synthesis Example 1-13, 1.21 g (12 mmol) of triethylamine, 0.24 g (2 mmol) of N,N-dimethylaminopyridine, and 20 g of methylene chloride. The resulting mixture was stirred for 2 hours at room temperature. Thereafter, 11 g of 5% dilute hydrochloric acid was added to the reaction mixture. The organic layer was taken out and washed with water, from which methylene chloride was distilled off in vacuum. 30 g of methyl isobutyl ketone was added to the residue, which was washed with dilute aqueous ammonia and then with water. Thereafter, methyl isobutyl ketone was distilled off in vacuum. Diisopropyl ether was added to the residue. By decantation, the target compound, triphenylsulfonium 1,1-difluoro-2-(4-vinyl-benzoyloxy)-ethane-1-sulfonate was obtained. Colorless oil, 5.1 g (yield 86%). The compound has the following structure.

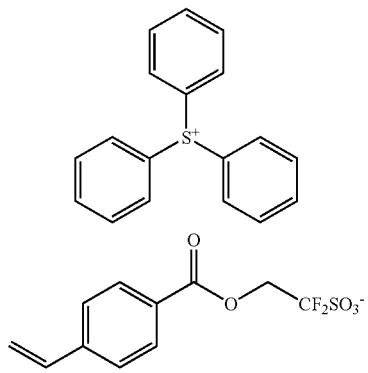

Figure 5:
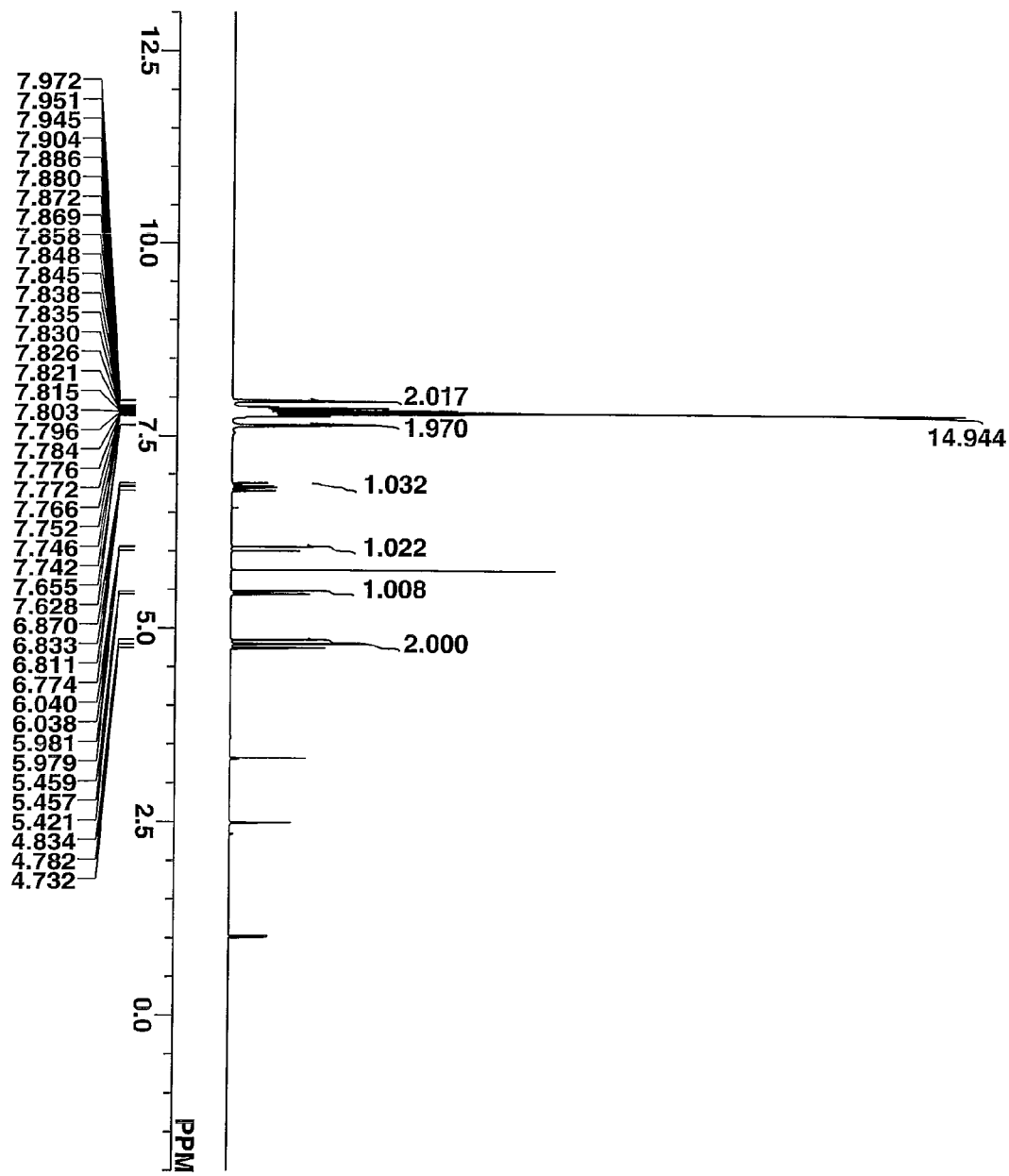
FIG. 5 is a diagram showing the ¹H-NMR spectrum of Monomer 3 in Synthesis Example 1-23.
Figure 6:
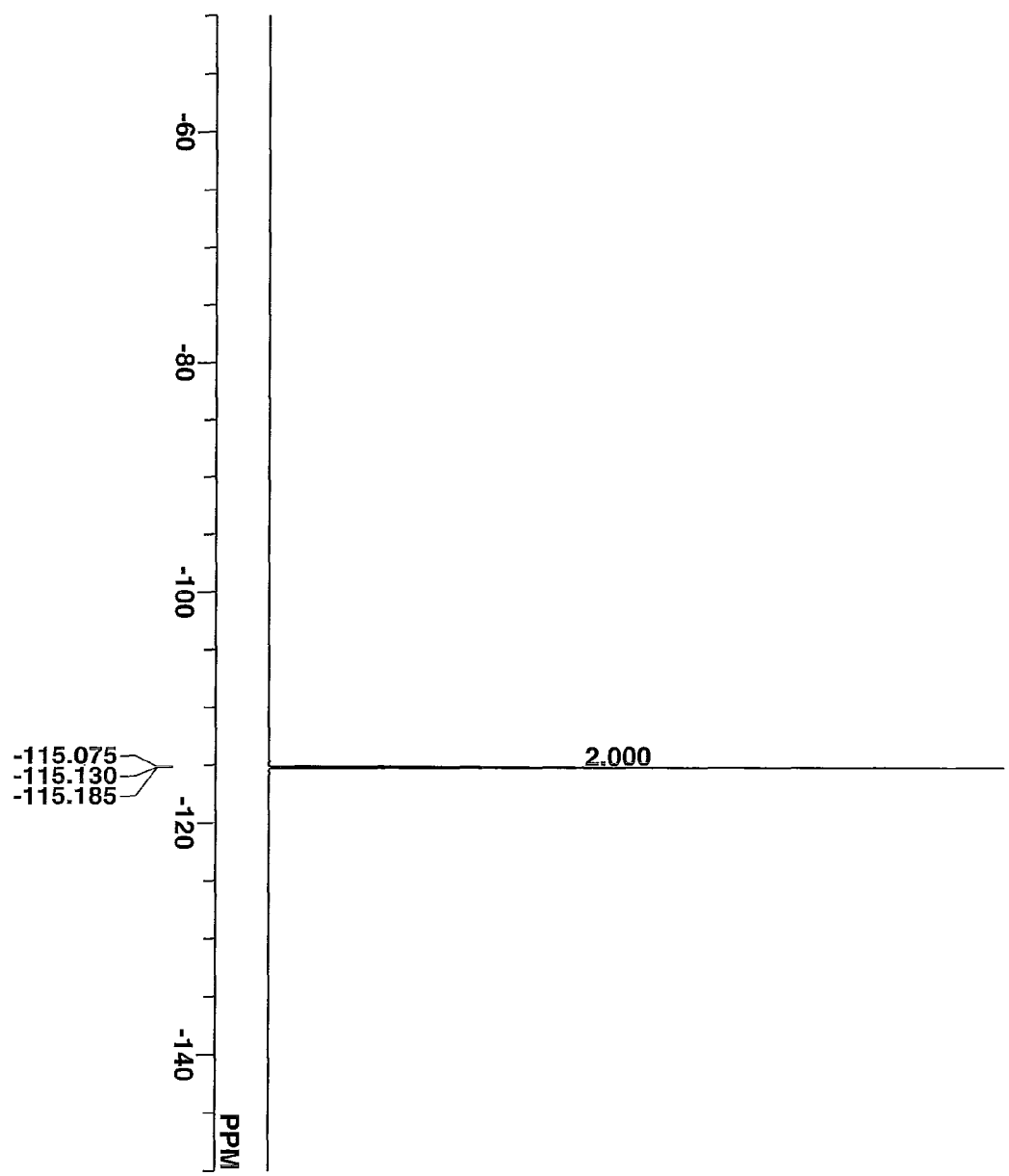
FIG. 6 is a diagram showing the ¹⁹F-NMR spectrum of Monomer 3 in Synthesis Example 1-23.

The compound was analyzed by spectroscopy. The $^1$H-NMR and $^{19}$F-NMR/DMSO-$d_6$ are shown in FIGS. 5 and 6. Note that in $^1$H-NMR, traces of residual solvents (methylene chloride, diisopropyl ether, water) were observed. The data of time-of-flight mass spectrometry (TOFMS) are also shown.

IR spectrum (D-ATR, cm$^{-1}$)
3086, 3061, 1719, 1606, 1475, 1446, 1235, 1178, 1101, 1031, 1006, 995, 966, 933, 861, 781, 745, 713, 700, 681, 640, 611, 584

TOFMS (MALDI)
Positive M$^+$263 (corresponding to (C$_6$H$_5$)$_3$S$^+$)
Negative M$^-$291 (corresponding to CH$_2$(OCO—C$_8$H$_7$)CF$_2$SO$_3^-$)

Analogous compounds were synthesized by following the procedure of Synthesis Examples 1-21, 1-22 and 1-23 aside from using one of PAG2 to PAG8 instead of PAG1, i.e., triphenylsulfonium 1,1-difluoro-2-hydroxyethanesulfonate. The compounds correspond to Monomers 1, 2 and 3 wherein the cation is replaced by 4-tert-butylphenyldiphenylsulfonium, 4-tert-butoxyphenyldiphenylsulfonium, tris(4-methylphenyl)-sulfonium, tris(4-tert-butylphenyl)sulfonium, bis(4-tert-butylphenyl)iodonium, dimethylphenylsulfonium, and phenacyltetrahydrothiophenium.

Polymers within the scope of the invention were synthesized according to the following formulation.

Synthesis Example 2-1

Synthesis of Polymer 1

A flask under a nitrogen blanket was charged with 2.55 g of triphenylsulfonium 1,1-difluoro-2-(3-methacryloyloxy-adamantane-1-carbonyloxy)-ethane-1-sulfonate, 3.13 g 4-ethyl-4-exo-tetracyclo[6.2.1.1$^{3,6}$.0$^{2,7}$]dodec-4-yl methacrylate, 2.59 g of 5-oxotetrahydrofuran-3-yl methacrylate, 1.80 g of 3-hydroxy-1-adamantyl methacrylate, 0.31 g of 2,2'-azobisisobutyronitrile, and 18.2 g of 1-methoxy-2-propanol, to form a monomer solution. Another flask under a nitrogen blanket was charged with 6.0 g of 1-methoxy-2-propanol, which was heated to 80° C. with stirring and to which the monomer solution was added dropwise over 4 hours. After the completion of dropwise addition, the polymerization solution was stirred for 2 hours while keeping the temperature of 80° C. It was then cooled to room temperature. The polymerization solution was added dropwise to 100 g of hexane, after which the precipitated copolymer was filtered. The copolymer was washed twice with 60 g of hexane and then dried in vacuum at 50° C. for 20 hours. The copolymer was obtained in white powder solid form (9.41 g, yield 93%). It is designated Polymer 1, having the following formula.

Polymer 1

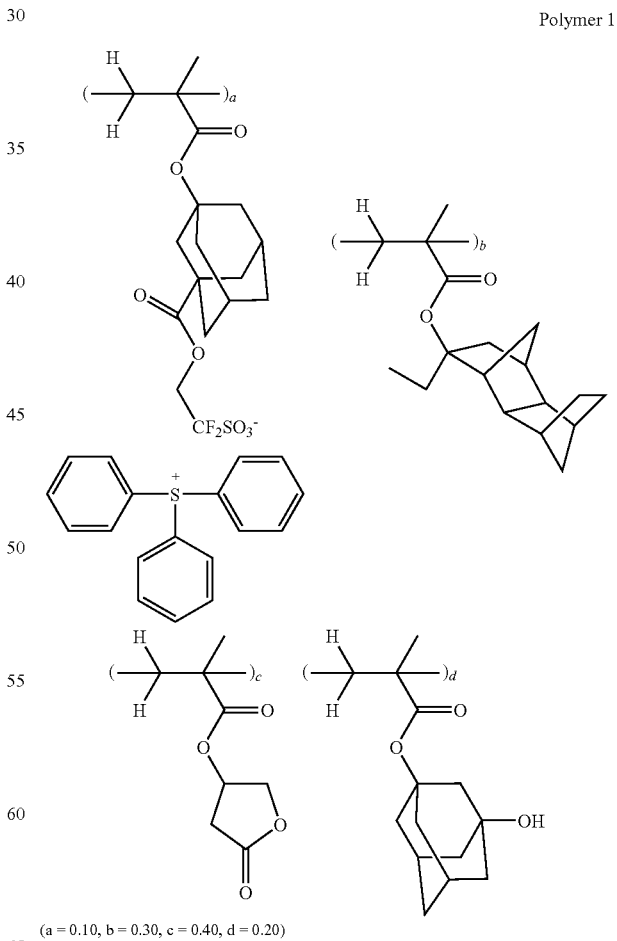

(a = 0.10, b = 0.30, c = 0.40, d = 0.20)

Synthesis Examples 2-2 to 2-4

Synthesis of Polymers 2 to 4

Resins shown in Table 1 were prepared by the same procedure as Synthesis Example 2-1 except that the type and proportion of monomers were changed. The structure of the units in Table 1 is shown in Tables 2 to 6. Note that the ratio of incorporated units in Table 1 is expressed in a molar ratio.

Synthesis Example 2-5

Synthesis of Polymer 5

A flask under a nitrogen blanket was charged with 2.55 g of triphenylsulfonium 1,1-difluoro-2-(2-methacryloyloxy-5-oxo-4-oxa-tricyclo[4.2.1.0$^{3,7}$]-nonane-9-carbonyloxy)-ethane-1-sulfonate, 3.13 g 4-ethyl-4-exo-tetracyclo[6.2.1.1$^{3,6}$.0$^{2,7}$]-dodec-4-yl methacrylate, 2.54 g of 5-oxo-4,8-dioxatricyclo-[4.2.1.0$^{3,7}$]-non-2-yl methacrylate, 2.68 g of 3-hydroxy-1-adamantyl methacrylate, 0.31 g of 2,2'-azobisisobutyro-nitrile, and 19.6 g of methyl ethyl ketone (MEK), to form a monomer solution. Another flask under a nitrogen blanket was charged with 6.6 g of MEK, which was heated to 80° C. with stirring and to which the monomer solution was added dropwise over 4 hours. After the completion of dropwise addition, the polymerization solution was stirred for 2 hours while keeping the temperature of 80° C. It was then cooled to room temperature. The polymerization solution was added dropwise to a mixture of 10 g of MEK and 90 g of hexane, after which the precipitated copolymer was filtered. The copolymer was washed twice with a solvent mixture of 18.5 g of MEK and 41.5 g of hexane and then dried in vacuum at 50° C. for 20 hours. The copolymer was obtained in white powder solid form (9.81 g, yield 90%). It is designated Polymer 5, having the following formula.

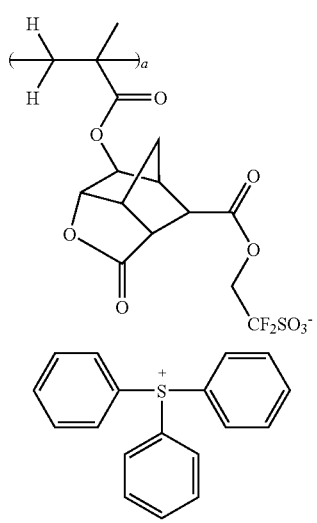

Polymer 5

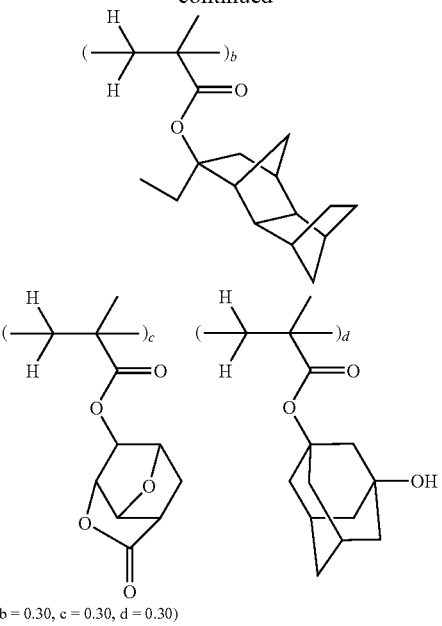

(a = 0.10, b = 0.30, c = 0.30, d = 0.30)

Synthesis Examples 2-6 to 2-22, 2-29, 2-30 and Comparative Synthesis Examples 1-1 to 1-2

Synthesis of Polymers 6 to 22, 29, 30, 33 and 34

Resins shown in Table 1 were prepared by the same procedure as Example 2-5 except that the type and proportion of monomers were changed. The structure of the units in Table 1 is shown in Tables 2 to 6. Note that the ratio of incorporated units in Table 1 is expressed in a molar ratio.

Synthesis Examples 2-23 to 2-26 and Comparative Synthesis Example 1-3

Synthesis of Polymers 23 to 26 and 31

Each of Polymers 23 to 26 and 31 was obtained by preparing a polymer (Polymers 18 to 22) according to the formulation described above and dissolving it in a solvent mixture of methanol and tetrahydrofuran. Oxalic acid was added to the solution whereupon deprotection reaction was allowed to run at 40° C. The reaction solution was neutralized with pyridine and purified by routine re-precipitation, obtaining a polymer having hydroxystyrene units.

Synthesis Examples 2-27, 2-28, 2-31 and 2-32 and Comparative Synthesis Example 1-4

Synthesis of Polymers 27, 28, 32, 35 and 36

Polymers 25, 26 and 23 were reacted with 1-chloro-1-methoxy-2-methylpropane under basic conditions, obtaining the target Polymers 27, 28 and 32. Polymers 35 and 36 could be similarly produced except that the PAG was changed.

With respect to the deprotection and protection of polyhydroxystyrene derivatives in Synthesis Examples 2-18 to 2-28 and Comparative Synthesis Examples 1-3 and 1-4, reference should be made to JP-A 2004-115630 and JP-A 2005-8766.

TABLE 1

|  |  | Resin | Unit 1 (ratio) | Unit 2 (ratio) | Unit 3 (ratio) | Unit 4 (ratio) | Unit 5 (ratio) | Unit 6 (ratio) |
|---|---|---|---|---|---|---|---|---|
| Synthesis Example | 2-1 | Polymer 1 | PM-1M(0.10) | A-1M(0.30) | B-6M(0.40) | B-1M(0.20) | — | — |
|  | 2-2 | Polymer 2 | PM-1M(0.10) | A-1M(0.30) | B-3M(0.30) | B-7M(0.30) | — | — |
|  | 2-3 | Polymer 3 | PM-1M(0.10) | A-1M(0.20) | B-6M(0.15) | B-1M(0.30) | B-5M(0.25) | — |
|  | 2-4 | Polymer 4 | PM-1M(0.10) | A-1M(0.10) | B-6M(0.25) | B-1M(0.20) | B-5M(0.15) | A-5M(0.20) |
|  | 2-5 | Polymer 5 | PM-2M(0.10) | A-1M(0.30) | B-3M(0.30) | B-1M(0.30) | — | — |
|  | 2-6 | Polymer 6 | PM-2M(0.10) | A-1M(0.30) | B-6M(0.40) | B-1M(0.20) | — | — |
|  | 2-7 | Polymer 7 | PM-2M(0.10) | A-1M(0.30) | B-3M(0.30) | B-7M(0.30) | — | — |
|  | 2-8 | Polymer 8 | PM-2M(0.10) | A-1M(0.30) | B-6M(0.30) | B-7M(0.30) | — | — |
|  | 2-9 | Polymer 9 | PM-2M(0.10) | A-1M(0.20) | B-3M(0.30) | B-7M(0.30) | A-3M(0.10) | — |
|  | 2-10 | Polymer 10 | PM-2M(0.10) | A-1M(0.30) | B-3M(0.30) | B-2M(0.30) | — | — |
|  | 2-11 | Polymer 11 | PM-2M(0.10) | A-1M(0.30) | B-3M(0.30) | B-1M(0.20) | C-3M(0.10) | — |
|  | 2-12 | Polymer 12 | PM-2M(0.10) | A-1M(0.30) | B-3M(0.30) | B-1M(0.20) | C-1M(0.10) | — |
|  | 2-13 | Polymer 13 | PM-2M(0.10) | A-3M(0.30) | B-3M(0.30) | B-1M(0.20) | C-2M(0.10) | — |
|  | 2-14 | Polymer 14 | PM-2M(0.10) | A-1M(0.30) | B-3M(0.30) | B-1M(0.20) | C-4M(0.10) | — |
|  | 2-15 | Polymer 15 | PM-2M(0.10) | A-4M(0.30) | B-3M(0.30) | B-1M(0.20) | C-3M(0.10) | — |
|  | 2-16 | Polymer 16 | PM-2M(0.10) | A-2M(0.20) | B-3M(0.30) | B-1M(0.30) | A-3M(0.10) | — |
|  | 2-17 | Polymer 17 | PM-2M(0.10) | A-1M(0.30) | B-4M(0.30) | B-1M(0.30) | — | — |
|  | 2-18 | Polymer 18 | D-2M(0.70) | D-4M(0.30) | — | — | — | — |
|  | 2-19 | Polymer 19 | D-2M(0.90) | D-6M(0.10) | — | — | — | — |
|  | 2-20 | Polymer 20 | PM-2M(0.05) | D-2M(0.60) | D-4M(0.35) | — | — | — |
|  | 2-21 | Polymer 21 | PM-2M(0.05) | D-2M(0.85) | D-6M(0.10) | — | — | — |
|  | 2-22 | Polymer 22 | PM-2M(0.05) | D-2M(0.85) | D-7M(0.10) | — | — | — |
|  | 2-23 | Polymer 23 | D-1M(0.90) | D-6M(0.10) | — | — | — | — |
|  | 2-24 | Polymer 24 | PM-2M(0.05) | D-1M(0.60) | D-4M(0.35) | — | — | — |
|  | 2-25 | Polymer 25 | PM-2M(0.05) | D-1M(0.85) | D-6M(0.10) | — | — | — |
|  | 2-26 | Polymer 26 | PM-2M(0.05) | D-1M(0.85) | D-7M(0.10) | — | — | — |
|  | 2-27 | Polymer 27 | PM-2M(0.05) | D-1M(0.65) | D-6M(0.10) | D-3M(0.20) | — | — |
|  | 2-28 | Polymer 28 | PM-2M(0.05) | D-1M(0.65) | D-7M(0.10) | D-3M(0.20) | — | — |
|  | 2-29 | Polymer 33 | PM-1M(0.05) | A-1M(0.30) | B-3M(0.30) | B-7M(0.30) |  |  |
|  | 2-30 | Polymer 34 | PM-4M(0.05) | A-1M(0.30) | B-3M(0.30) | B-7M(0.30) |  |  |
|  | 2-31 | Polymer 35 | PM-1M(0.05) | D-1M(0.65) | D-6M(0.10) | D-3M(0.20) |  |  |
|  | 2-32 | Polymer 36 | PM-4M(0.05) | D-1M(0.65) | D-6M(0.10) | D-3M(0.20) |  |  |
| Comparative Synthesis Example | 1-1 | Polymer 29 |  | A-1M(0.30) | B-3M(0.45) | B-1M(0.25) | — | — |
|  | 1-2 | Polymer 30 | PM-3M(0.10) | A-1M(0.30) | B-3M(0.30) | B-1M(0.30) | — | — |
|  | 1-3 | Polymer 31 | D-1M(0.70) | D-4M(0.30) | — | — | — | — |
|  | 1-4 | Polymer 32 | D-1M(0.70) | D-6M(0.10) | D-3M(0.20) | — | — | — |

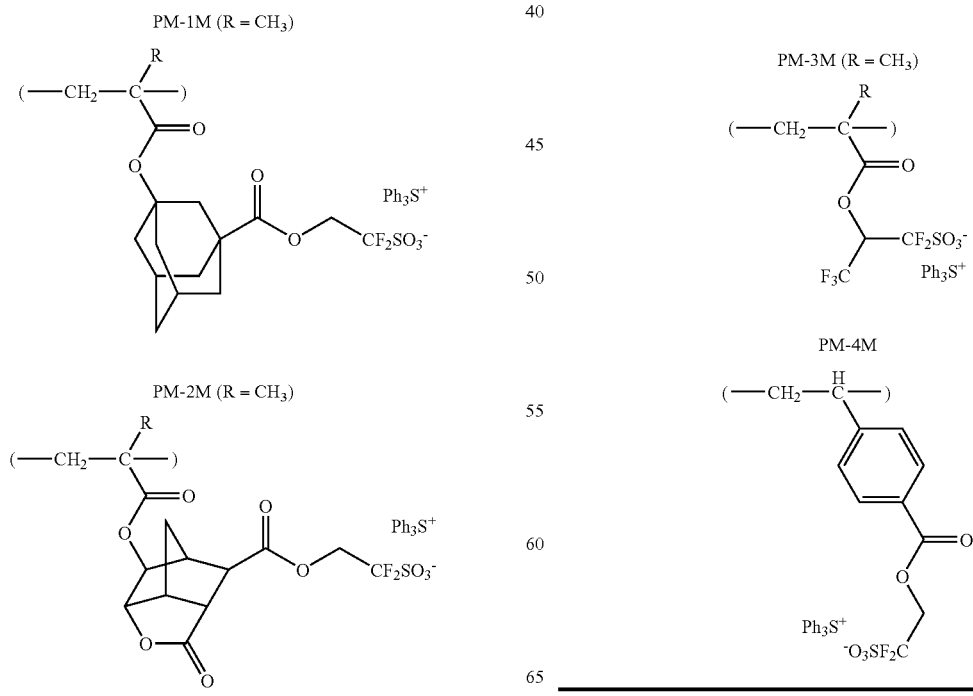

TABLE 2 / TABLE 2-continued

PM-1M (R = CH$_3$)

PM-2M (R = CH$_3$)

PM-3M (R = CH$_3$)

PM-4M

TABLE 3
A-1M (R = CH₃)
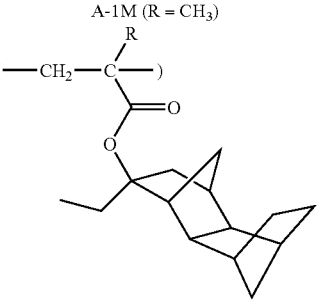
A-2M (R = CH₃)
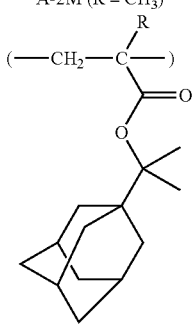
A-3M (R = CH₃)
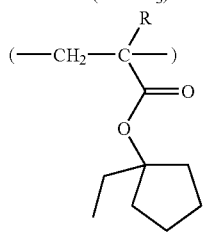
A-4M (R = CH₃)
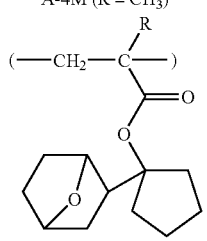
A-5M (R = CH₃)
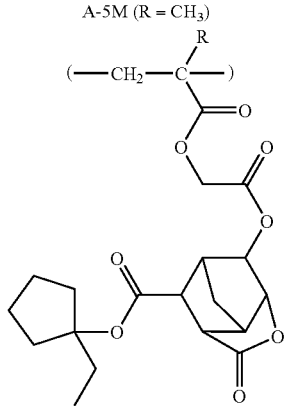
TABLE 4
B-1M (R = CH₃)
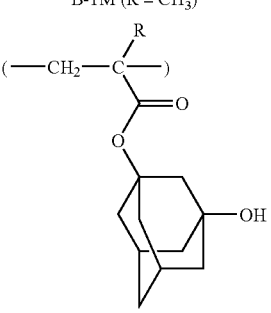
B-2M (R = CH₃)
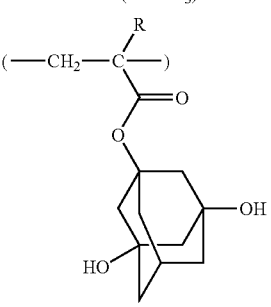
B-3M (R = CH₃)
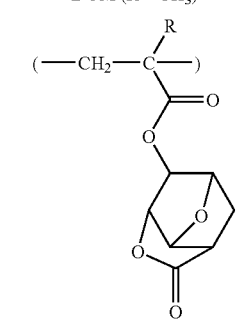
B-4M (R = CH₃)
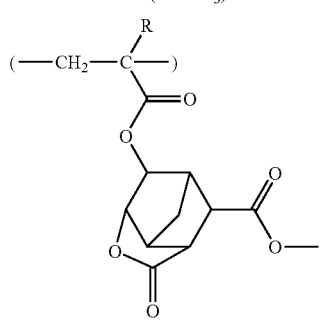

TABLE 4-continued
B-5M (R = CH₃)
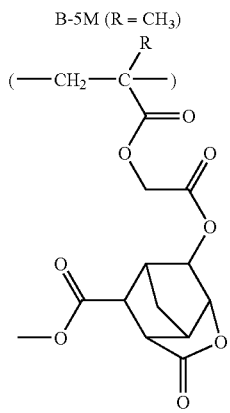
B-6M (R = CH₃)
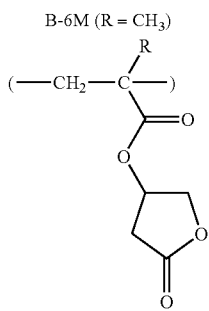
B-7M (R = CH₃)
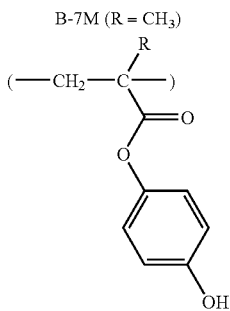
TABLE 5
C-1M (R = CH₃)
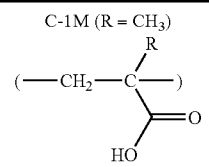
C-2M (R = CH₃)
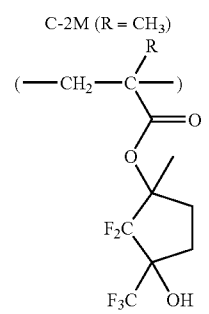
TABLE 5-continued
C-3M (R = CH₃)
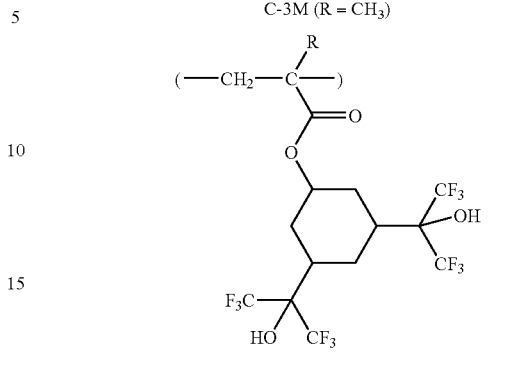
C-4M (R = CH₃)
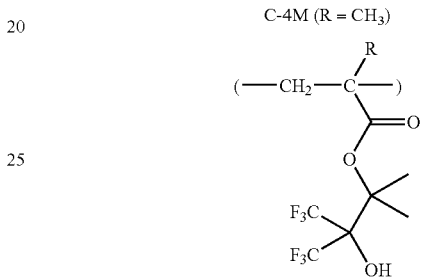
TABLE 6
D-1M
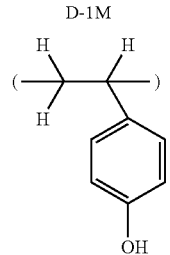
D-2M
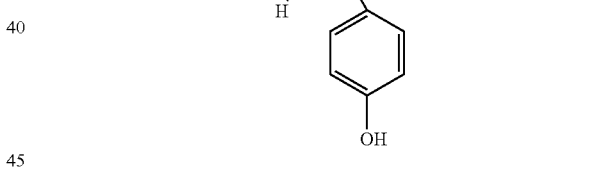

TABLE 6-continued

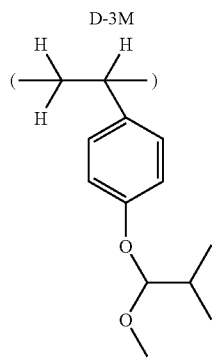

D-3M

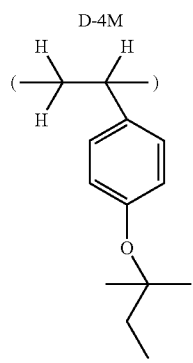

D-4M

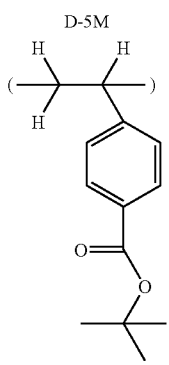

D-5M

D-6M

TABLE 6-continued

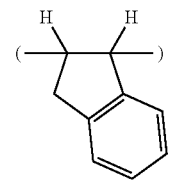

D-7M

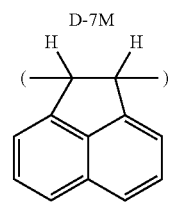

D-8M

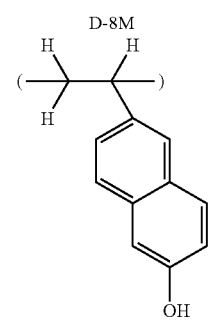

Preparation of Resist Compositions

Examples 1-1 to 1-24 & Comparative Examples 1-1 to 1-4

Resist compositions were prepared by using inventive resins (Polymer 1 to 17, 24, 27, 28, 33 to 36, abbreviated P-01 to P-17, P-24, P-27, P-28 and P-33 to P-36) or comparative resins (Polymers 29 to 32, abbreviated P-29 to P-32) as the base resin, and dissolving the polymer, an acid generator (PAG), and a quencher (Base) in a solvent mixture (PGMEA and CyHO) in accordance with the recipe shown in Table 7. These compositions were each filtered through a Teflon® filter having a pore diameter 0.2 μm, thereby giving inventive resist solutions (R-01 to 20, R-25 to 28) and comparative resist solutions (R-21 to 24). Note that the solvent contained 0.01 wt % of surfactant (Surfactant 1, Omnova Solutions, Inc.).

TABLE 7

|  |  | Resist | Resin (pbw) | PAG (pbw) | Base (pbw) | Solvent 1 (pbw) | Solvent 2 (pbw) |
|---|---|---|---|---|---|---|---|
| Example | 1-1 | R-01 | P-01 (80) | — | Base-1 (1.10) | PGMEA (896) | CyHO (364) |
|  | 1-2 | R-02 | P-02 (80) | — | Base-1 (1.10) | PGMEA (896) | CyHO (364) |
|  | 1-3 | R-03 | P-03 (80) | — | Base-1 (1.10) | PGMEA (896) | CyHO (364) |
|  | 1-4 | R-04 | P-04 (80) | — | Base-1 (1.10) | PGMEA (896) | CyHO (364) |
|  | 1-5 | R-05 | P-05 (80) | — | Base-1 (1.10) | PGMEA (896) | CyHO (364) |
|  | 1-6 | R-06 | P-06 (80) | — | Base-1 (1.10) | PGMEA (896) | CyHO (364) |
|  | 1-7 | R-07 | P-07 (80) | — | Base-1 (1.10) | PGMEA (896) | CyHO (364) |
|  | 1-8 | R-08 | P-08 (80) | — | Base-1 (1.10) | PGMEA (896) | CyHO (364) |

TABLE 7-continued

|  |  | Resist | Resin (pbw) | PAG (pbw) | Base (pbw) | Solvent 1 (pbw) | Solvent 2 (pbw) |
|---|---|---|---|---|---|---|---|
|  | 1-9 | R-09 | P-09 (80) | — | Base-1 (1.10) | PGMEA (896) | CyHO (364) |
|  | 1-10 | R-10 | P-10 (80) | — | Base-2 (1.10) | PGMEA (896) | CyHO (364) |
|  | 1-11 | R-11 | P-11 (80) | — | Base-2 (1.10) | PGMEA (896) | CyHO (364) |
|  | 1-12 | R-12 | P-12 (80) | — | Base-2 (1.10) | PGMEA (896) | CyHO (364) |
|  | 1-13 | R-13 | P-13 (80) | — | Base-2 (1.10) | PGMEA (896) | CyHO (364) |
|  | 1-14 | R-14 | P-14 (80) | — | Base-2 (1.10) | PGMEA (896) | CyHO (364) |
|  | 1-15 | R-15 | P-15 (80) | — | Base-2 (1.10) | PGMEA (896) | CyHO (364) |
|  | 1-16 | R-16 | P-16 (80) | — | Base-2 (1.10) | PGMEA (896) | CyHO (364) |
|  | 1-17 | R-17 | P-17 (80) | PAG-II (3.0) | Base-2 (1.10) | PGMEA (896) | CyHO (364) |
|  | 1-18 | R-18 | P-24 (80) | — | Base-1 (1.10) | PGMEA (896) | EL (364) |
|  | 1-19 | R-19 | P-27 (80) | — | Base-1 (1.10) | PGMEA (896) | EL (364) |
|  | 1-20 | R-20 | P-28 (80) | — | Base-1 (1.10) | PGMEA (896) | EL (364) |
|  | 1-21 | R-25 | P-33 (80) | — | Base-1 (1.10) | PGMEA (896) | CyHO (364) |
|  | 1-22 | R-26 | P-34 (80) | — | Base-1 (1.10) | PGMEA (896) | CyHO (364) |
|  | 1-23 | R-27 | P-35 (80) | — | Base-1 (1.10) | PGMEA (896) | EL (364) |
|  | 1-24 | R-28 | P-36 (80) | — | Base-1 (1.10) | PGMEA (896) | EL (364) |
| Comparative Example | 1-1 | R-21 | P-29 (80) | PAG-II (7.6) | Base-1 (1.10) | PGMEA (896) | CyHO (364) |
|  | 1-2 | R-22 | P-30 (80) | — | Base-1 (1.10) | PGMEA (896) | CyHO (364) |
|  | 1-3 | R-23 | P-31 (80) | PAG-I (6.5) | Base-1 (1.10) | PGMEA (896) | EL (364) |
|  | 1-4 | R-24 | P-32 (80) | PAG-I (6.5) | Base-1 (1.10) | PGMEA (896) | EL (364) |

The acid generator, quencher (base) and solvent shown in Table 7 have the following meanings.
PAG-I: triphenylsulfonium perfluoro-1-butanesulfonate
PAG-II: triphenylsulfonium 2-(adamantane-1-carbonyloxy)-1,1,3,3,3-pentafluoropropane-1-sulfonate (described in JP-A 2007-145797)
Base-1: tri(2-methoxymethoxyethyl)amine
Base-2: 2-morpholinoethyl laurate
PGMEA: 1-methoxyisopropyl acetate
CyHO: cyclohexanone
EL: ethyl lactate
Surfactant 1: 3-methyl-3-(2,2,2-trifluoroethoxymethyl)-oxetane/tetrahydrofuran/2,2-dimethyl-1,3-propane diol copolymer (Omnova Solutions, Inc.)

Evaluation of Resolution, Exposure Latitude and Line Width Roughness on ArF Lithography Examples 2-1 to 2-19 & Comparative Examples 2-1 to 2-2

On a silicon substrate, an antireflective coating solution (ARC-29A, Nissan Chemical Co., Ltd.) was coated and baked at 200° C. for 60 seconds to form an ARC of 78 nm thick. Each of inventive resist compositions (R-01 to 17, 25 and 26) and comparative resist compositions (R-21 and 22) was spin coated on the ARC-coated silicon substrate and baked on a hot plate at 100° C. for 60 seconds, forming a resist film of 100 nm thick. The wafer was exposed by means of an ArF excimer laser scanner NSR-S307E (Nikon Corp., NA 0.85, ⅘ annular illumination, 6% halftone phase shift mask), post-exposure baked (PEB) at 100° C. for 60 seconds, and developed with a 2.38 wt % tetramethylammonium hydroxide aqueous solution for 60 seconds.

The optimum exposure (Eop) was defined as the exposure dose (mJ/cm$^2$) which provided a 1:1 resolution at the top and bottom of a 80-nm grouped line-and-space pattern. The maximum resolution of the resist was defined as the minimum line width (nm) of a line-and-space pattern that was resolved and separated at the optimum exposure. For the evaluation of exposure latitude, an exposure dose tolerance which provided a pattern size of 80 nm±10% when the exposure dose was changed from the optimum was determined, and the tolerance value was divided by the optimum dose and expressed in percent. A greater value indicates a smaller performance change with a change of exposure dose, that is, better exposure latitude. The line width roughness (LWR) of a 80-nm line-and-space pattern was measured using measurement SEM (S-9380 by Hitachi Hitechnologies, Ltd.).

TABLE 8

|  |  | Resist composition | Eop (mJ/cm$^2$) | Maximum resolution (nm) | Exposure latitude (%) | LWR (nm) |
|---|---|---|---|---|---|---|
| Example | 2-1 | R-01 | 31 | 70 | 14.0 | 5.2 |
|  | 2-2 | R-02 | 32 | 70 | 13.5 | 5.4 |
|  | 2-3 | R-03 | 30 | 75 | 13.9 | 5.3 |
|  | 2-4 | R-04 | 34 | 75 | 13.7 | 5.4 |
|  | 2-5 | R-05 | 33 | 70 | 14.2 | 4.4 |
|  | 2-6 | R-06 | 33 | 75 | 14.5 | 4.0 |
|  | 2-7 | R-07 | 32 | 70 | 13.8 | 4.6 |
|  | 2-8 | R-08 | 31 | 75 | 14.0 | 4.9 |
|  | 2-9 | R-09 | 33 | 70 | 13.9 | 4.8 |
|  | 2-10 | R-10 | 35 | 75 | 13.8 | 5.0 |
|  | 2-11 | R-11 | 31 | 70 | 14.0 | 4.9 |
|  | 2-12 | R-12 | 32 | 70 | 13.6 | 4.3 |
|  | 2-13 | R-13 | 34 | 75 | 14.7 | 4.8 |
|  | 2-14 | R-14 | 36 | 70 | 14.1 | 5.0 |
|  | 2-15 | R-15 | 33 | 75 | 14.7 | 4.4 |
|  | 2-16 | R-16 | 30 | 70 | 13.8 | 4.2 |
|  | 2-17 | R-17 | 32 | 75 | 14.4 | 5.2 |
|  | 2-18 | R-25 | 35 | 75 | 13.8 | 5.3 |
| Comparative | 2-19 | R-26 | 32 | 70 | 14.7 | 4.4 |
| Example | 2-1 | R-21 | 30 | 80 | 11.7 | 7.5 |
|  | 2-2 | R-22 | 37 | 80 | 10.8 | 8.2 |

The data of Examples in Table 8 demonstrate that the inventive resist compositions exhibit good resolution performance, good exposure latitude and low LWR values when processed by ArF excimer laser lithography.

Evaluation of Resolution on EB Lithography

Examples 3-1 to 3-5 & Comparative Examples 3-1 to 3-2

On a 8-inch silicon wafer having an antireflective coating (DUV-42 by Brewer Science) of 610 Å thick coated thereon, each of the inventive resist compositions (R-18 to 20, 27 and 28) or comparative resist compositions (R-23 and 24) was spin coated and heat treated at 100° C. for 60 seconds to form a resist film of 2,000 Å thick. Using an EB lithography system HL-800D (Hitachi Hitechnologies, Ltd.) at an accelerating voltage of 50 keV, exposure was performed on the resist film. The resist film was post-exposure baked (PEB) at 120° C. for 60 seconds and developed with a 2.38 wt % TMAH aqueous solution, obtaining a positive pattern.

The resist pattern was evaluated as follows. The optimum exposure (sensitivity, Eop) was defined as the exposure dose (μC/cm$^2$) which provided a 1:1 resolution at the top and bottom of a 120-nm line-and-space pattern. The resolution of the resist was defined as the minimum line width of a line-and-space pattern that was ascertained separate at the optimum exposure. The profile of the resolved resist pattern was evaluated by observing a cross section of the resist under a SEM.

The post-exposure delay (PED) in vacuum was evaluated by exposing the coated wafer on an EB lithography system, holding it in the vacuum system for 24 hours, thereafter effecting PEB and development. The size of lines of a 120-nm line-and-space pattern was measured and a percent change thereof was calculated. For example, when the line size increases by 12 nm, the change is reported as +10%. A smaller change indicates better stability. The test results are shown in Table 9.

TABLE 9

|  |  | Resist composition | Eop (μC/cm$^2$) | Resolution (nm) | Pattern profile | Line size change by PED |
|---|---|---|---|---|---|---|
| Example | 3-1 | R-18 | 18 | 80 | Rectangular | 0 |
|  | 3-2 | R-19 | 20 | 80 | Rectangular | 0 |
|  | 3-3 | R-20 | 20 | 80 | Rectangular | 0 |
|  | 3-4 | R-27 | 20 | 80 | Rectangular | 0 |
|  | 3-5 | R-28 | 18 | 80 | Rectangular | 0 |
| Comparative Example | 3-1 | R-23 | 25 | 100 | Somewhat rounded top | +10% |
|  | 3-2 | R-24 | 25 | 100 | Somewhat rounded top | +10% |

It is evident from Table 9 that the resist composition of the invention is also improved in resolution and vacuum PED when processed by EB lithography.

Evaluation of Sensitivity and Resolution on EUV Lithography

Examples 4-1 to 4-10 & Comparative Examples 4-1 to 4-2

On a silicon wafer treated with hexamethyldisilazane (HMDS), each of inventive resist compositions (R-01 to 08, 25 and 26) or comparative resist compositions (R-21 and 22) was spin coated and baked at 110° C. for 60 seconds, forming a resist film of 50 nm thick. The wafer was exposed by means of an EUV microstepper (NA 0.3, monopolar illumination), post-exposure baked (PEB) at 95° C. for 60 seconds, and developed with a 2.38 wt % tetramethylammonium hydroxide aqueous solution for 30 seconds, obtaining a positive pattern.

The optimum exposure (sensitivity, Eop) was defined as the exposure dose (mJ/cm$^2$) which provided a 1:1 resolution at the top and bottom of a 32-nm line-and-space pattern. The resolution of the resist was defined as the minimum line width (nm) of a line-and-space pattern that was resolved and separated at the optimum exposure. The results are shown in Table 10.

TABLE 10

| | | Resist composition | Eop (mJ/cm$^2$) | Resolution (nm) |
|---|---|---|---|---|
| Example | 4-1 | R-01 | 17 | 24 |
| | 4-2 | R-02 | 15 | 25 |
| | 4-3 | R-03 | 14 | 25 |
| | 4-4 | R-04 | 16 | 26 |
| | 4-5 | R-05 | 18 | 24 |
| | 4-6 | R-06 | 17 | 24 |
| | 4-7 | R-07 | 18 | 26 |
| | 4-8 | R-08 | 16 | 25 |
| | 4-9 | R-25 | 18 | 26 |
| | 4-10 | R-26 | 15 | 25 |
| Comparative Example | 4-1 | R-21 | 27 | 32 |
| | 4-2 | R-22 | 24 | 30 |

It is evident from Table 10 that the resist composition of the invention is also improved in sensitivity and resolution when processed by EUV lithography.

The patent documents cited are incorporated herein by reference.

Japanese Patent Application No. 2008-268147 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A sulfonium salt having the general formula (1):

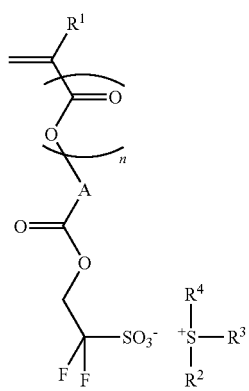

wherein $R^1$ is hydrogen, fluorine, methyl or trifluoromethyl, $R^2$, $R^3$ and $R^4$ are each independently a substituted or unsubstituted, straight or branched $C_1$-$C_{10}$ alkyl, alkenyl or oxoalkyl group or a substituted or unsubstituted $C_6$-$C_{18}$ aryl, aralkyl or aryloxoalkyl group, or at least two of $R^2$, $R^3$ and $R^4$ may bond together to form a ring with the sulfur atom, A is a divalent $C_2$-$C_{20}$ hydrocarbon group of cyclic structure which may contain a heteroatom, and n is 0 or 1.

2. A polymer capable of generating a sulfonic acid in response to high-energy radiation or heat, the sulfonic acid comprising recurring units of the general formula (1a):

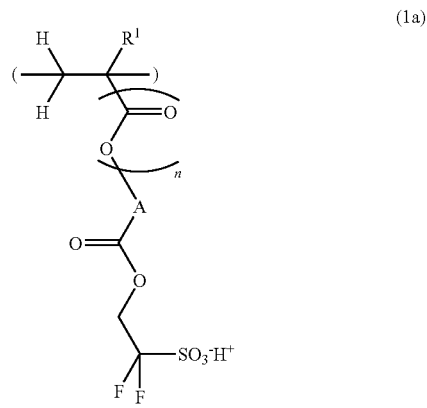

wherein $R^1$ is hydrogen, fluorine, methyl or trifluoromethyl, A is a divalent $C_2$-$C_{20}$ hydrocarbon group of cyclic structure which may contain a heteroatom, and n is 0 or 1.

3. A polymer comprising recurring units of the general formula (1b):

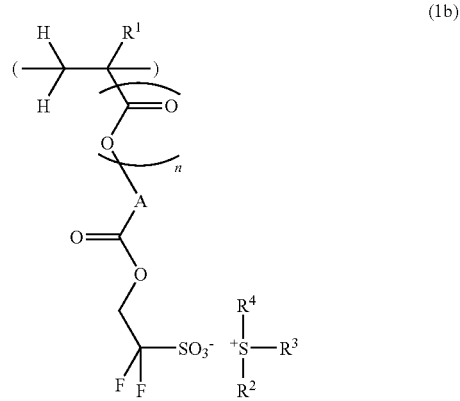

wherein $R^1$ is hydrogen, fluorine, methyl or trifluoromethyl, $R^2$, $R^3$ and $R^4$ are each independently a substituted or unsubstituted, straight or branched $C_1$-$C_{10}$ alkyl, alkenyl or oxoalkyl group or a substituted or unsubstituted $C_6$-$C_{18}$ aryl, aralkyl or aryloxoalkyl group, or at least two of $R^2$, $R^3$ and $R^4$ may bond together to form a ring with the sulfur atom, A is a divalent $C_2$-$C_{20}$ hydrocarbon group of cyclic structure which may contain a heteroatom, and n is 0 or 1.

4. The polymer of claim 3, further comprising recurring units of at least one type selected from the general formulae (2) to (6):

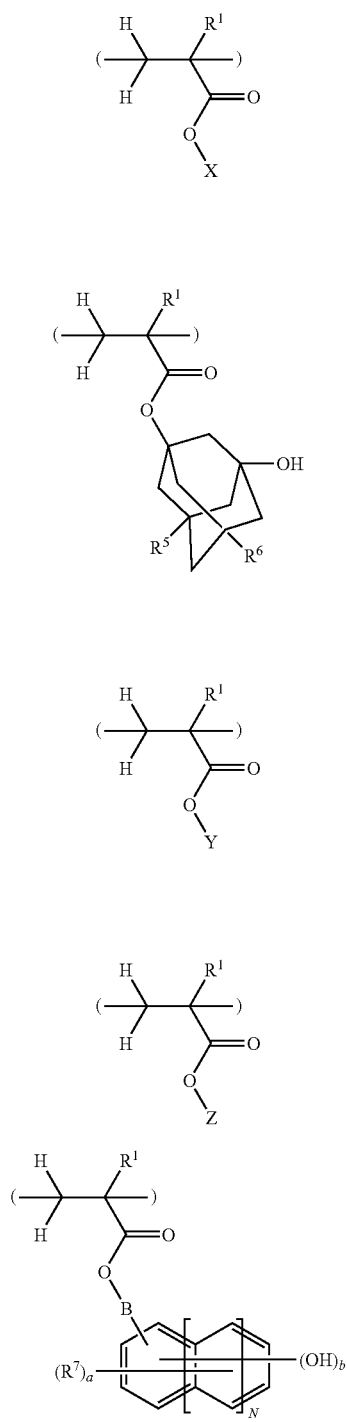

5. The polymer of claim 3, further comprising recurring units of at least one type selected from the general formulae (7) to (11):

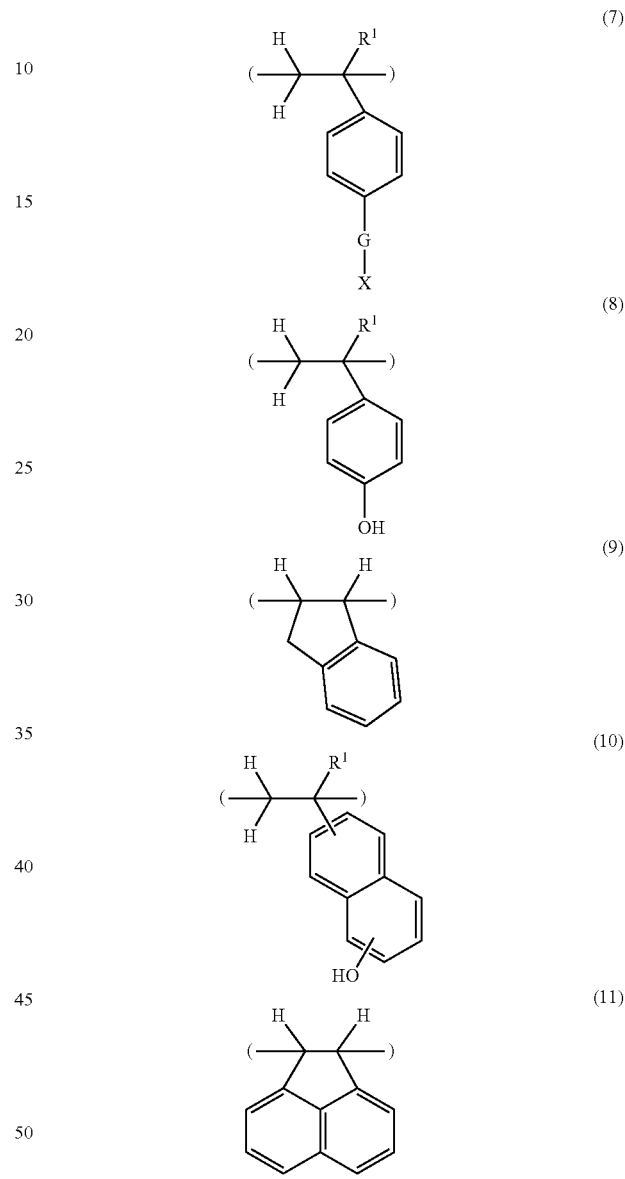

wherein $R^1$ is as defined above, X is an acid labile group, and G is oxygen or carbonyloxy (—C(=O)O—).

6. A resist composition comprising the polymer of claim 3 as a base resin.

7. The resist composition of claim 6, further comprising a surfactant which is insoluble in water and soluble in an alkaline developer.

8. A pattern forming process comprising the steps of:
applying the resist composition of claim 6 onto a substrate to form a coating,
heat treating the coating and exposing it to high-energy radiation through a photomask,
optionally heat treating the exposed coating and developing it with a developer.

wherein $R^1$ is as defined above, $R^5$ and $R^6$ are each independently hydrogen or hydroxyl, X is an acid labile group, Y is a substituent group having lactone structure, Z is hydrogen, $C_1$-$C_{15}$ fluoroalkyl or $C_1$-$C_{15}$ fluoroalcohol-containing substituent group, N is an integer of 0 to 2, $R^7$ is hydrogen or $C_1$-$C_{10}$ alkyl, B is a single bond or a divalent $C_1$-$C_{10}$ hydrocarbon group which may have oxygen substituted thereon, a is an integer of 0 to 3, and b is an integer of 1 to 3.

9. A pattern forming process comprising the steps of:
applying the resist composition of claim 6 onto a substrate to form a resist coating,
heat treating the resist coating,
applying onto the resist coating a protective coating which is insoluble in water and soluble in an alkaline developer,
exposing the coated substrate to high-energy radiation from a projection lens through a photomask while holding water between the substrate and the projection lens, optionally heat treating the exposed coating and developing it with a developer.

10. A pattern forming process comprising the steps of applying the resist composition of claim 6 onto a substrate to form a coating, heat treating the coating, imagewise writing with an electron beam, optionally heat treating the coating, and developing it with a developer.

11. A resist composition comprising the polymer of claim 3 and a polymer free of recurring units of formula (1b) as a base resin.

* * * * *